US011040231B2

(12) United States Patent
Rubin et al.

(10) Patent No.: US 11,040,231 B2
(45) Date of Patent: Jun. 22, 2021

(54) SYSTEMS FOR DYNAMIC RESISTANCE TRAINING

(71) Applicant: Arena Innovation Corp., New York, NY (US)

(72) Inventors: Zachary M. Rubin, San Jose, CA (US); Ilya Polyakov, San Francisco, CA (US); Dan Hammer, Douglasville, GA (US)

(73) Assignee: Arena Innovation Corp., New York, NY (US)

( * ) Notice: Subject to any disclaimer, the term of this patent is extended or adjusted under 35 U.S.C. 154(b) by 178 days.

(21) Appl. No.: 15/884,074

(22) Filed: Jan. 30, 2018

(65) Prior Publication Data

US 2018/0214729 A1     Aug. 2, 2018

Related U.S. Application Data

(60) Provisional application No. 62/499,622, filed on Jan. 30, 2017, provisional application No. 62/604,457, filed on Jul. 7, 2017.

(51) Int. Cl.
*A63B 21/005*     (2006.01)
*A63B 24/00*      (2006.01)
(Continued)

(52) U.S. Cl.
CPC ........ *A63B 21/0058* (2013.01); *A63B 21/153* (2013.01); *A63B 21/156* (2013.01); *A63B 21/4043* (2015.10); *A63B 23/03541* (2013.01); *A63B 23/1209* (2013.01); *A63B 24/0087* (2013.01); *A63B 71/0622* (2013.01);
(Continued)

(58) Field of Classification Search
CPC ....... A63B 21/0058–0059; A63B 21/153–156; A63B 21/0023; A63B 24/0087; A63B 2024/0093
See application file for complete search history.

(56) References Cited

U.S. PATENT DOCUMENTS 2,778,053 A     1/1957  Hess et al.
4,235,437 A    11/1980  Ruis et al.
(Continued)

OTHER PUBLICATIONS

Book et al., Control of a Robotic Exercise Machine, Joint Automatic Control Conference, Charlottesville, Virginia, 1981 (7 pages).
(Continued)

*Primary Examiner* — Jennifer Robertson
(74) *Attorney, Agent, or Firm* — Polsinelli PC

(57) ABSTRACT

Systems and methods for dynamic resistance training are provided that include the use of a dynamic force module. The dynamic force module includes an actuator and controller adapted to control the actuator according to a force profile that specifies the relationship between an operational parameter of the actuator and a measured parameter associated with a user performing an exercise. The dynamic force module is also capable of communicating with a broader network system to facilitate storing and distribution of force profiles and user profile information. The network system further includes features for, among other things, generating and managing force profiles, uploading multimedia content, and tracking user progress.

10 Claims, 29 Drawing Sheets

(51) Int. Cl.
    *A63B 21/00*     (2006.01)
    *A63B 23/035*     (2006.01)
    *A63B 23/12*     (2006.01)
    *A63B 71/06*     (2006.01)
    *G16H 20/30*     (2018.01)
    *A63B 21/04*     (2006.01)
    *A63B 69/00*     (2006.01)
    *A63B 23/04*     (2006.01)

(52) U.S. Cl.
    CPC ........ *G16H 20/30* (2018.01); *A63B 21/00196* (2013.01); *A63B 21/0421* (2013.01); *A63B 23/03525* (2013.01); *A63B 23/0494* (2013.01); *A63B 69/0053* (2013.01); *A63B 2024/0093* (2013.01); *A63B 2024/0096* (2013.01); *A63B 2071/068* (2013.01); *A63B 2071/0627* (2013.01); *A63B 2071/0655* (2013.01); *A63B 2071/0677* (2013.01); *A63B 2220/05* (2013.01); *A63B 2220/40* (2013.01); *A63B 2220/58* (2013.01); *A63B 2220/70* (2013.01); *A63B 2220/801* (2013.01); *A63B 2220/805* (2013.01); *A63B 2220/806* (2013.01); *A63B 2225/096* (2013.01); *A63B 2225/15* (2013.01); *A63B 2225/20* (2013.01); *A63B 2225/50* (2013.01)

(56) References Cited

U.S. PATENT DOCUMENTS

| | | | |
|---|---|---|---|
| 4,556,216 A | | 12/1985 | Pitkanen |
| 4,661,660 A | | 4/1987 | Sothen et al. |
| 4,744,547 A | | 5/1988 | Hartel |
| 4,869,497 A | | 9/1989 | Stewart et al. |
| 4,979,733 A | * | 12/1990 | Prud'Hon .......... A63B 21/0058 482/4 |
| 5,304,104 A | | 4/1994 | Chi |
| 5,409,435 A | | 4/1995 | Daniels |
| 5,655,997 A | | 8/1997 | Greenberg et al. |
| 5,993,356 A | | 11/1999 | Houston et al. |
| 6,280,361 B1 | | 8/2001 | Harvey et al. |
| 6,612,170 B2 | | 9/2003 | Brown |
| 6,621,014 B1 | | 9/2003 | Tanner et al. |
| 7,121,982 B2 | | 10/2006 | Feldman |
| 7,470,216 B2 | | 12/2008 | Farinelli et al. |
| 8,353,388 B2 | | 1/2013 | Rice et al. |
| 9,586,091 B2 | | 3/2017 | Reich et al. |
| 2004/0000198 A1 | | 1/2004 | Wolf et al. |
| 2005/0223786 A1 | | 10/2005 | Akkerman et al. |
| 2006/0094569 A1 | | 5/2006 | Day |
| 2006/0199708 A1 | * | 9/2006 | Alessandri ......... A63B 21/0628 482/99 |
| 2007/0004567 A1 | | 1/2007 | Shetty et al. |
| 2007/0155587 A1 | * | 7/2007 | Huang ............... A63B 21/0058 482/1 |
| 2010/0125026 A1 | | 5/2010 | Zavadsky et al. |
| 2010/0126543 A1 | | 5/2010 | Cutler |
| 2010/0216600 A1 | | 8/2010 | Noffsinger et al. |
| 2010/0331144 A1 | | 12/2010 | Rindfleisch |
| 2011/0165995 A1 | | 7/2011 | Paulus et al. |
| 2011/0172058 A1 | | 7/2011 | Deaconu et al. |
| 2011/0251021 A1 | | 10/2011 | Zavadsky et al. |
| 2012/0058859 A1 | | 3/2012 | Elsom-Cook et al. |
| 2012/0190502 A1 | | 7/2012 | Paulus et al. |
| 2012/0228062 A1 | | 9/2012 | Taylor |
| 2012/0231929 A1 | | 9/2012 | Hsieh |
| 2014/0038777 A1 | * | 2/2014 | Bird .................. A63B 21/0058 482/5 |
| 2014/0194251 A1 | | 7/2014 | Reich et al. |
| 2014/0287876 A1 | | 9/2014 | Etter et al. |
| 2015/0031505 A1 | | 1/2015 | Hsieh |

OTHER PUBLICATIONS

Loadtech Load Cells (Pty) Ltd, EZEE-Mount System for Simple Installation.
eGYM, https://www.egym.com/, Webpage accessed Jan. 30, 2018.
International Searching Authority, International Search Report and Written Opinion, issued for International Application No. PCT/US2018/015995, dated Apr. 23, 2018 (12 pages).

\* cited by examiner

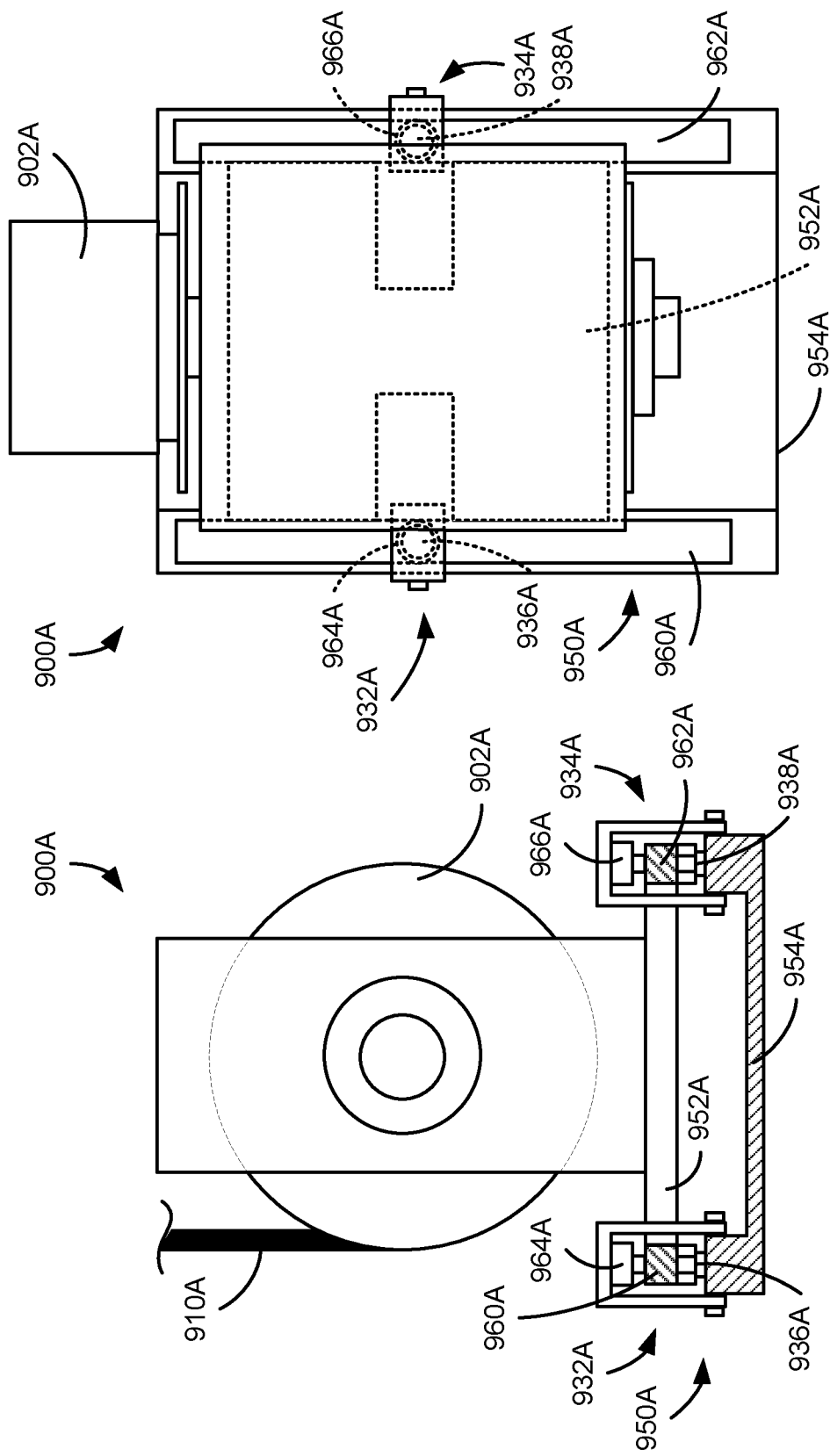

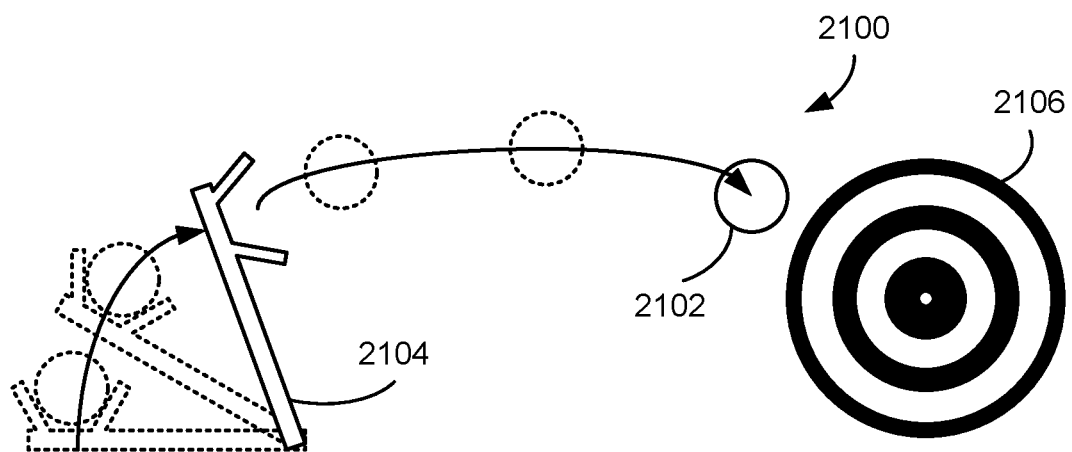
FIG. 21
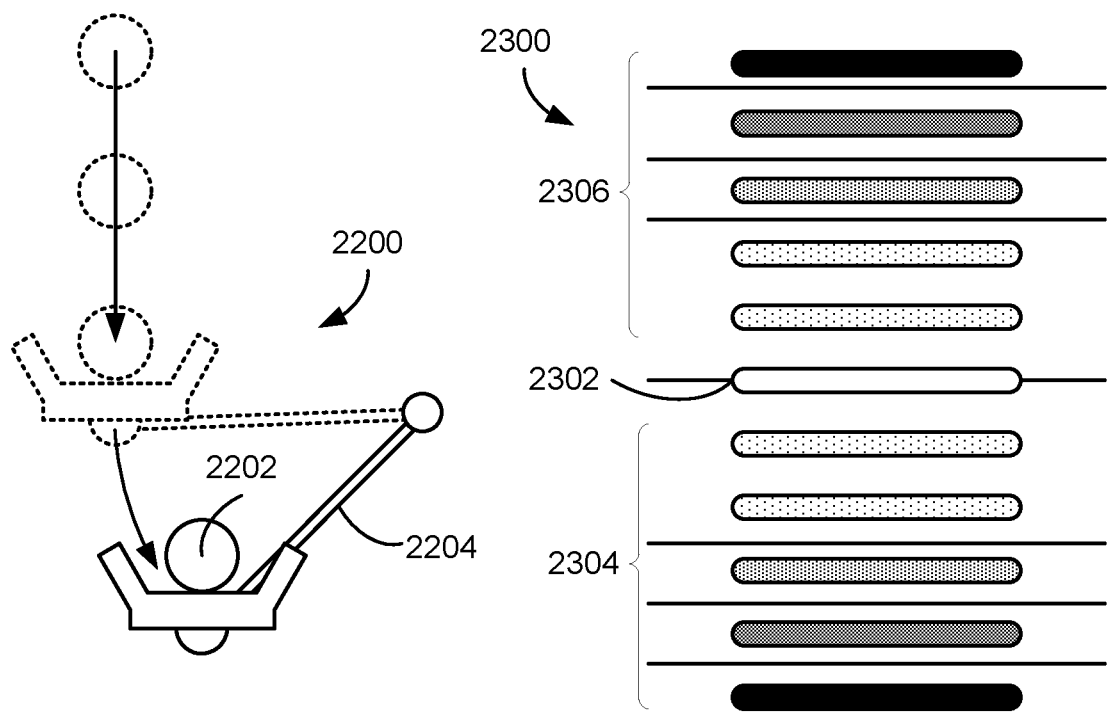
FIG. 22  FIG. 23

# SYSTEMS FOR DYNAMIC RESISTANCE TRAINING

CROSS REFERENCE TO RELATED APPLICATIONS

The present application claims priority under 35 U.S.C. § 119 to U.S. provisional patent application 62/499,622, which was filed Jan. 30, 2017, entitled "Intelligent Dynamic Resistance Training Platform," and to U.S. provisional patent application 62/604,457, which was filed Jul. 7, 2017, entitled "Dynamic Force Algorithms for Strength Training," and both applications are hereby incorporated by reference in their entirety into the present application.

TECHNICAL FIELD

Aspects of the present invention involve an intelligent exercise apparatus and, in particular, a network-enabled exercise apparatus that provides dynamic resistance based on remotely stored user and exercise data.

BACKGROUND

Maintaining a successful exercise regimen is a significant challenge to many individuals with busy schedules, a lack of training and knowledge regarding exercises, and the diligence required to properly track and analyze performance and progress acting as significant roadblocks. For example, many individuals have only a limited amount of time that they can dedicate to working out. As a result, it is critically important that such individuals perform exercises correctly and with an optimal resistance to maximize their results during the limited time available. Variety and cross-training is also very important to maintaining interest, improving motivation, and avoiding injury through cross-training.

It is with these issues in mind that aspects of the present disclosure were conceived.

SUMMARY

In one implementation of the present disclosure a dynamic force module for use in an exercise machine is provided. The dynamic force module includes a motor assembly including a motor and a cable selectively extendable and retractable by actuation of the motor. The dynamic force module further includes a frame coupled to the motor assembly and a load measurement device coupled to the frame and adapted to measure loading of the frame in response to tension applied to the cable.

In another implementation of the present disclosure a dynamic force module for use in an exercise machine is provided. The dynamic force module includes a motor for extending and retracting a cable in response to a control signal, the motor supported by a frame. The dynamic force module further includes a load sensing device configured to measure a load on the frame resulting from tension applied to the cable and a controller communicatively coupled to each of the motor and the load sensing device. The controller is adapted to actuate the motor in response to the load on the frame in accordance with a force profile that provides a relationship between a first parameter associated with operation of the motor and a second parameter corresponding to execution of an exercise by a user of the exercise machine.

In yet another implementation of the present disclosure, a system for managing dynamic resistance exercise equipment is provided. The system includes a computing device communicatively coupled to a force profile data source for storing force profiles. The computing device is configured to receive a request from a dynamic force module for a force profile stored on the data source and to transmit the force profile to the dynamic force module. The force profile provides a relationship between a first parameter associated with operation of an actuator of the dynamic force module and a second parameter corresponding to execution of an exercise by a user of an exercise machine within which the dynamic force module is incorporated.

BRIEF DESCRIPTION OF THE DRAWINGS

Example embodiments are illustrated in referenced figures of the drawings. It is intended that the embodiments and figures disclosed herein are to be considered illustrative rather than limiting.

FIGS. 9A and 9B are a cross-sectional side view and a top view of a second dynamic force module according to the present disclosure.

FIG. 21 is a second example of an interactive animation for providing feedback to a user using a dynamic force module, the second interactive animation corresponding to simulated throwing of an object.

FIG. 22 is a third example of an interactive animation for providing feedback to a user using a dynamic force module, the third interactive animation corresponding to simulated catching of an object.

FIG. 23 is a fourth example of an interactive animation for providing feedback to a user using a dynamic force module, the fourth interactive animation including an indicator including a series of parallel bars.

DETAILED DESCRIPTION

Figure 1:
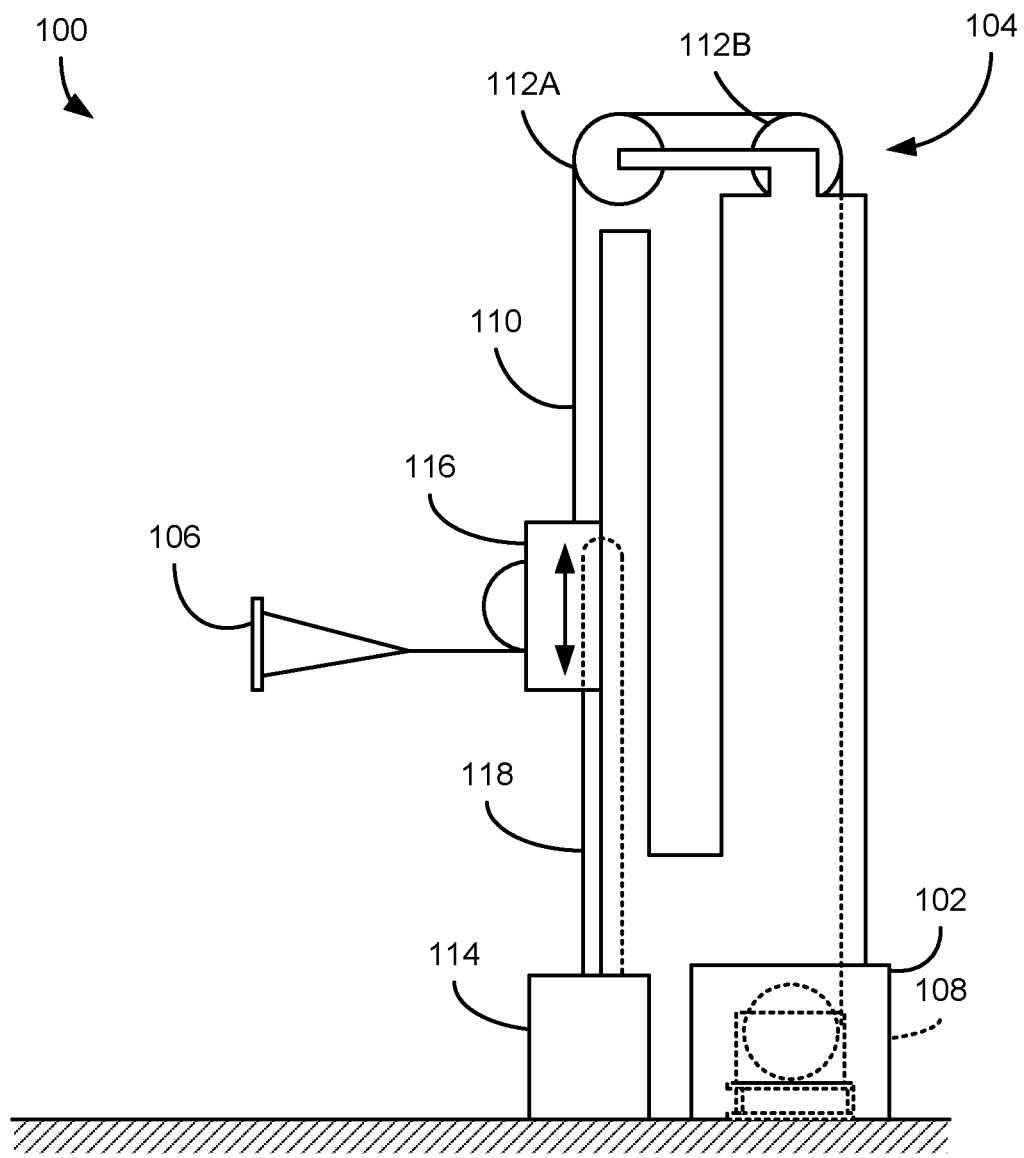
FIG. 1 is a schematic illustration of a first exercise machine including a dynamic force module according to the present disclosure.

The present disclosure is directed to dynamic force modules for use in exercise machines and systems for managing, coordinating, and communicating with dynamic force modules. Dynamic force modules disclosed herein are generally intended to replace the functionality of weights, bands, and other conventional resistance elements in exercise equipment. In particular, the dynamic force modules include an actively controlled actuator that provides reactive force during the performance of an exercise by a user of the dynamic force module. For example, a grip, handle, or other accessory may be coupled to the dynamic force module and manipulated by a user to perform various exercises.

In general, dynamic force modules execute a force profile that provides a relationship between an operational parameter of the dynamic force module (such as a reactive force provided by the dynamic force module) and a measurable parameter of the user as they perform a particular exercise. Although other examples are provided herein, in one basic example, the force profile may indicate a reactive force to be applied by the dynamic force module based on the position of the user during an exercise. Accordingly, as the user performs the exercise associated with the force profile, the dynamic force module operates the actuator in accordance with the force profile.

The dynamic force module may be incorporated into or in communication with various devices for providing feedback to a user. For example, the dynamic force module may be communicatively coupled to a display of an exercise machine in order to present various interactive animations to the user. Such animations may be directed to, among other things, motivating the user, instructing the user, and indicating progress to the user. In certain implementations, the interactive animations may simulate real-world activities and may be presented to the user during the execution of force profiles by the dynamic force module reflecting forces experienced during the activity.

Dynamic force modules in accordance with this disclosure may be communicatively coupled to each other and to other computing devices over a network, such as the Internet. In one implementation, a cloud-based computing platform may interact with dynamic force modules and user computing devices to, among other things, distribute force profiles, store and update user information, and present tracking information to users and personnel such as gym facility managers, personal trainers, physiotherapists, and others who may be working with a user. The cloud-based computing platform further enables the generation, updating, and storage of content for use with dynamic force modules including, but not limited to, force profiles, workout plans, multimedia content, and the like.

The foregoing discussion merely introduces some of the broader concepts associated with dynamic force modules in accordance with this disclosure and is merely intended to provide introductory context for the remainder of this disclosure. In general, this disclosure provides a general overview of dynamic force modules and associated exercise machines followed by a description of an example dynamic force module and various components thereof. The electrical and control aspects of dynamic force modules are then provided including examples of feedback mechanisms and interactive animations that may be provided through a user interface that may be used in conjunction with a dynamic force module. The disclosure further provides a description of a broader network-based computing system for managing, operating, and providing enhanced features of dynamic force modules.

FIG. 1 is a schematic illustration of an exercise machine 100 including a dynamic force module 102 according to the present disclosure. As illustrated, in certain implementations, the exercise machine 100 generally includes a handle 106, strap, grip, belt, or similar component with which a user may apply a force. The handle 106 may in turn be coupled to the dynamic force module 102 by a transmission mechanism 104, which may include, without limitation, one or more of cables, linkages, bars, pulleys, gears, pistons/cylinders, and similar mechanical components. As illustrated in FIG. 1, for example, the transmission mechanism 104 includes a cable 110 that is run through a pair of pulleys 112A, 112B.

The dynamic force module 102 generally includes a computer-controlled actuator 108 which is coupled to or otherwise affixed in proximity to the stationary exercise equipment. The actuator 108 of the dynamic force module 102 may include, for example and without limitation, one or more of a motor, an electromagnet, a hydraulic system, a spring mechanism, a shape memory alloy, or any other suitable actuator. During operation, the actuator 108 applies forces to the handle 106 via the transmission mechanism 104 to generally create a reactive force against movement by a user of the exercise machine. In the exercise machine 100 of FIG. 1, for example, the actuator 108 includes a motor coupled to the cable 110 such that rotation of the motor causes spooling or unspooling of the cable 110, thereby providing resistance to pulling of the cable 110 by a user.

The exercise machine 100 may include adjustable members to adjust the placement or orientation of the exercise machine 100 to perform different exercises or to accommodate users having different physical characteristics. The exercise machine 100, for example, includes a movable block 116 for adjusting the height of the handle 106. In certain implementations, the adjustable members may be manually adjusted by the user; however, in other implementations, the exercise machine 100 may include one or more actuators, such as actuator 114, adapted to move the adjustable members. For example, the block 116 is illustrated in FIG. 1 as being coupled to the actuator 114 by a belt 118 such that the actuator 114 may be used to adjust the height of the block 116.

The vertically movable block 116 of the exercise machine 100 is merely intended as an example of an adjustable member that may be incorporated into exercise machines according to the present disclosure. Other examples of such members may include, without limitation, telescoping members, rotatable members, translatable members, and other movable members for adjusting aspects of the exercise machine 100 to accommodate users of different sizes and/or different exercises. In addition to the motor-driven belt of the exercise machine 100, other actuators may include, without limitation, one or more of motors, hydraulic actuators, pneumatic actuators, linear electric actuators, thermal actuators, and magnetic actuators. In certain implementations, the dynamic force module 102 may be communicatively coupled to the exercise machine 100 such that the dynamic force module 102 can issue commands to the exercise machine 100 and, in particular, to the actuator 114. Such commands may, for example, be used to automatically change the position of adjustable members of the exercise machine 100, such as the block 116.

Figure 2:
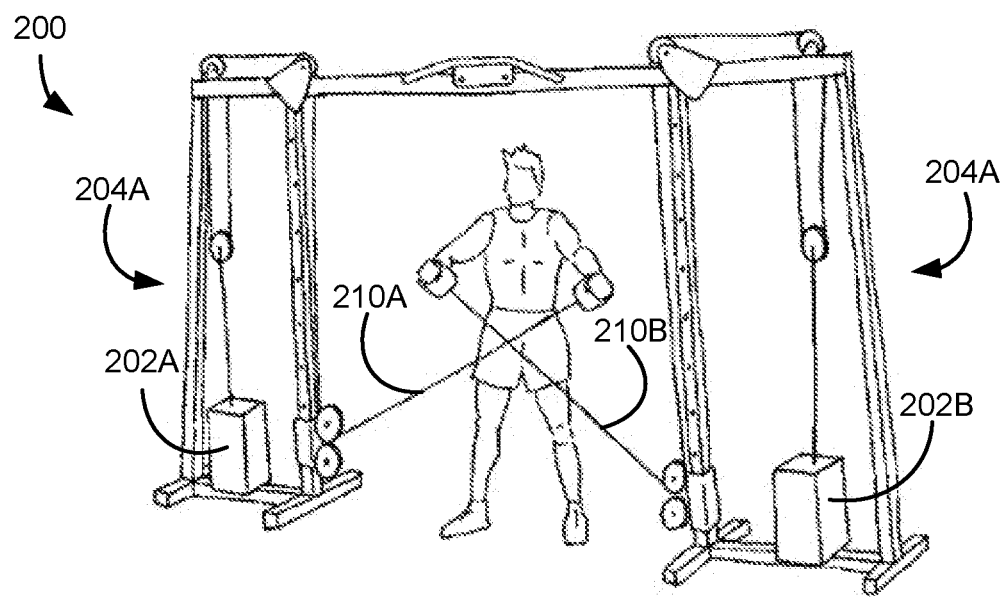
FIG. 2 is a schematic illustration of a second exercise machine including two dynamic force modules according to the present disclosure.

FIGS. 2-5 illustrate alternative implementations of exercise machines in accordance with the present disclosure. First, FIG. 2 illustrates an exercise machine 200 similar to a conventional cable-crossover machine. The exercise machine 200 includes a pair of dynamic force modules 202A, 202B, each of which includes a respective cable 210A, 210B and transmission mechanism 204A, 204B.

In exercise machines according to the present disclosure including multiple dynamic force modules, the dynamic force modules may be operated in a substantially synchronous fashion. In other words, the reactive force provided by each of the dynamic force modules may be generally equal throughout a range of motion performed by a user. In other implementations, however, the dynamic force modules may be operated asynchronously and may provide differing reactive forces. Referring to the exercise machine 200, for example, each of the dynamic force modules 202A, 202B may be configured to provide different reactive forces, thereby providing an imbalanced load to the user. Such load imbalances may be used to, among other things, correct muscle imbalances and accommodate injuries that a user may be experiencing.

Figure 3:
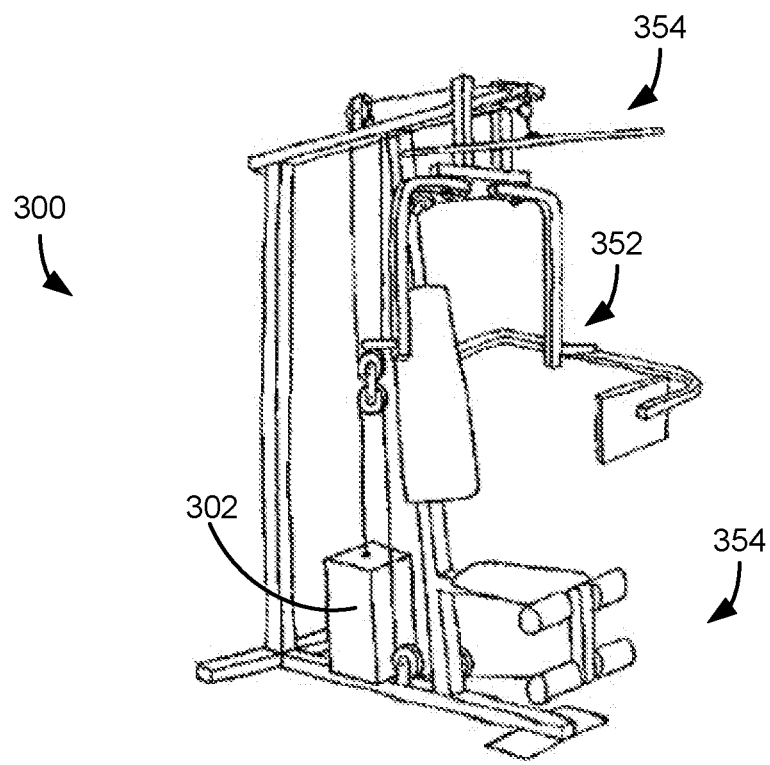
FIG. 3 is a schematic illustration of a third exercise machine including a dynamic force module according to the present disclosure.

Dynamic force modules may also be incorporated into multi-function exercise equipment. For example, FIG. 3 illustrates an exercise machine 300 in the form of a multi-function exercise machine including each of a pull-down mechanism 350, a bench press/pectoral fly mechanism 352, and a leg extension/leg curl mechanism 354. Similar to the exercise machine 100 of FIG. 1, the exercise machine 300 further includes a dynamic force module 302 to provide reactive force to each of the mechanisms 350-354 and in place of a conventional weight stack or similar resistance mechanism. The exercise machine 300 is further illustrated as including a display 356 which may be perform various functions including, without limitation, presenting workout data to a user, controlling parameters of the dynamic force module 302, and presenting motivational or instructional content to the user.

Figure 4:
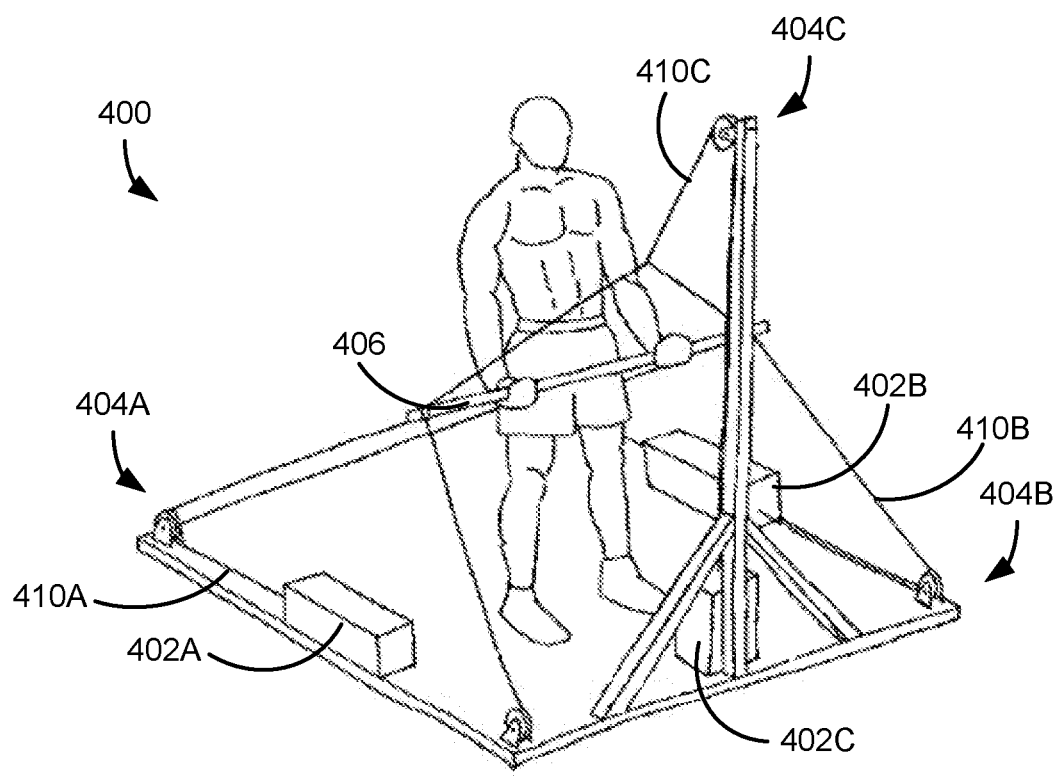
FIG. 4 is a schematic illustration of a fourth exercise machine including three dynamic force modules according to the present disclosure

FIG. 4 is another implementation of an exercise machine 400. The exercise machine 400 includes three dynamic force modules 402A-402O, each of which are coupled to a bar 406 by respective cables 410A-410O and pulleys/transmission mechanisms 404A-404O. As shown, the dynamic force modules 402A, 402B are coupled to opposite ends of the bar 406 to provide downwardly directed force to the bar 406. In contrast, dynamic force module 402C is coupled to the bar 406 to provide upwardly directed force. In one example application, the exercise machine 400 may be configured for performing barbell curls. In such an application, the dynamic force modules 402A-402O may be used to provide reactive force during both the concentric phase (i.e., the lifting phase) of the curl and the eccentric (i.e., the lowering phase) of the curl. More specifically, during the concentric phase, downward force may be provided by each of the dynamic force modules 402A, 402B while during the eccentric phase upward force may be provided by the dynamic force module 402C.

The foregoing examples of exercise machines are intended merely as examples within which dynamic force modules of the present disclosure may be incorporated. More generally, a dynamic force module in accordance with this disclosure may be used in place of most conventional resistance elements including, without limitation, weight stacks, flexible bars or rods, elastic bands or tubes, straps, magnetic resistance elements, air-based resistance mechanisms, and frictional resistance elements. Accordingly, a dynamic force module may generally be implemented into a broad range of exercise machines intended for cardiovascular, strength, and other types of training. Notably, in contrast to such conventional resistance elements, the dynamic force module is able to provide dynamic reactive force that varies based on various parameters including, without limitation, the position of the user, the position of a handle or other accessory handled by the user, the speed with which a movement is being executed, the force applied during an exercise, and other similar metrics.

Figure 5:
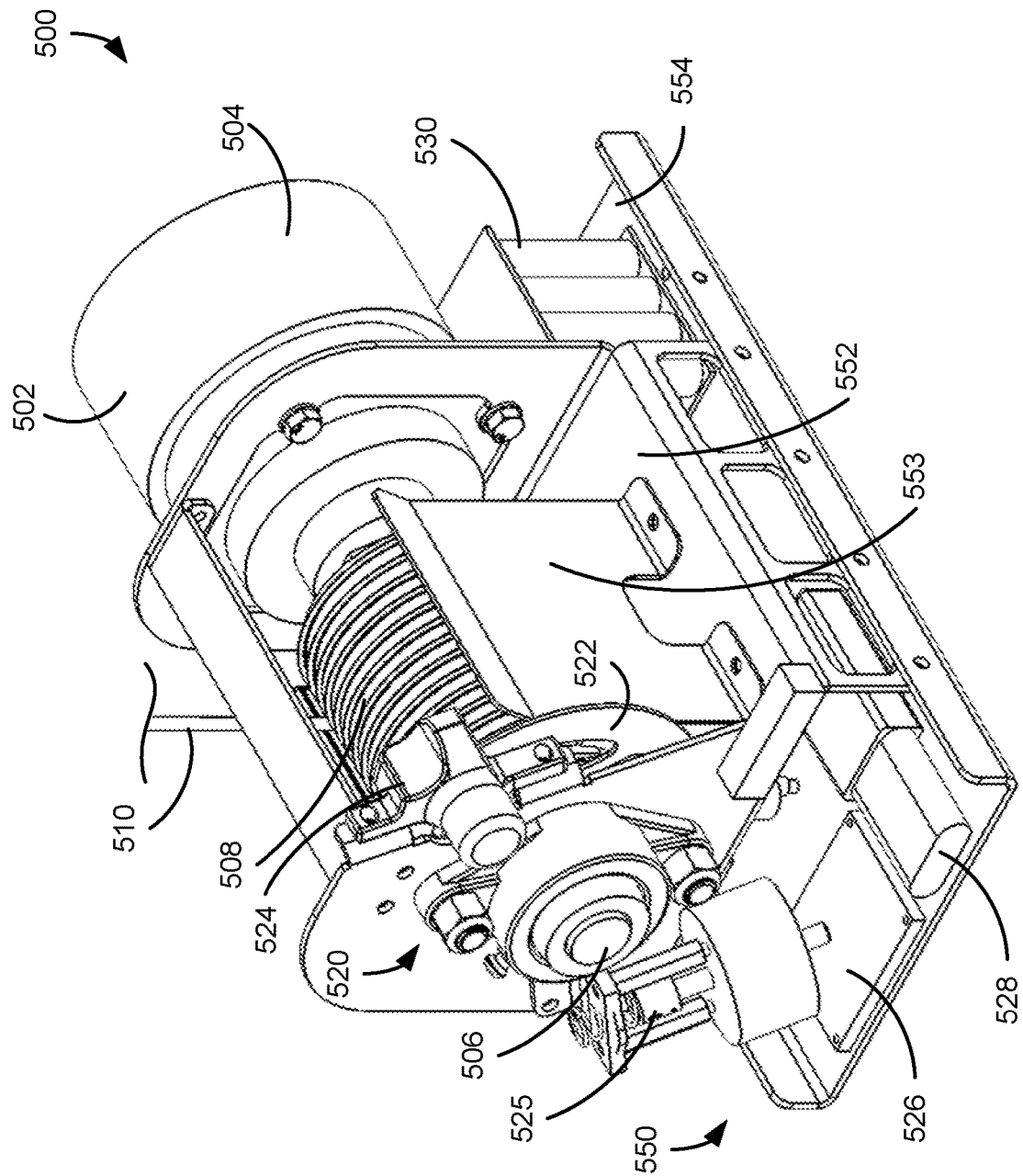
FIG. 5 is an isometric view of a dynamic force module in accordance with the present disclosure.
Figure 6:
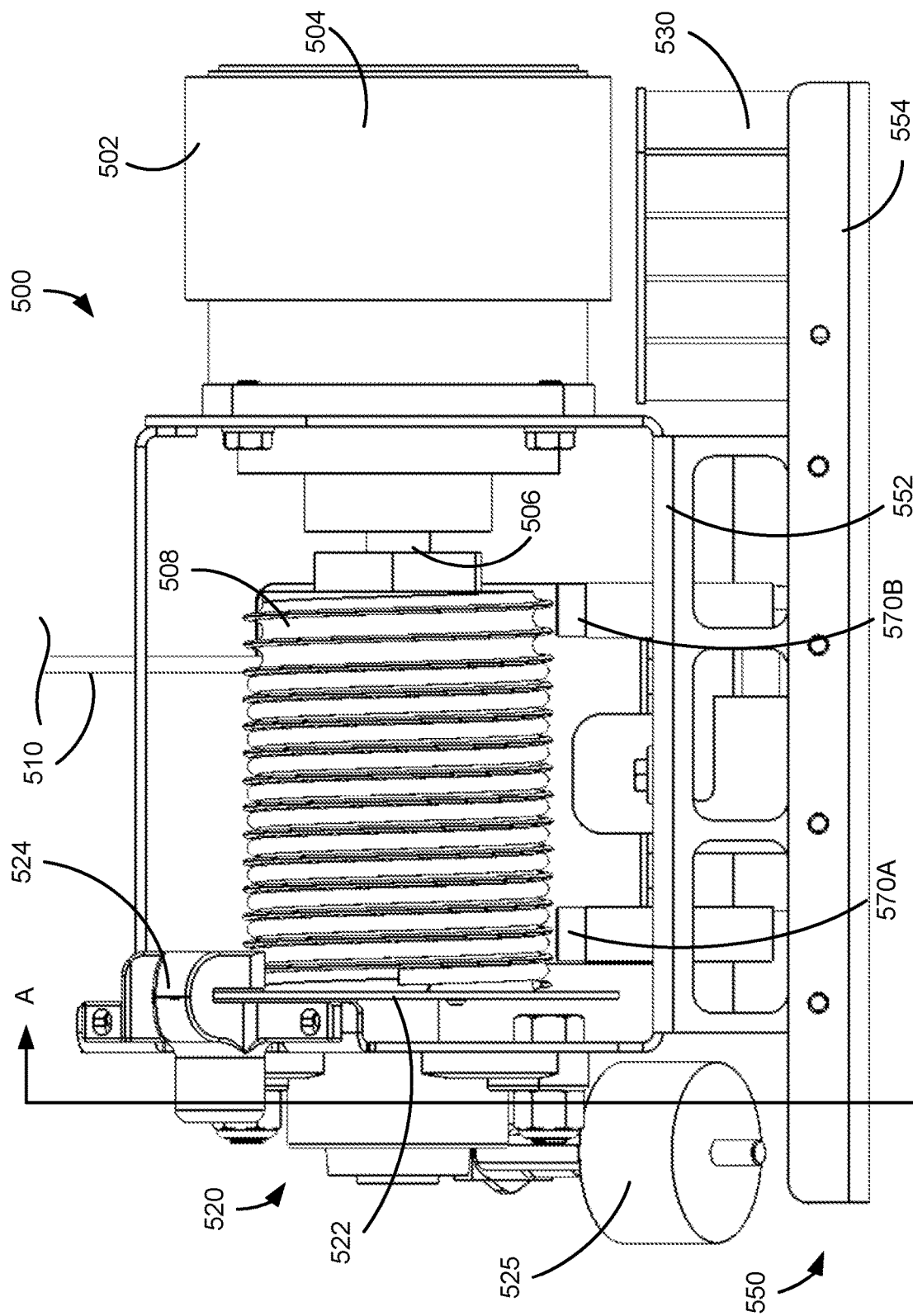
FIG. 6 is a side elevation view of the dynamic force module of FIG. 5.

FIG. 5 is an isometric view of a dynamic force module 500 in accordance with the present disclosure and FIG. 6 is a side elevation view of the dynamic force module 500. Although other configurations of dynamic force modules are contemplated, as illustrated in FIG. 5, the dynamic force module 500 includes a motor 502 mounted on a frame 550 including a motor bracket 552 and a base plate 554 coupled to the motor bracket 552. The motor 502 includes a motor hub 504 and motor shaft 506 extending from the motor hub 504. The motor shaft 506 includes a drum 508 about which a cable 510 is disposed. The motor shaft 506 is supported on one end by the motor hub 504 and on the opposite end by a bearing 512 coupled to the frame 550. In certain implementations, the dynamic force module may further include a brake assembly 520 including a disc 522 coupled to the motor shaft 506 and a caliper 524 mounted on the frame 550. The dynamic force module 500 further includes a brake solenoid 525 for actuation of the brake assembly 520, and power- and control-related electronics including a system controller 526, a motor controller 528, and a battery pack 530. The dynamic force module 500 may further include one or more guards, such as guard 553, or one or more similar structures to restrict movement of the cable 510 during operation. Such guards may include ridges, gussets, lips or similar features for improving structural strength. The guards may also include lips, ridges, bends, guides, or similar features that are shaped to improve retention of the cable 510. For clarity, the guard 553 is removed in FIG. 6.

The dynamic force module 500 may include one or more sensors for determining the extent to which the cable 510 has been unspooled from the drum 508. For example, as shown in FIG. 6, the dynamic force module 500 includes two induction proximity sensors 570A, 570B disposed adjacent the drum 508, although other sensors, switches, etc. may also be used in addition to or instead of induction proximity sensors. For example, in some implementations, one or more of infrared or capacitive sensors may be used instead of the inductive proximity sensors. During operation, the inductive proximity sensors 570A, 570B provides a binary signal based on the presence of the cable 510 (which is metallic or includes metal) at locations on the drum 508 corresponding to the inductive proximity sensors 570A, 570B. Accordingly, based on the signal from the inductive proximity sensors 570A, 570B, the amount of cable 510 remaining on the drum 508 may be determined and, by extension so can the amount of cable 510 that has been unspooled from the drum 508. Alternatively, the inductive proximity sensors 570A, 570B may be positioned relative to the drum 508 to identify specific positions/locations of the cable 510, such as positions corresponding to a home position and an end position of the dynamic force module. Between these extents, internal sensing of the motor 502 (such as from an encoder or similar sensor) may be used to determine the specific degree of extension or retraction of the cable 510.

The inductive proximity sensors 570A, 570B are intended only as an example of a sensor for determining the amount of cable 510 that has been unspooled from the drum 508. In other implementations, the length of unspooled cable 510 or length of cable 510 remaining on the drum 508 may instead be measured based on a number of rotations of the drum 508. Various sensors may be used to obtain such a measurement including, without limitation, potentiometers, accelerometers, Hall Effect sensors, encoders, and resolvers.

Figure 7:
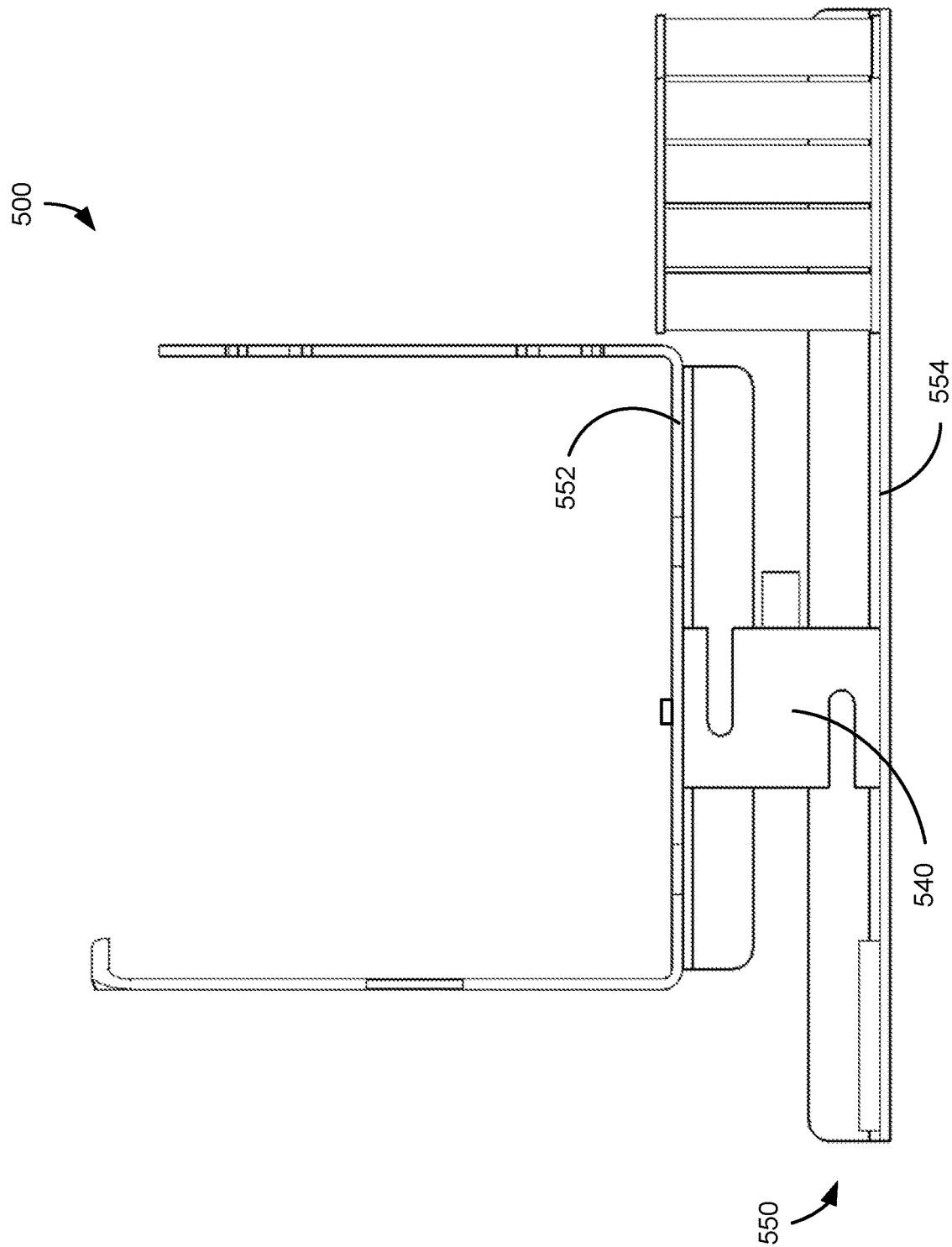
FIG. 7 is a second side elevation view of the dynamic force module of FIG. 5 with certain components of the dynamic force module removed for clarity.

FIG. 7 is a cross-sectional side view of the dynamic force module 500 with the motor 502, brake assembly 520, inductive proximity sensors 570A, 570B and related components removed for clarity. In particular, FIG. 6 is intended to illustrate the arrangement of a load cell 540 of the dynamic force module 500 with respect to the frame 550. The load cell 540 serves as the primary means for measuring force applied to the dynamic force module 500. More specifically, as illustrated in FIG. 6, the motor 502 is coupled to the frame 550 such that as tension on the cable 510 is applied or reduced, a resulting force is applied to the motor bracket 552.

Figure 8:
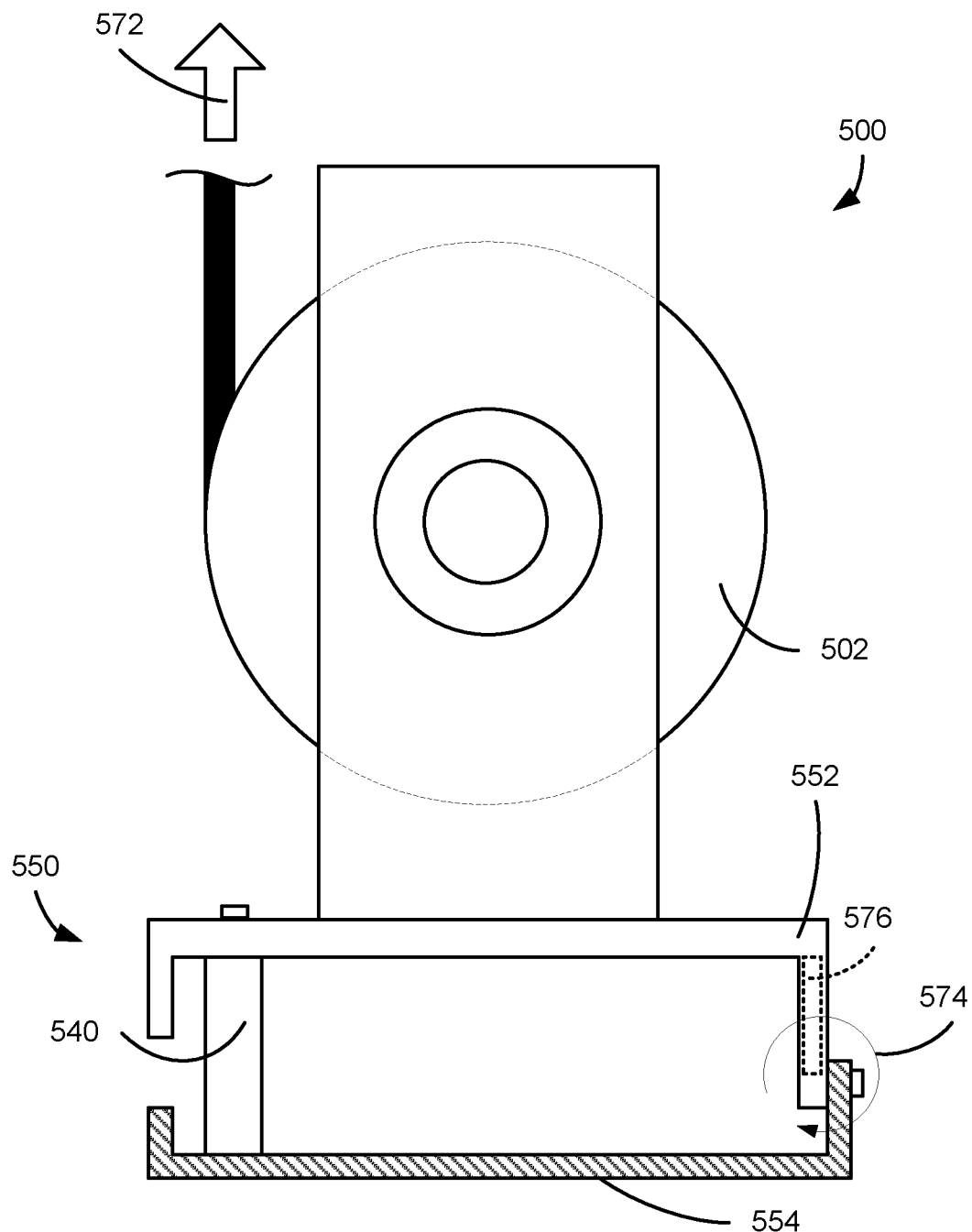
FIG. 8 is a cross-sectional side view of the dynamic force module of FIGS. 5-7.

Referring back to FIG. 7, the load cell 540 is generally coupled to the frame 550 such that the load cell 540 is the primary support for the motor bracket 552 and the motor. In other words, when tension is not applied to the cable 510, the weight of the motor 502 is substantially applied to the load cell 540. As tension on the cable 510 varies during an exercise, the weight on the load cell 540 and the corresponding measurements provided by the load cell 540 vary such that the force applied by the user may be determined. FIG. 8 is a representative side view of the dynamic force module 500 further illustrating the arrangement of the load cell 540. In particular, FIG. 8 is a representative side view of the dynamic force module 500 along cross-section A-A indicated in FIG. 6. As indicated in FIG. 8, the load cell 540 is disposed between the motor bracket 552 and the base plate 554 of the frame 550. Accordingly, as tension is applied to the cable 510 (as indicated by arrow 572), the load applied to the load cell 540 is varied, thereby providing an indication of forces being applied to the cable 510.

FIG. 8 further illustrates the motor bracket 552 being coupled to the base plate 554 of the frame opposite the load cell 540. More generally, the load cell 540 is disposed relative to the coupling between the motor bracket 552 and the base plate 554 such that tension applied to the cable 510 results in a corresponding tension being applied to the load cell 540. In certain arrangement, such as that of FIG. 8, the coupling between the motor bracket 552 and the base plate 554 provides a fulcrum about which the motor bracket 552 rotates (as indicated by arrow 574) in response to tension applied to the cable 510 and provides additional stability for the frame 550. In other words, in certain implementations the motor bracket 552 may be coupled to the base plate 554 such that the motor bracket 552 provides a cantilever supporting the motor 502 that is in turn supported by the load cell 540. To facilitate more accurate measurements by the load cell 540, one or more of the motor bracket 552, the base plate 554, and the coupling therebetween may be adapted to have increased flexibility, thereby reducing the load absorbed by elements of the frame 550 other than the load cell 540. For example, in certain implementations, one or both of the motor bracket 552 and the base plate 554 may include cutouts, thinned sections, or similar sections of flexible material forming living hinges. The motor bracket 552 of the dynamic force module 500, for example, includes cutouts (such as cutout 576) distributed along a side 578 of the motor bracket 552 disposed opposite the load cell 540. Such cutouts increase the flexibility of the coupling between the motor bracket 552 and the base plate 554, thereby improving the sensitivity of the load cell 540 to variations in tension applied to the cable 510. In still other implementations, the motor bracket 552 and the base plate 554 may instead be coupled by one or more movable joints, such as a multi-part hinge.

FIGS. 9A-9F illustrate various alternative dynamic force modules in accordance with the present disclosure and are intended to illustrate various frame designs that may be implemented.

FIG. 9A is a side view of a first alternative dynamic force module 900A taken along a cross-section similar to cross-section A-A shown in FIG. 6. FIG. 9B is a top view of the dynamic force module 900A with certain components removed for clarity. The dynamic force module 900A includes a motor 902A mounted to a frame 950A. More specifically, the motor 902A is coupled to a motor bracket 952A. The motor bracket 952A includes a pair of parallel rails 960A, 962A. Each of the parallel rails 960A, 962A is supported by a base plate 954A of the frame 950A such that tension applied to a cable 910A of the dynamic force module 900A applies force to respective load cells 964A, 966A. More specifically, the rails 960A, 962A are received by respective brackets assemblies 932A, 934A that support the load cells 964A, 966A above the rails 960A, 962A such that as upward tension is applied to the cable 910A, the load cells 964A, 966A are compressed by the rails 960A, 962A, thereby providing a measurement corresponding to the tension applied to the cable 910A. Each of the bracket assemblies 932A, 934A may further include an adjustment member, such as adjustment screws 936A, 938A, for fine tuning the position of the rails 960A, 962A with respect to the load cells 964A, 966A. Notably, in implementations similar to that of FIG. 9A, one of the bracket assemblies 932A, 934A may be omitted and replaced with a floating support such that the motor 902A is constrained only at a single point. By doing so, forces on the motor 902A caused by tension on the cable 910A may be entirely transferred to the remaining load cell, thereby improving the accuracy and sensitivity of the load cell to variations in tension on the cable 910A.

Figure 9D:
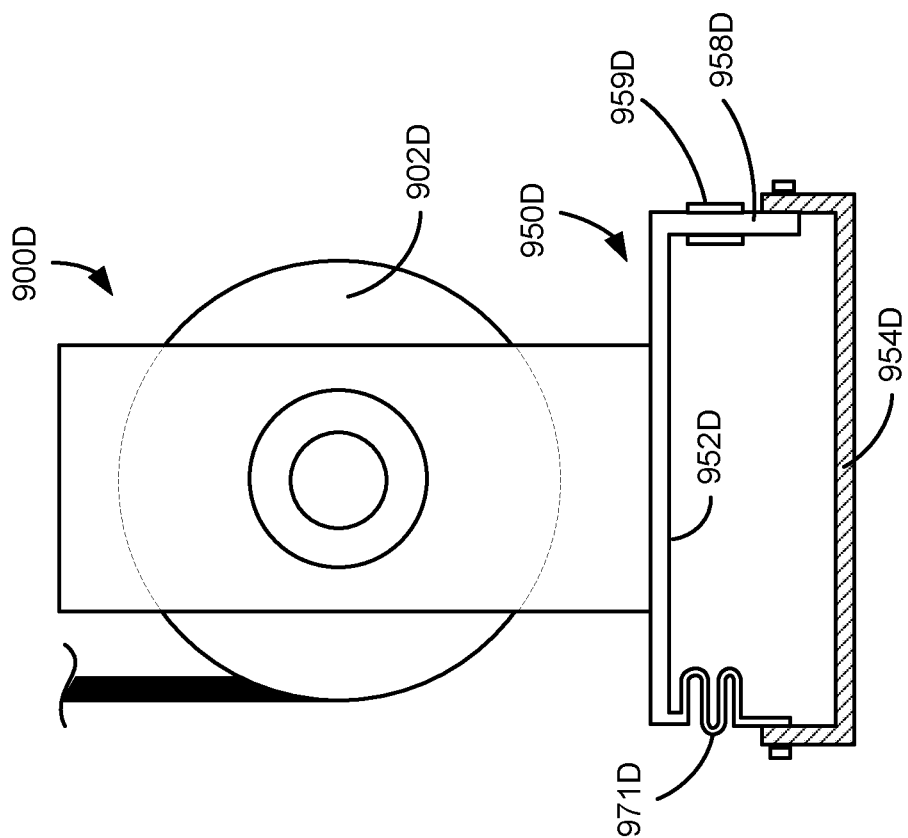
FIG. 9D is a cross-sectional side view of a fourth dynamic force module according to the present disclosure.
Figure 9C:
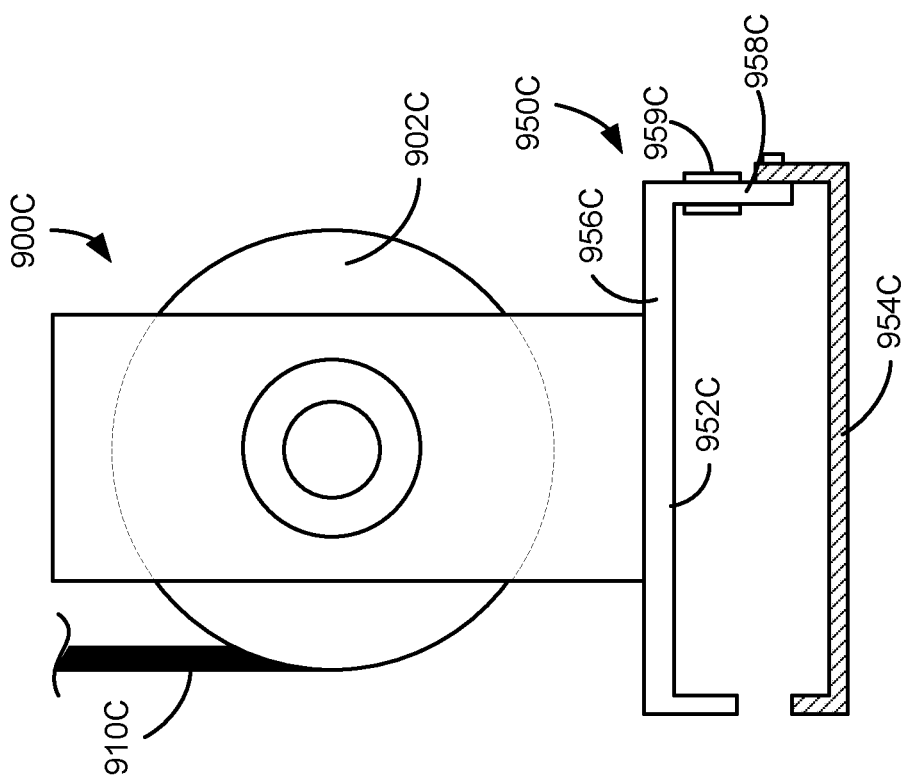
FIG. 9C is a cross-sectional side view of a third dynamic force module according to the present disclosure.

FIG. 9c is a side view of a second alternative dynamic force module 900B taken along a cross-section similar to cross-section A-A shown in FIG. 6. The dynamic force module 900C includes a motor 902C mounted to a frame 950C. Similar to the dynamic force module 500 of FIGS. 5-8, the dynamic force module 900C includes a frame 950C having a motor bracket 952C coupled to a base plate 954C. The motor bracket 952C is coupled to the base plate 954C such that the motor bracket 952C forms a cantilever on which the motor 902C is mounted. More specifically, the motor bracket 952C includes an upper portion 956C to which the motor 902C is coupled and a sidewall 958C extending from the upper portion 956C that is coupled to the base plate 954C. Accordingly, as tension is applied to a cable 910C of the dynamic force module 900C, a load is applied to the sidewall 958C. One or more strain gauges 959C are coupled to the sidewall 958C to measure the loading of the sidewall 958C and, based on such measurements, to determine the tension applied to the cable 910C.

Figure 9F:
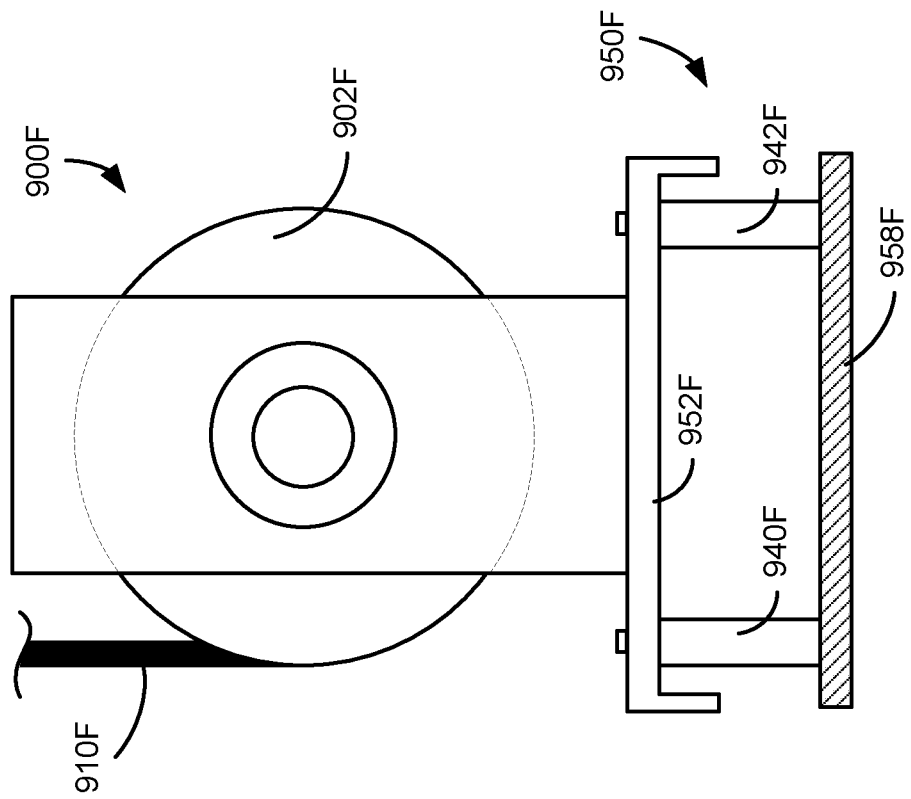
FIG. 9F is a cross-sectional side view of a sixth dynamic force module according to the present disclosure.
Figure 9E:
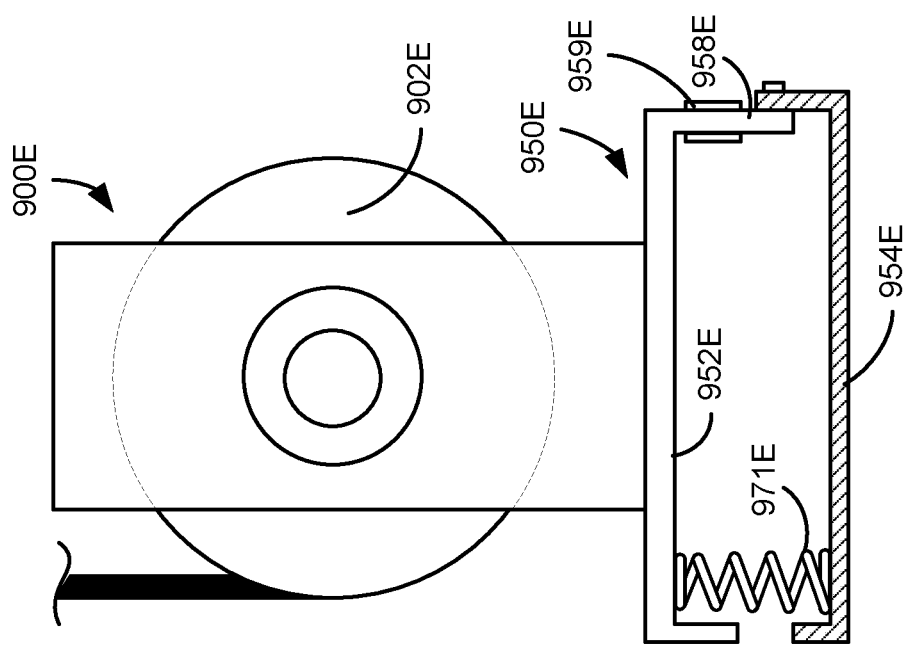
FIG. 9E is a cross-sectional side view of a fifth dynamic force module according to the present disclosure.

FIGS. 9D and 9E are side views of a third alternative dynamic force module 900D and a fourth alternative dynamic force module 900E taken along a cross-section similar to cross-section A-A shown in FIG. 6. The dynamic force modules 900D, 900E are similar to the dynamic force module 900C of FIG. 9C; however, instead of the fully cantilevered motor bracket 952D of the dynamic force module 900D, additional support is provided for the respective motor brackets. The frame 950D of the dynamic force module 900D of FIG. 9D, for example, includes a motor bracket 952D that supports a motor 902D and that is coupled to opposite sides of a base plate 954D. More specifically, the motor bracket 952D includes a first sidewall 958D including a strain gauge 959D. Opposite the first sidewall 958D, the motor bracket 952D includes a second sidewall 971D including an integral spring structure. The dynamic force module 900E of FIG. 9E is also similar to the dynamic force module 900B of FIG. 9B. Specifically, the dynamic force module 900E includes a frame 950E including a motor bracket 952E that supports a motor 902E and that is coupled to a base plate 954E. The motor bracket 952E further includes a sidewall 958E to which a strain gauge 959E is coupled. However, in contrast to the spring structure 971C of the dynamic force module 900C, which is integrated into the motor bracket 952E, the dynamic force module 900E includes a spring 971E disposed between the motor bracket 952E and the base plate 954E.

FIG. 9F is a side view of a sixth alternative dynamic force module 900F. The dynamic force module 900F includes a motor 902F and a frame 950F having each of a motor bracket 952F and a base plate 954F. Disposed between the motor bracket 952F and the base plate 954F are load cells 940F, 942F on which the motor bracket 952F is directly mounted. Accordingly, as tension is applied to a cable 910F of the dynamic force module 900F, a load is applied to each of the load cells 940F, 942F. The measurements provided by each of the load cells 940F, 942F may then be combined to measure the total load applied to the motor 902F and, as a result, the tension applied to the cable 910F. Notably, although illustrated in FIG. 9F as including two load cells 940F, 942F, other implementations of the present disclosure may include any number of load cells. For example, in one implementation, a dynamic force module may include four load cells with one load cell placed in each corner of the frame or similarly distributed between the motor bracket and the base plate of the frame.

Figure 10:
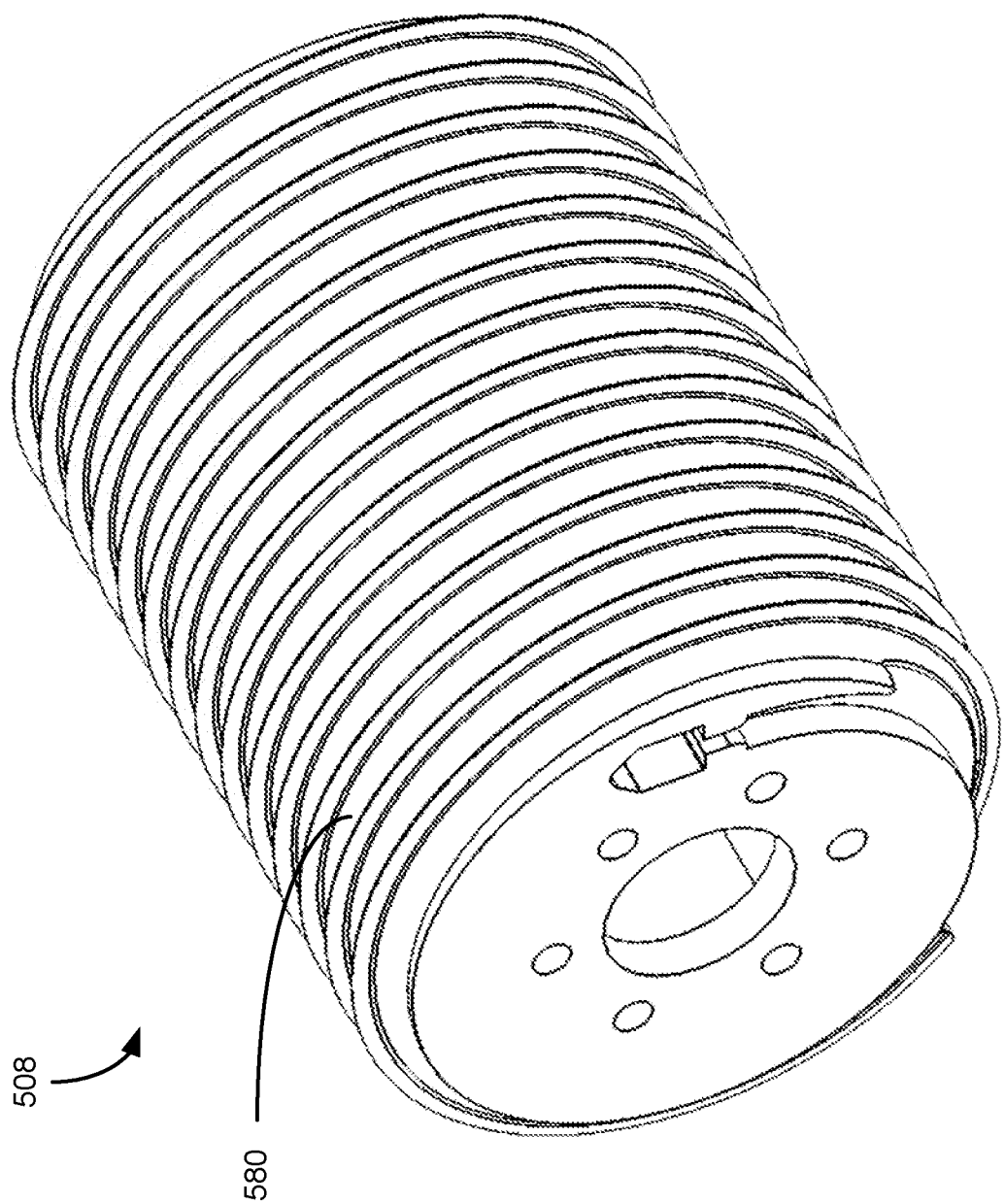
FIG. 10 is an isometric view of a drum of the dynamic force module of FIGS. 5-8.

FIG. 10 is an isometric view of the drum 508 of the dynamic force module 500 as previously included in each of FIGS. 5 and 6. The drum 508 is coupled to the motor shaft 506 of the motor 502 and, as a result, rotates with the motor shaft 506. As illustrated in FIG. 10 and with reference to elements of FIGS. 5 and 6, the drum 508 may include a helical groove 580 extending about and along the length of the drum 508. The groove 580 provides a guide for the cable 510 as the cable 510 is spooled and unspooled from the drum 508 during operation of the dynamic force module 500. More specifically, the groove 508 is arranged to prevent contact and/or overlapping of the cable 510 as it is spooled onto the drum 508 and, as a result, enables unspooling of the cable 510 without binding or friction with itself. For example, the groove 580 may generally have a radius of curvature similar to the radius of the cable 510 such that the cable 510 is cradled by the groove 580. The pitch of the groove 580 may also be chosen to prevent contact between adjacent turns of the cable 510 when the cable 510 is spooled on the drum.

The foregoing discussion provides various details regarding the mechanical aspects of dynamic force modules according to the present disclosure. The following discussion will address the electrical, control, and user interface elements that may be included in dynamic force modules. In general, however, dynamic force modules according to the present disclosure are adapted to provide dynamic reactive force based on a force profile that dictates a relationship between an operational parameter of the dynamic force module and a measured parameter associated with an exercise being performed by a user. For example, in certain implementations, the reactive force provided by the dynamic force module may vary depending on the position, speed, or acceleration applied by the user as measured by various sensors. In another example, the dynamic force module may operate at a nominal reactive force but may then increase or decrease reactive force in response to the user speeding up or slowing down movement, respectively, to encourage the user to perform an exercise at an optimal speed. Other possible control mechanisms are provided in more detail below.

As previously discussed in the context of FIGS. 7-9F, dynamic force modules in accordance with this disclosure generally measure reactive force by a load cell, strain gauge, current sensor, or similar sensor coupled to a frame supporting a motor or similar actuator of the dynamic force module. Other sensors of the dynamic force module may include, without limitation, one or more of an encoder, a potentiometer, a Hall Effect sensor, or similar sensors for counting or otherwise measuring rotations of the motor. As illustrated in FIG. 6, the dynamic force module may also include inductive or other proximity sensors for measuring the presence of the cable on the drum of the dynamic force module. Such measurements may then be converted to determine the length of cable unspooled from the dynamic force module and, as a result, the position, speed, or acceleration of the user.

The position, speed, or acceleration of the user may also be determined using sensors of an exercise machine in which the dynamic force module is incorporated or other sensors in the environment around the dynamic force module. For example, in certain implementations, an exercise machine including a dynamic force module may further include potentiometers, accelerometers, encoders, switches, load cells, strain gauges, pressure pads, and other sensors for determining the position, orientation, speed, acceleration, loading or other parameters of various components of the exercise machine and, as a result, corresponding parameters corresponding to the user. A vision system may also be used to measure similar parameters by tracking and analyzing movement of one or both of the user and the exercise machine.

Dynamic force modules in accordance with the present disclosure may also be communicatively coupleable to a computing device, such as, without limitation, a smartphone, smartwatch, laptop, tablet, exercise tracker, display, server, or similar computing device. Such computing devices may execute or otherwise provide access to an application, web portal, or other software, including those that provide access to data bases and other data sources. Such computing devices generally facilitate interaction between the user and the dynamic force module by enabling the user to provide commands, settings, and similar input to the dynamic force module and for the dynamic force module to provide information and feedback to the user. For example, in certain implementations, the computing device may include a display that enables a user to select from a variety of workouts or to otherwise change settings of the exercise machine and dynamic force module. During a workout the dynamic force module may communicate with the computing device such that the computing device displays, among other things, the current settings of the dynamic force module, the user's progress through an exercise or workout, and other information.

During an exercise or broader workout, one or more of the dynamic force module, the exercise machine in which the dynamic force module is incorporated, and a computing device communicatively coupled to the dynamic force module and/or the exercise machine may be adapted to provide feedback to a user. Such feedback may be used, for example, to provide encouragement to the user or to provide guidance on form and technique for performing an exercise. For example, the speed with which the user executes a particular movement may be tracked and various forms of audio, visual, or haptic feedback may be provided the user based on whether and to what degree the user's speed deviates from a predetermined optimal speed or speed range. In certain implementations, the frequency, intensity, or other parameter of the feedback may be varied in response to the user's deviation from an optimal value or range.

In certain implementations, dynamic force modules in accordance with this disclosure provide such feedback, at least in part, through a user interface that is presented to the user. The user interface generally includes textual, audio, speech, and/or graphical elements for guiding the user through exercises or workouts. For example, the user interface may include animated graphs or other representations for displaying a measured user parameter relative to an optimal value or optimal range for the same parameter. As the user performance a given exercise, a marker or similar representation associated with the user parameter may move to indicate the user parameter, thereby providing the user with feedback regarding the quality with which the user is performing the exercise. The user interface may also indicate, among other things, a user's progress through an exercise or workout, a score or points accumulated by the user based on successful completion of an exercise or exercises, and similar information.

Figure 11:
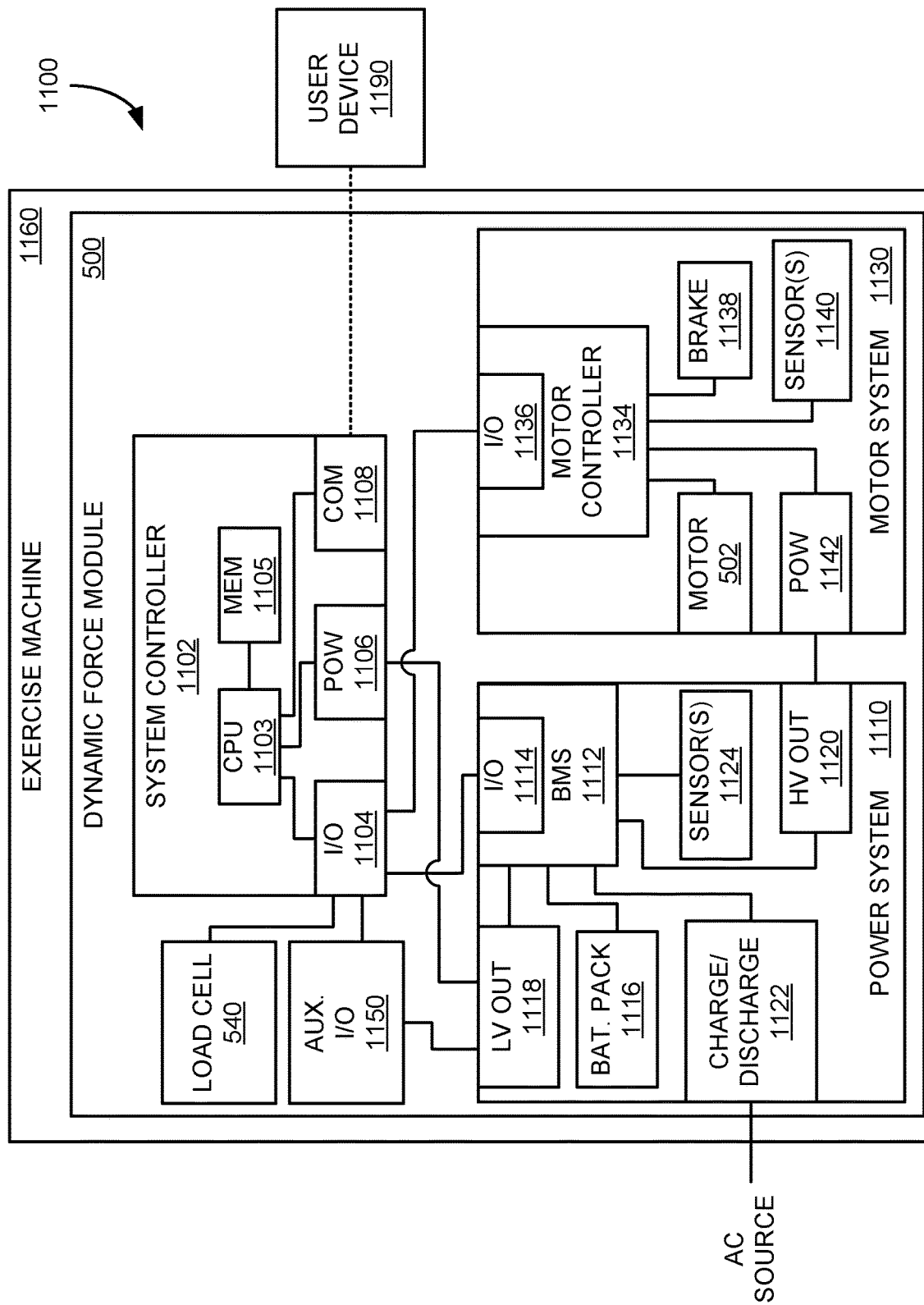
FIG. 11 is a block diagram illustrating a system including the dynamic force module of FIGS. 5-8.

Further aspects of the dynamic force module are now provided in detail with reference to FIG. 11, which is a block diagram illustrating a system 1100 in which the dynamic force module 500 of FIG. 5 is incorporated into an exercise machine 1160. In general, the dynamic force module 500 includes a system controller 1102 for providing primary control and supervision of the dynamic force module 500 and each of a dynamic force module power system 1110 and a motor system 1130 communicatively coupled to the system controller 1102. As described below in more detail, the dynamic force module power system 1110 facilitates charging, discharging, and distribution of power for the dynamic force module 500 while the motor system 1130 provides control and supervision of the motor 502. The system controller 1102 is also illustrated as being communicatively coupled to a load cell 540, for providing readings associated with forces applied to the dynamic force module 500 during performance of an exercise by a user.

The system controller 1102, includes a processor 1103 communicatively coupled to a memory 1105. Although other configurations of the system control 1102 are possible, in general, the memory 1105 stores data and instructions executable by the processor 1103 to perform functions of the dynamic force module 500. The system controller 1102 may further include each of an input/output (I/O) module 1104, a power module 1106, and a communications module 1108.

During operation, the system controller 1102 may send and receive signals via the I/O module 1104. In particular, the system controller 1102 may receive readings and data from the load cell 540, the dynamic force module power system 1110, the motor system 1130, and/or other sensors of the system 1100 and provide commands to direct various functions of the dynamic force module 500. For example, the system controller 1102 may provide commands to the motor system 1130 for positioning or otherwise controlling the motor 502 in response to force readings provided by the load cell 540 during execution of an exercise by a user. The motor system 1130 may in turn provide sensor readings corresponding to the position and movement of the motor 502, thereby providing feedback to the system controller 1102 and based on which the system controller 1102 may issue additional commands to components of the dynamic force module 500.

The I/O module 1104 may also be configured to send to and/or receive data from one or more auxiliary inputs and outputs 1150 of the dynamic force module 500 or the exercise machine 1160 to which the dynamic force module 500 is connected. Such auxiliary I/O 1150 may be used, for example, to provide feedback to the user or to indicate the status of the dynamic force module 500. Regarding feedback, the auxiliary I/O may include, without limitation, one or more of a speaker, lights/LEDs, a display, a haptic feedback system, a counter, or any similar device that may be used to indicate various information regarding an exercise or workout to a user. Such information may include, without limitation, current force settings of the dynamic force module 500, progress of the user (e.g., a counter or progress bar), whether the user has performed a particular exercise properly, and the like. The auxiliary I/O 1150 may also be used to indicate the operational status of the dynamic force module 500. For example, the auxiliary I/O 1150 may include a display or indicator lights for indicating whether the dynamic force module 500 is currently on and whether the dynamic force module 500 is functioning properly or in an error state.

The auxiliary I/O 1150 may also include one or more actuators of the exercise machine 1160. For example, in certain implementations, the exercise machine 1160 may include one or more actuators for modifying the configuration of the exercise machine 1160. Such actuators may, for example, adjust the location and placement of handles or linkages such that the exercise machine may be used for different exercises or to accommodate the physical characteristics of different users.

In certain implementations, the auxiliary I/O 1150 may also include various sensors and systems for measuring the position of the user and/or other components of the exercise machine 1160 or the dynamic force module 500. For example, in addition to the load cell 540 of the dynamic force module 500, the auxiliary I/O 1150 may also include one or more additional force sensors, such as a strain gauge, incorporated into the dynamic force module 500 or coupled to an element of the exercise machine 1160 to measure the amount of force exerted by a user. Such sensors may be placed, for example, in line with a cable, at a motor shaft, on a pulley, in a handle, or in linkages or joints of the exercise machine 1160. The auxiliary I/O 1150 may also include a position sensor for measuring the position of the user and/or the position of components of the dynamic force module 500 or the exercise machine 1160. Positions sensors may include, without limitation, one or more of an encoder, a potentiometer, an accelerometer, and a computer vision system. For example, in certain implementations, a potentiometer or encoder may be mounted internally near the motor 502 of the dynamic force module 500 or incorporated into linkages or elements of the exercise machine 1160 and an accelerometer may be disposed within a handle or grip. In implementations in which a vision system is used, such a system may include one or more externally mounted image capture devices that provide a partial or full three-dimensional view of the user during execution of an exercise.

The auxiliary I/O 1150 may also include various other sensors incorporated into the dynamic force module 500 and the exercise machine 1160. For example, in certain implementations, pressure sensors, capacitive pads, mechanical switches, or similar components may be integrated into a seat of handles of the exercise machine 1160. If the user subsequently stands from the seat or releases the handles, the dynamic force module 500 may automatically return to a safe state or otherwise modify the reactive force provided by the dynamic force module 500.

The system controller 1102 may further include a communications module (COM) 1108 to facilitate communication between the dynamic force module 500 and external devices. The communications module 1108 may, for example, enable wired or wireless communication between the dynamic force module 500 and one or more user computing devices 1190. Such communication may occur over any known protocol including, without limitation, Bluetooth, WiFi, and ANT/ANT+. Accordingly, the user computing device 1190 may be, without limitation, one or more of a smartphone, a tablet, a laptop, a desktop computer, one or more other dynamic force modules, a centralized network node, a user-interface display (such as a user-interface display of the exercise machine 1160), an Internet of Things (IoT) device, a wearable device (such as a smart watch or exercise tracker), an implanted or similar medical device, or any other similar piece of personal computing hardware.

The communications module 1108 may, in certain implementations, be connected to a network, such as the Internet, and enable downloading of various files and instructions for execution by the system controller 1102. For example, in certain implementations, files including force profiles for controlling the dynamic force module 500, exercise routines containing predetermined exercise/force settings, and similar workout information may be downloaded via the communications module 1108 for execution by the dynamic force module 500. Accordingly, a user may search for and locate exercise programs that they would like to perform over the Internet or an application using the user computing device 1190 and cause such programs to be downloaded to and executed by the system controller 1102 of the dynamic force module 500.

In certain implementations, the system controller 1102 may be adapted to automatically download updates to a workout program or exercise in response to user performance or other feedback obtained from the user. In certain implementations, such updating may occur in real-time during the course of an exercise, a set, or a workout. For example, the system controller 1102 may determine that the user is failing or struggling to perform a particular exercise. In response, the system controller 1102 may download and implement an alternative exercise routine or force profile that is more appropriate for the user.

In addition to information regarding particular exercises, the communications module 1108 may also enable downloading of user profile data. Such data may include, among other things, physical characteristics of the user, goals and targets of the user, particular injuries or disabilities the user may be subject to, and any other information that may determine the types, nature, and extent of the exercises for the user. In certain cases, the physical characteristics of the user may be used, at least in part, to automatically configure the exercise machine 1160. For example, in response to receiving user profile data indicating a user's height, body proportions, or similar biometric data, the dynamic force module 500 may automatically adjust the exercise machine 1160 for a proper fit with the user. Such auto configuration may include, among other things, the system controller 1102 communicating and issuing commands to one or more actuators of the exercise machine 1160, as previously discussed in the context of the auxiliary I/O 1150 component of the dynamic force module 500.

The power system 1110 includes a battery management system 1112, a battery pack 1116, a low-voltage output (LV OUT) 1118, a high voltage output (HV OUT) 1120, a charge/discharge system 1122, and various power system-related sensors 1124. The battery management system 1112 may generally function as a controller for the power system 1110 and may include a battery I/O module 1114 adapted to facilitate communication between the battery management system 1112 and the system controller 1102. Accordingly, during operation, the battery management system 1112 may exchange data with the system controller 1102 to facilitate control and operation of the power system 1120.

The charge/discharge system 1122 includes components configured to charge the battery pack 1116 and/or provide for safe discharge of components of the dynamic force module 500, such as during powering off of the dynamic force module 500. In certain implementations, for example, the charge/discharge system 1122 may be adapted to be connected to a standard 120 VAC or similar power source and may include a trickle charger or similar device for providing current to and charging the battery pack 1116 while also providing power to the other components of the dynamic force module 500. The charge/discharge system 1122 may also include a discharge resistor connected to ground to facilitate discharge of dynamic force module components when components of the dynamic force module 500 or the dynamic force module 500 as a whole is turned off or otherwise disabled. Alternatively, other actuators (such as the motor or solenoids of the dynamic force module) may be used in place of the discharge resistor to discharge components of the dynamic force module. In certain implementations, the charge/discharge system 112 may allow charging and discharging of the battery pack such that the state of charge of the battery is maintained at a precise value or percentage corresponding to the expected charge or discharge associated with The power system-related sensors 1124 may include various sensors adapted to measure properties and provide feedback regarding the power system 1110. Such sensors may include, without limitation, one or more of voltage sensors, current sensors, temperature sensors, and sensors specifically adapted to provide an indication of the available power stored within the battery pack 1116. Such sensors may provide data to facilitate power management by the dynamic force module 500. For example, in certain implementations, operation of the dynamic force module 500 may be dictated, at least in part, by power management concerns. For example, in certain implementations, the dynamic force module 500 may include an onboard energy storage system (such as the battery pack 1116). Such implementations may enable use of the dynamic force module 500 without being directly connected to a wall socket or other power source. Such implementations may also include a system for power regeneration (such as a regenerative braking system) adapted to produce power in response to exercises performed by a user, thereby reducing power drawn by the dynamic force module 500 during operation. Accordingly, the system controller 1102 may execute algorithms for predicting the energy consumed and/or generated by each motion of the user and may control corresponding charging and/or discharging of the energy storage system to an appropriate level for the given activity. To the extent excess energy is produced by the user, the power system 1110 may also be adapted to return such excess power to the grid or a secondary storage system, or to dissipate the excess energy as heat. The excess energy may also be used to power other devices and systems, including, without limitation, computing devices adapted to perform cryptographic hashing or other functions for mining cryptocurrencies. Such functionality allows the energy storage system to be generally smaller and to be prepared for the energy loads produced and/or demanded by user activity.

The motor system 1130 includes the motor 502, a motor controller 1134, a motor braking system 1138, and various motor-related sensors 1140. The motor controller 1134 may further include an I/O module 1136 adapted to send and/or receive data from the system controller 1102.

During operation, the motor controller 1134 receives command signals from the system controller 1102 and controls operation of the motor 502 accordingly. Feedback regarding the functioning of the motor 502 may be provided by various sensors 1140 communicatively coupled to the motor controller 1134. Such sensors may include, without limitation, one or more of encoders, potentiometers, resolvers, temperature sensors, voltage and/or current sensors, tachometers, Hall Effect sensors, torque sensors, strain gauges, and any other sensor that may be used to monitor characteristics of the motor 502 and its performance. As previously discussed in more detail in the context of FIG. 5-8, the dynamic force module 500 may also include one or more sensors, such as inductive proximity sensors, adapted to measure the amount of cable being spooled and unspooled from a drum 508 coupled to the motor 502. In such implementations, signals from such sensors may also be transmitted to the system controller 1102 to facilitate control and monitoring of the motor 502.

The motor system 1130 may also include a brake system 1138. For example, the brake system 1138 may include the brake assembly 520 and any associated switches for activating the caliper 524 of the brake assembly 520. Although illustrated in FIG. 11 as being incorporated into the motor system 1130 and controlled through the motor controller 1134, the brake system 1138 may also be separate from the motor system 1130 and controlled directly by the system controller 1102 such that the system controller 1102 may operate the brake assembly in the event of a failure of the motor controller 1134 or other aspects of the motor system 1130. Although described herein as including mechanical brake components, the brake system 1138 may be software driven and provide braking force on the motor through, among other things, DC injection braking and dynamic braking.

The motor system 1130 is also illustrated as including a motor power system 1142 coupled to the broader dynamic force module power system 1110. The motor power system 1142 is generally configured to receive power from the dynamic force module power system 1110 and to provide power to both the motor 502 and the motor controller 1134. Accordingly, the motor power system 1142 may include, among other things, one or more of converters, inverters, transformers, filters and similar components for processing and conditioning power received by the motor system 1130. To the extent such components are actively controlled, such control may, in some implementations, be performed by the motor controller 1134.

Figure 12:
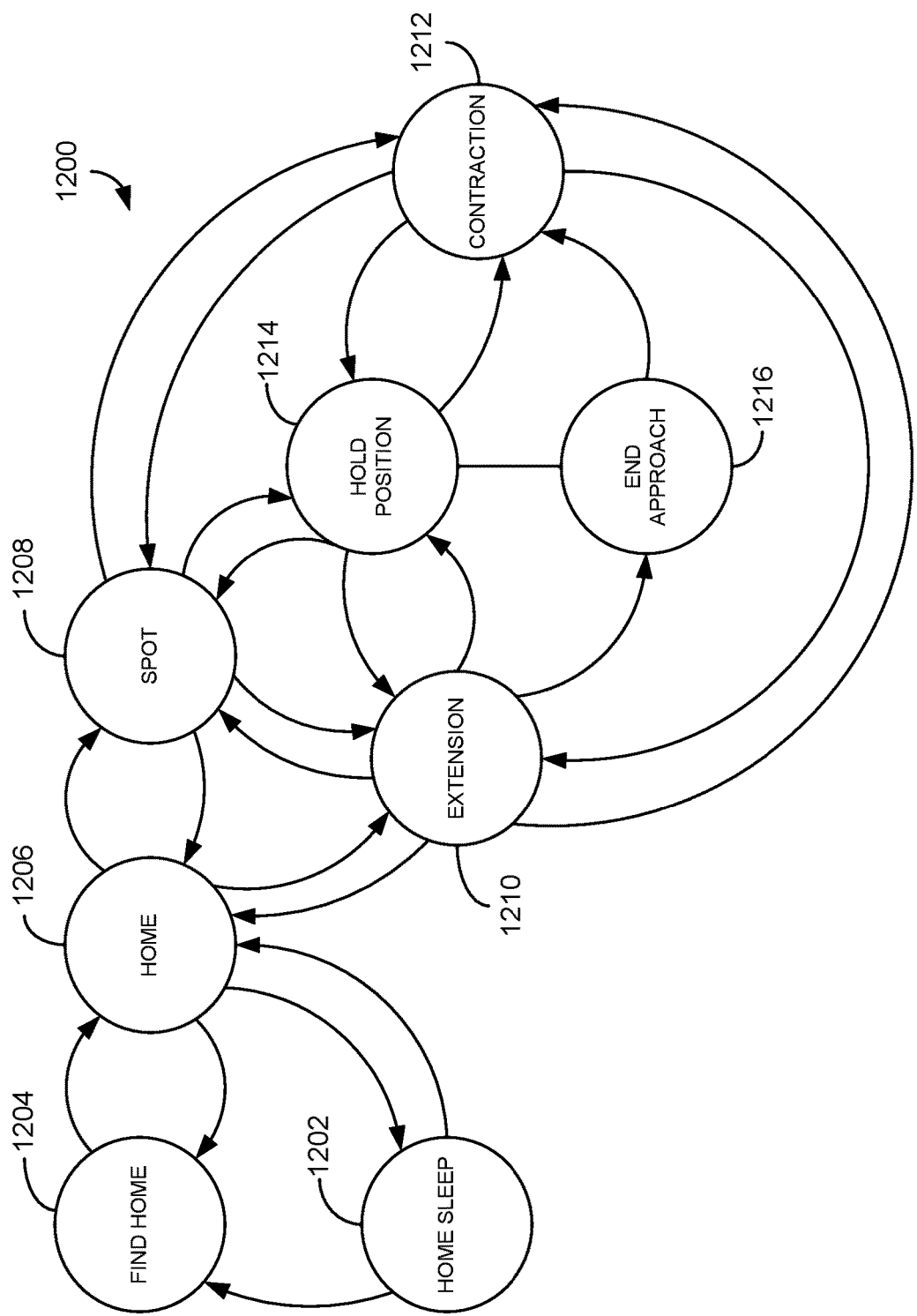
FIG. 12 is a state diagram illustrating operation of an example dynamic force module in accordance with the present disclosure.

FIG. 12 is a state diagram 1200 illustrating operation of an example dynamic force module in accordance with the present disclosure.

The Home Sleep state 1202 generally corresponds to a "sleep" or "off state" of the dynamic force module. While in the Home Sleep state, the dynamic force module is in an inactivated or resting state until turned on or otherwise directed to wake from the Home Sleep state 1202. Such waking may be conducted in response to various events including, without limitation, a user activating a switch or otherwise issuing a command, a user entering into proximity to the dynamic force module, a user gripping or otherwise manipulating a component of the dynamic force module, or a user taking any similar action.

Once activated/woken from the Home Sleep state 1202, the dynamic force module enters the Find Home state 1204. While in the Find Home state 1204, the dynamic force module performs an auto-calibration function in which the dynamic force module determines an absolute home or zero position. In certain implementations, the dynamic force module or exercise machine in which the dynamic force module is incorporated may include limit switches or other positional sensors to assist in determining the home position. For example, the dynamic force module may determine its range extents by actuating in a first direction until a first limit switch is activated and then actuating in an opposite direction until a second limit switch is activated, thereby determining the full range of motion for the dynamic force module. The dynamic force module may then actuate into an intermediate position between the two extents. Alternatively, the dynamic force module may actuate in a first direction until the first limit switch is triggered. The location at which the first limit switch is triggered may then be used as an absolute location from which all subsequent position calculations may be based. The inductive proximity sensors 570A, 570B of FIG. 6 may provide similar functionality as the first and second limit switches. After executing the auto-calibration function associated with the Find Home state 1204, the dynamic force module enters into the Home state 1206 in which the dynamic force module waits in the home position until the dynamic force module receives an input or signal to transition into various exercise-related states.

The exercise-related states generally correspond to providing dynamic resistance during a range of motion associated with an exercise. As illustrated in FIG. 12, for example, the exercise-related states may generally include each of an Extension state 1210 and a Contraction state 1212. The Extension state 1210 and the Contraction state 1212 each generally correspond to halves of an exercise repetition and include application of reactive force by the actuator of the dynamic force module in an appropriate direction. Accordingly, during normal operation, the dynamic force module will generally move between the Extension state 1210 and the Contraction state 1212 as a user performs a repetition. For example, if the dynamic force module were used in conjunction with an exercise machine for performing cable pulls, the dynamic force module would first be in the Extension state 1210 during pulling or extension of the cable from the dynamic force module and then, after sufficient extension, would enter the Contraction state 1212 during retraction of the cable. The specific transitions between the Extension state 1210 and the Contraction state 1212 may vary based on the exercise being performed. Nevertheless, in each of the Extension state 1210 and the Contraction state 1212 the actuator of the dynamic force module provides reactive force according to a force profile that dictates reactive force based on, among other things, position, speed, counter force, or other factors. Example force profiles are discussed in more detail below in the context of FIGS. 13-19.

During an exercise, the dynamic force module may also enter into a Hold Position state 1214. The Hold Position state 1214 generally includes the dynamic force module holding a force, thereby facilitating isometric exercises in which a user holds a position under load. The Hold Position state 1214 may also be used as an emergency state should an error occur during operation. In some implementations, the Hold Position state 1214 includes applying a mechanical or other braking system to maintain the force applied by the dynamic force module actuator.

The dynamic force module may also include a Spot state 1208 in which the dynamic force module is gently returned to the home position. Transition between the Extension state 1210 or the Contraction state 1212 and the Spot state 1208 may occur in response to the dynamic force module detecting that a user is not providing sufficient counter force to complete a repetition. Accordingly, by gently returning the dynamic force module to the home position or by lessening the applied reactive force, the dynamic force module assists the user in completing the current repetition and/or safely returning to the home position.

The dynamic force module may also include states corresponding to operational limits of the dynamic force module. For example, as shown in FIG. 12, the dynamic force module may enter an End Approach state 1216 when at or near a limit of the dynamic force module's range of motion. When in the End Approach state 1216, the dynamic force module may increase the reactive force applied to further movement so as to discourage the dynamic force module from reaching its mechanical limit. In certain implementations, should further extension occur, the dynamic force module may transition into the Hold Position state 1214 in which a brake is applied to prevent further extension.

Dynamic force modules in accordance with the present disclosure may function based on what are referred to herein as force profiles. Force profiles are relationships and/or algorithms that dictate or otherwise control the dynamic force module actuator in response to various parameters as exercises are being performed by a user. In certain implementations, for example, a force profile may dictate the force to be applied by the dynamic force module in response to the position of the user.

Figure 13:
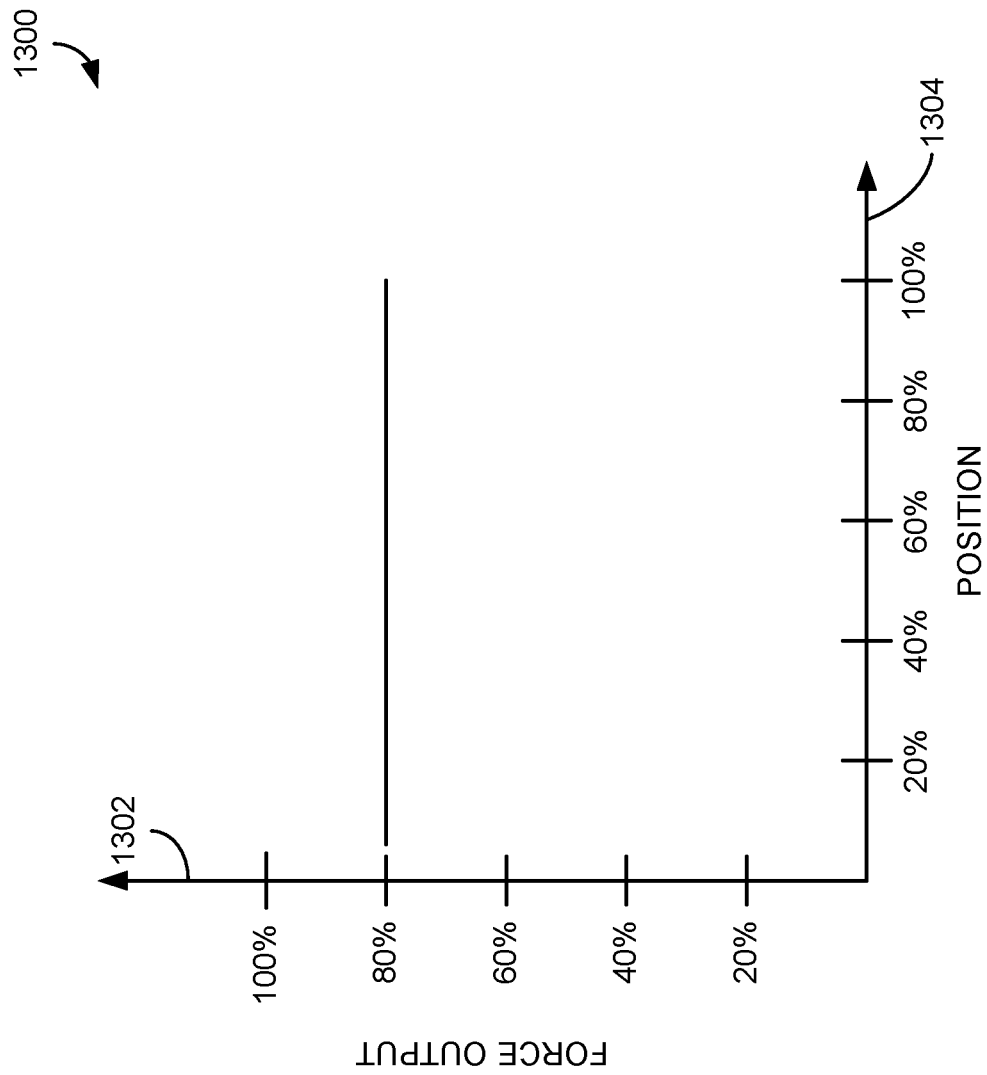
FIG. 13 is a first force profile that may be executed by a dynamic force module, the first force profile including a constant reactive force.

In certain implementations, a force profile may be executed by the dynamic force module that causes the dynamic force module to apply a constant force over a full range of motion associated with an exercise. FIG. 13, for example, is a first force profile 1300 that may be executed by a dynamic force module in accordance with this disclosure. As illustrated by the force profile 1300, certain force profiles in accordance with the present disclosure may provide a relationship between the output force of the dynamic force module 1302 and a position 1304. In certain implementations, each of the force output and the position may be expressed as a percentage of a nominal value. For example, the force output may be indicated as a percentage of some maximum force output that may or may not be equal to the maximum force output of the dynamic force module. Similarly, the position may be expressed as a percentage of a predetermined range of the dynamic force module. The range may be equal to the full range of the dynamic force module (e.g., the full range between full retraction and full extension of the dynamic force module) or may correspond to a range of motion associated with a particular exercise. With respect to the latter, the range of motion may be determined, for example, by having the user perform an exercise under a nominal load, determining the starting and ending position of the user and the corresponding position of the dynamic force module actuator, and setting the position range based on the dynamic force module actuator positions. Although the example of the subsequent figures is based on percentages relative to various nominal values, force profiles may also be implemented based on absolute parameter values. Referring back to FIG. 13, the force profile 1300 presented is a relatively simple force profile in which the force output by the dynamic force module is constant. Specifically, the force output of the dynamic force module is approximately 80% of a maximum force for the full range of positions.

Figure 14:
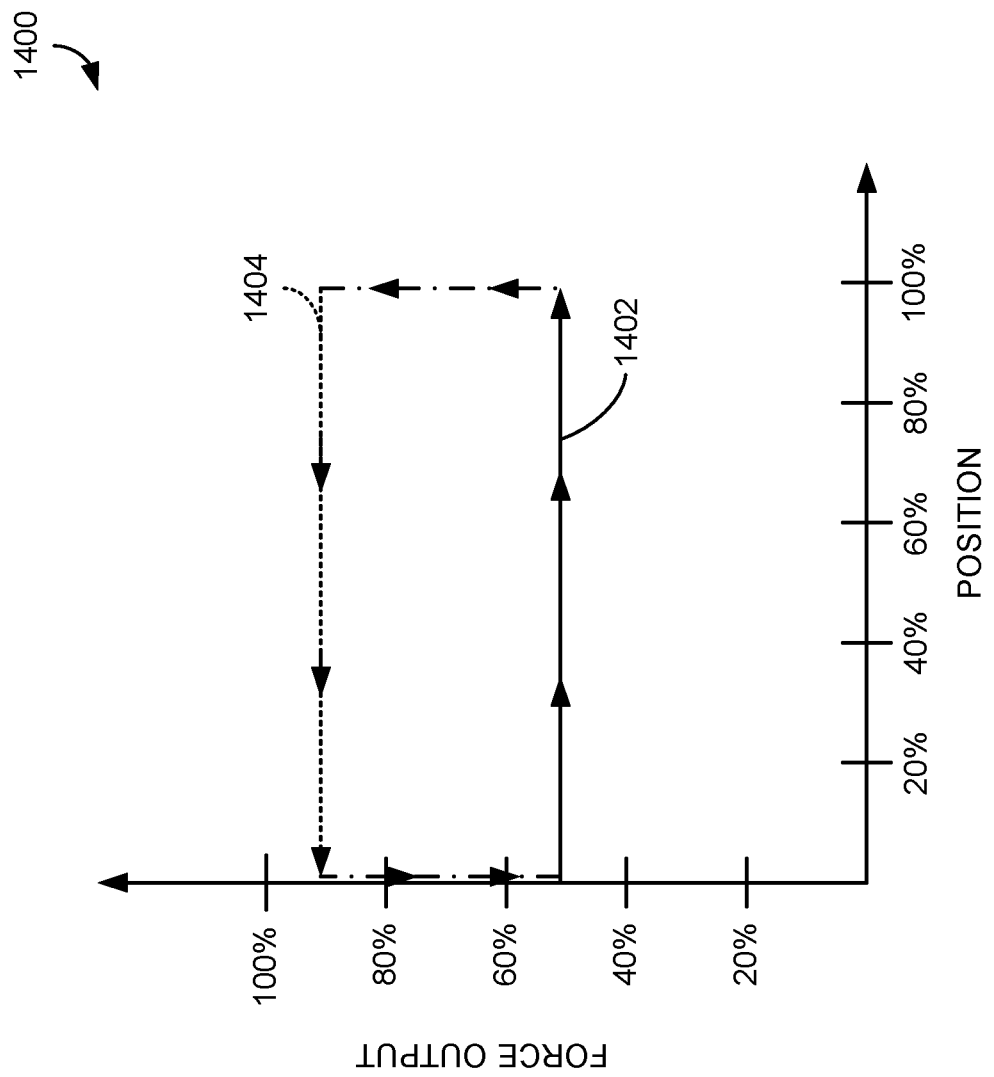
FIG. 14 is a second force profile that may be executed by a dynamic force module, the second force profile illustrating variable concentric and eccentric reactive forces.

Other force profiles may distinguish between phases of an exercise or movement in different directions and apply different reactive forces to each phase or direction of movement. Such force profiles may be used for, among other things, placing additional emphasis on one of the concentric or eccentric portions of an exercise. FIG. 14, for example, is a second force profile 1400 in which different loading is applied during each of the concentric and eccentric phases of an exercise. Such variation may be used, for example, to implement "eccentric overloading" or similar techniques which are generally unavailable using conventional weights or weight-based exercise machines. In the specific force profile 1400 of FIG. 14, for example, a first force is applied by the dynamic force module during a concentric phase 1402 of an exercise at approximately 50% of a predetermined maximum force. However, during the eccentric phase, the force applied by the dynamic force module is increased to approximately 90% of the maximum force. Accordingly, an overload is applied during the eccentric phase. In other implementations, a similar force profile may be used to emphasize the concentric phase of an exercise over the eccentric phase. For example, the force applied by the dynamic force module may be 90% during the concentric phase but then reduced to 50% during the eccentric phase.

Figure 15:
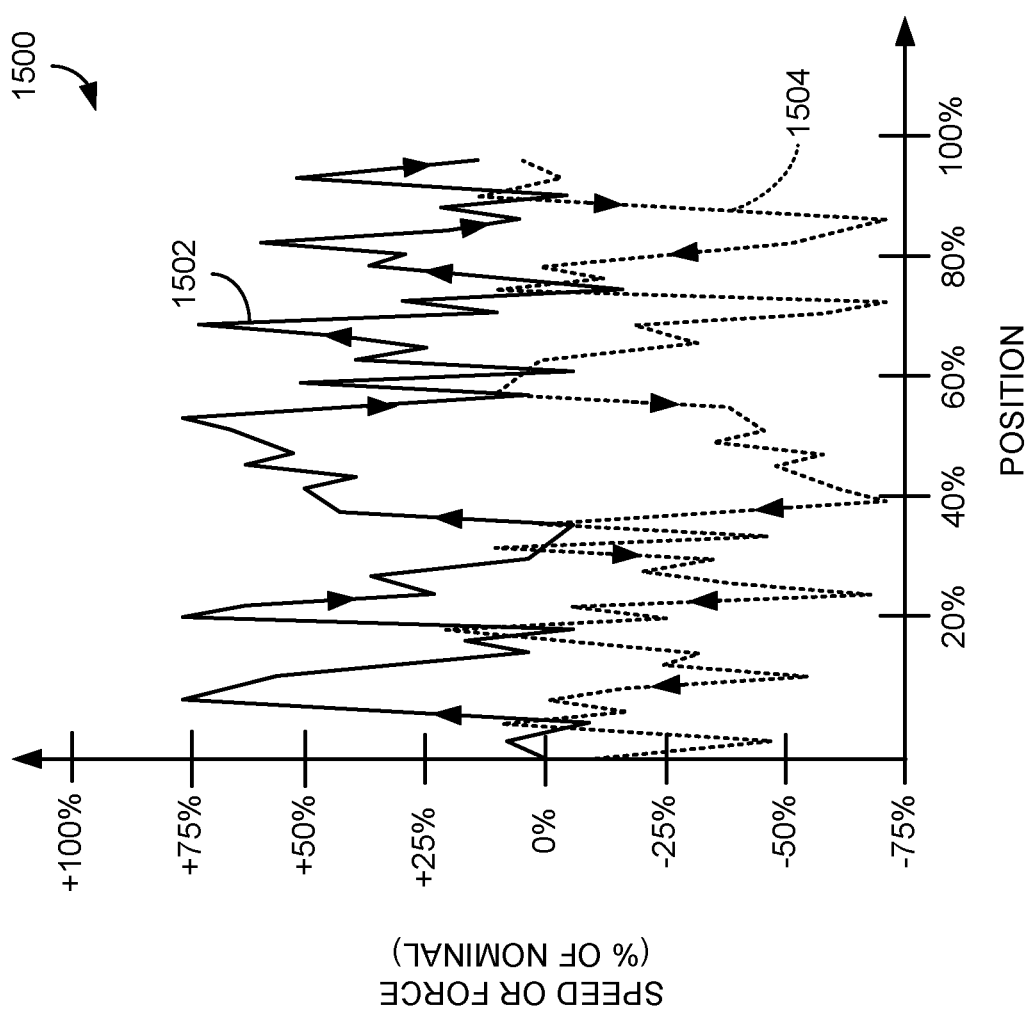
FIG. 15 is a third force profile that may be executed by a dynamic force module, the third force profile illustrating noise loading.

In still other force profiles, random noise may be applied to some nominal control parameter or value associated with the load. Doing so may decrease the stability of the load provided by the dynamic force module and, as a result, increase the challenge of performing the exercise by the user. More specifically, under such loading, the user must provide stabilization of the load in addition to executing the primary movements of the exercise. Such a force profile is illustrated in FIG. 15. FIG. 15 is a third force profile 1500 including each of a concentric phase 1502 and an eccentric phase 1504. The third force profile 1500 is intended to illustrate a force profile that applies the concepts of speed or force noise loading. During such loading, the speed of the contraction/extension or the force required for contraction/extension is not constant. Rather, some degree of noise is superimposed over a predetermined speed or force, thereby causing random variations over the range of motion associated with a given exercise.

In force noise loading, for example, a noise signal is superimposed over a force set point, thereby creating a scenario in which a user must vary the counterforce he or she provides for stable, consistent motion. Such unpredictable loading effectively "shocks" muscle groups in a way that is difficult to achieve using conventional exercise equipment. During speed noise loading, the speed with which the dynamic force module allows contraction or extension is varied about some nominal speed. For example, a cable speed may be randomly cycled between positive and negative cable speeds of varying degrees. By doing so, a user's muscles are demanded to quickly switch between concentric, eccentric, and isometric modes of operation.

Figure 16:
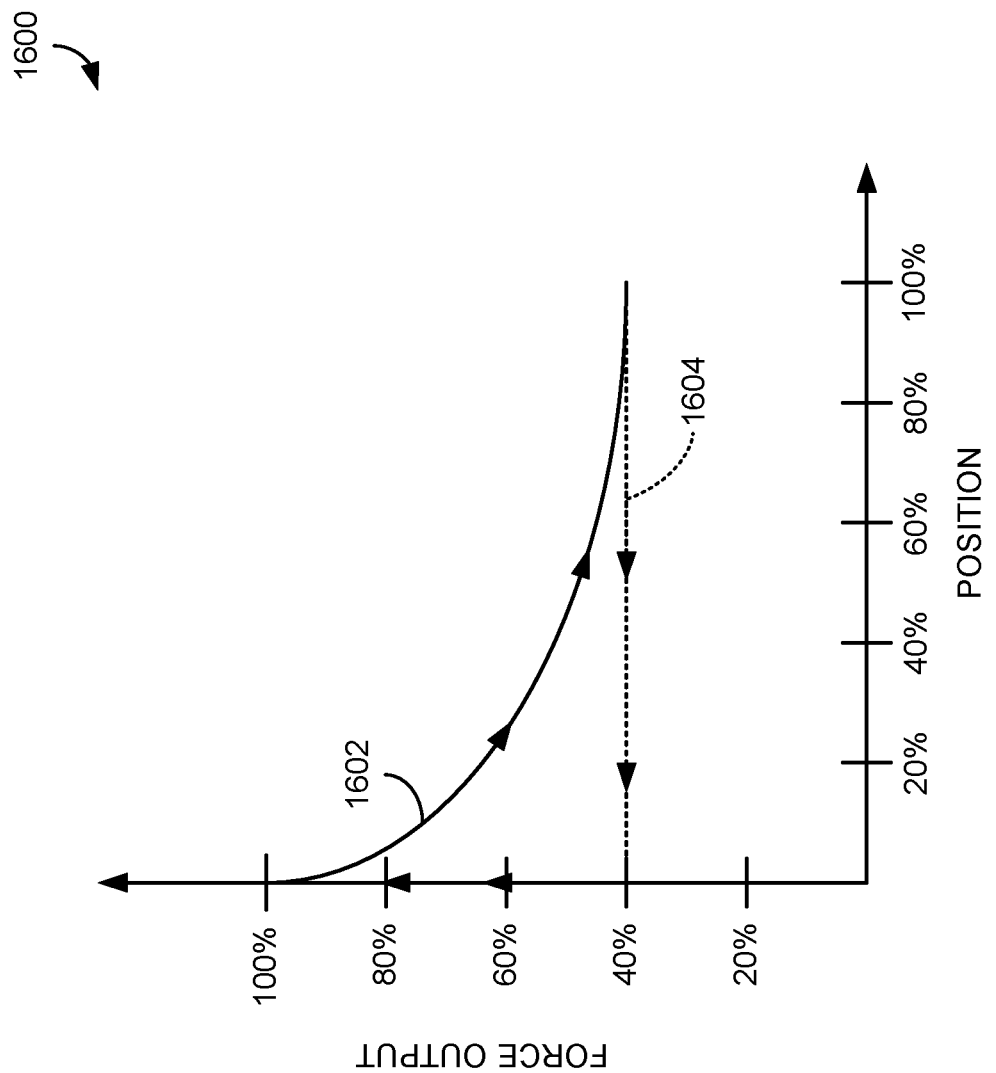
FIG. 16 is a fourth force profile that may be executed by a dynamic force module, the second force profile illustrating ballistic reactive force.

Force profiles executed by the dynamic force module may also attempt to simulate loads and physics of other exercise machines and equipment. FIG. 16, for example, is a fourth force profile 1600 including each of an extension phase 1602 and a contraction phase 1604. The force profile 1600 illustrates an implementation of ballistic loading or resistance similar to that which would be experienced when using an ergometer/rowing machine. Specifically, during the extension phase 1602, the force applied by the dynamic force module begins at a predetermined maximum value and then reduces exponentially towards a minimum force value at the end of the exercise. During the contraction phase 1604, a constant reduced force is applied to assist the user in returning back to the starting position.

Figure 17:
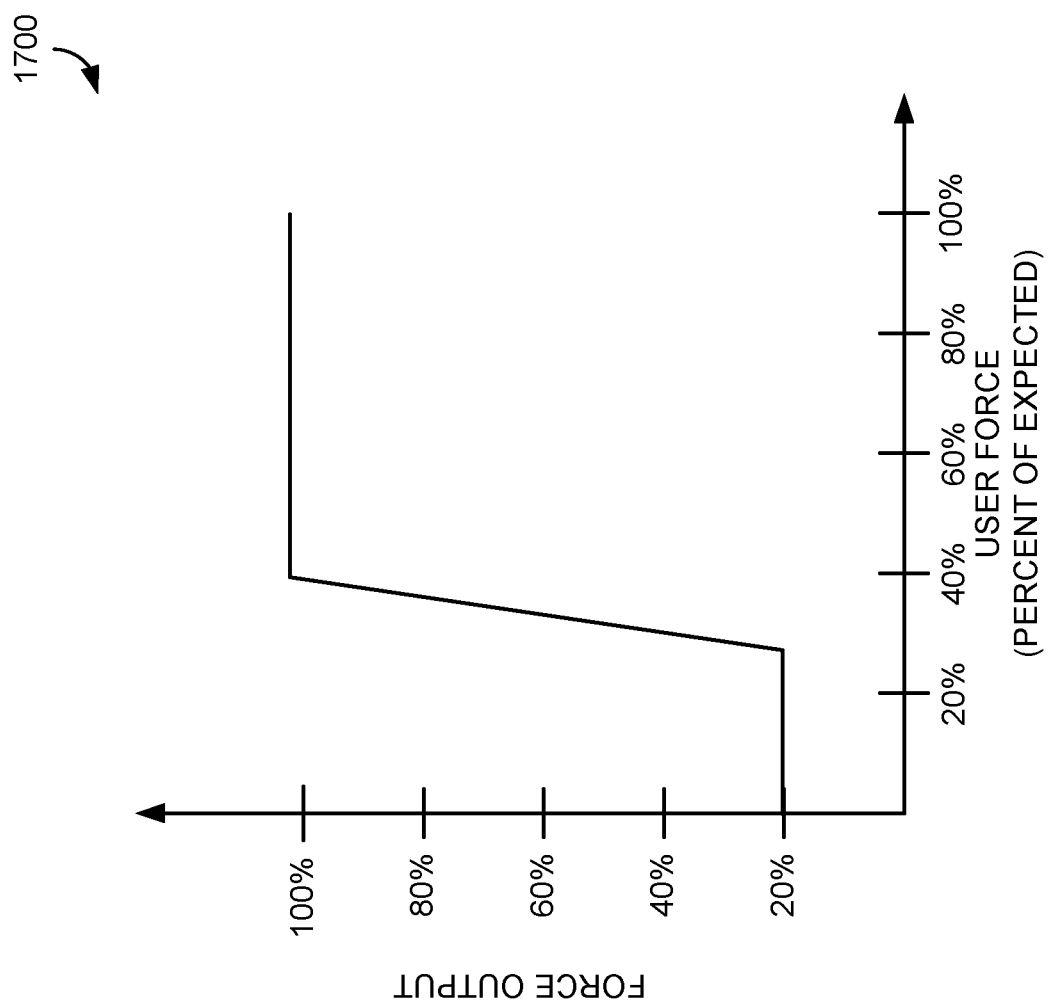
FIG. 17 is a fifth force profile that may be executed by a dynamic force module, the fifth force profile illustrating a spotting mode of the dynamic force module.

Force profiles and aspects of force profiles may also be implemented for purposes of safety and injury reduction. For example, force profiles executed by a dynamic force module may attempt to identify if a user is unable to execute an exercise at a current load and may reduce or otherwise modify the load to allow the user to safely return to a starting position or otherwise complete the exercise. FIG. 17 is a fifth force profile 1700 illustrating an example of "spotting" or assistance functionality. In general, spotting functionality may be implemented by measuring the force exerted by the user and reducing the force output of the dynamic force module in response to the force exerted by the user falling below a predetermined threshold. For example, in the specific example force profile of FIG. 17, when the user exceeds approximately 40% of an expected force, a predetermined force may be applied by the dynamic force module. However, if the user force falls below 40% and, in particular below 25%, the force output of the dynamic force module is reduced to approximately 20% of the predetermined force. Under this reduced load, the user may then return to the starting position of the exercise. Alternatively, if the user were to release the grip, handle, etc. of the exercise machine in response to becoming fatigued, the reduced load allows safe return of the dynamic force module to the starting position. In either case, a speed limit may also be applied to retraction of the dynamic force module to ensure safe, controlled return to the starting position.

Although dynamic force modules are described herein as being primarily standalone devices intended to replace conventional resistance elements, dynamic force modules may also be used in conjunction with conventional resistance elements and to supplement or otherwise provide additional functionality for performing exercises with such resistance elements. For example, a dynamic force module may be implemented into exercise equipment including conventional weights in order to provide the spotting functionality described in FIG. 17. Alternatively, the dynamic force module may be used to add reactive forces to a conventional resistance element. For example, a dynamic force module may be coupled to a weighted bar and may supplement the weight of the bar by adding additional reactive forces in the direction of gravity, such as during an eccentric phase of an exercise. A dynamic force module may also be used to add instability to a conventional resistance element. For example, a dynamic force module may be coupled to a weighted bar in order to provide vibration or "noise" to the weighted bar (similar to the example illustrated in FIG. 15) or the dynamic force module may be coupled to the weighted bar to create a load imbalance between sides of the weighted bar.

Figure 18:
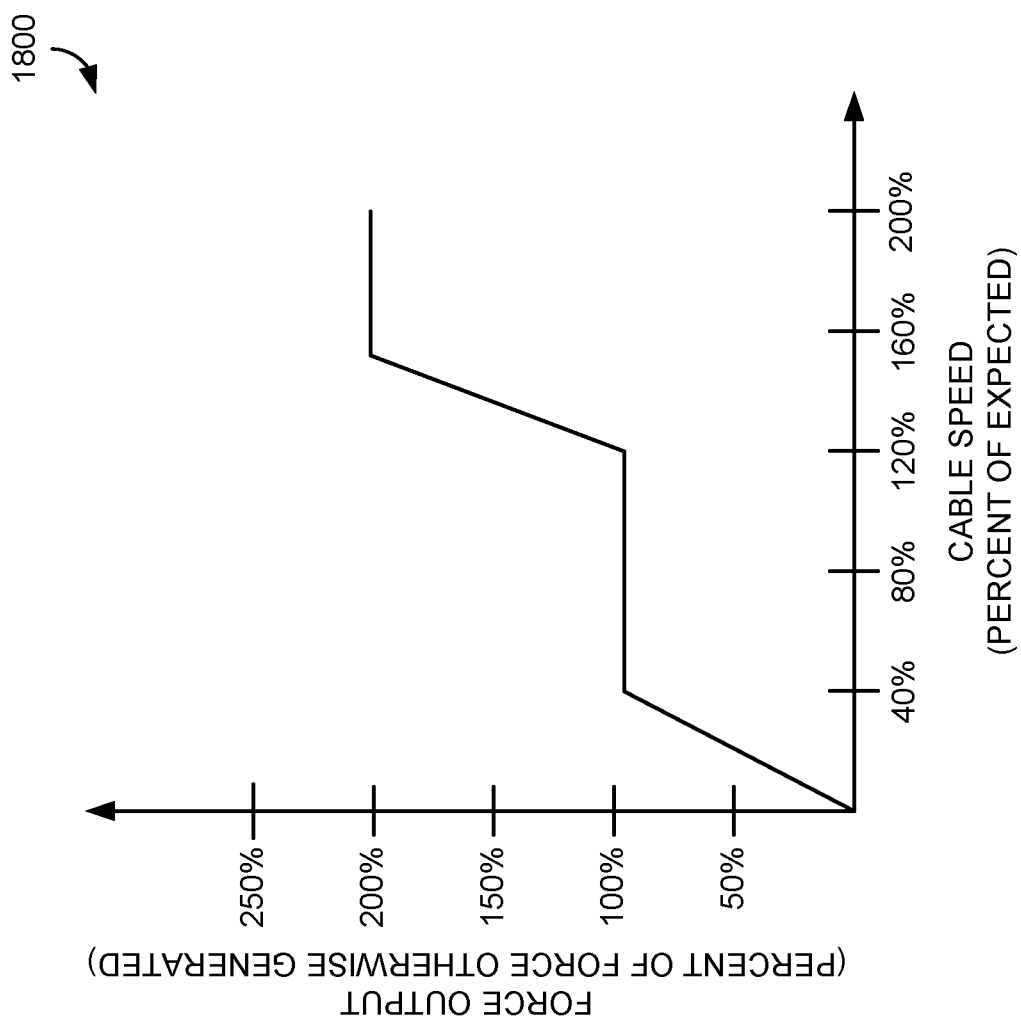
FIG. 18 is a sixth force profile that may be executed by a dynamic force module, the sixth force profile illustrating constant speed control.

Previously discussed force profiles focused primarily on the dynamic force module providing a force output based on the position of a user and, in particular, the position of the user with respect to a range of motion for an exercise. In other implementations, however, the output of the dynamic force module may be based on other measured parameters associated with an exercise performed by the user including, among other things, the speed or acceleration of the user during performance of the exercise. FIG. 18 is a sixth force profile 1800 illustrating a force profile for implementing speed control in which the force output by the dynamic force module is based on the speed at which the user is moving through an exercise. In the implementation illustrated in FIG. 18, for example, the dynamic force module provides a constant force output while extension or retraction of a cable coupled to the dynamic force module is maintained between 40% and 120% of a predetermined speed. If, however, extension or retraction exceeds 120%, the force output of the dynamic force module is increased proportionately up to double the level of the constant force output in order to encourage the user to slow his or her movement. Similarly, if the extension or retraction falls below 40%, the force output of the dynamic force module may be proportionately decreased to encourage the user to speed up his or her movement. In certain implementations, additional feedback may be provided to the user in the form of a haptic pulse or visual/audio feedback that provides warnings or other indications if the user falls outside of the ideal speed range.

Figure 19:
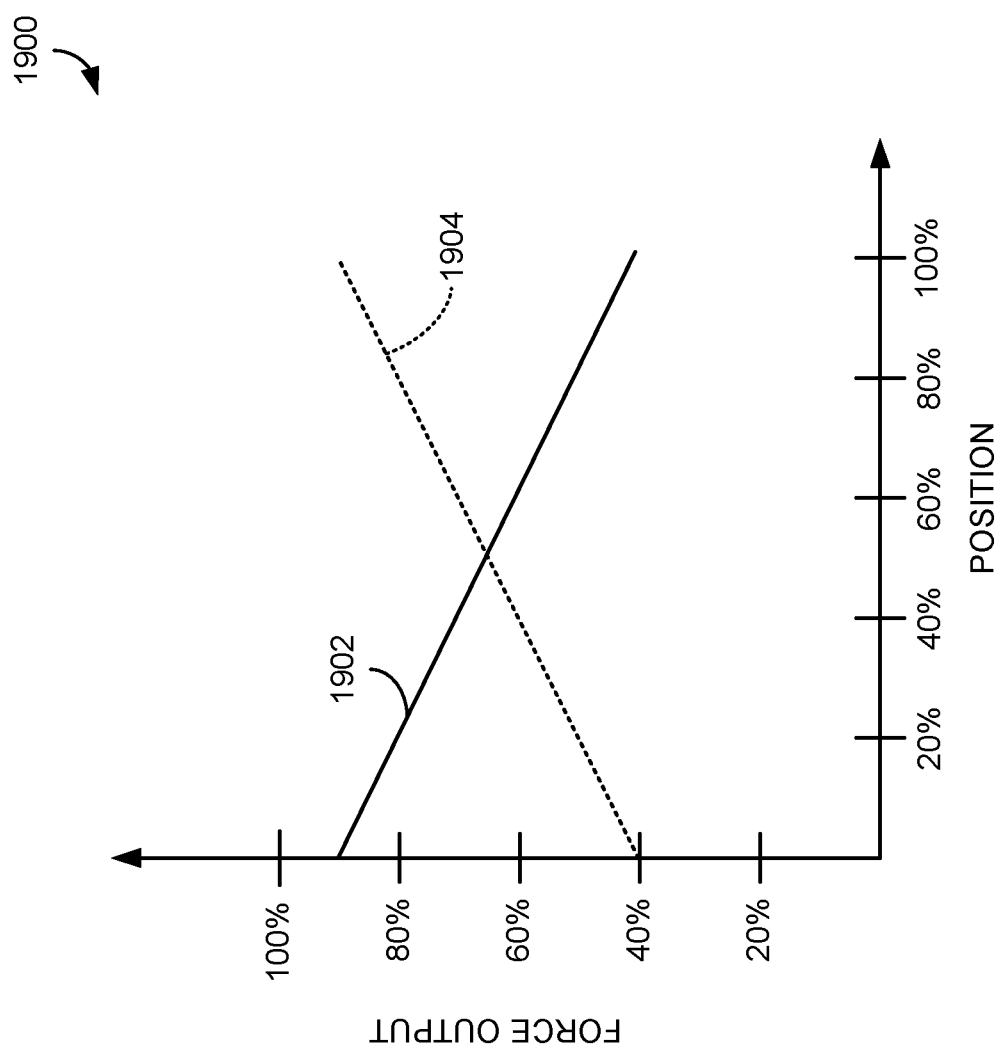
FIG. 19 is a seventh force profile that may be executed by a pair of dynamic force modules, the seventh force profile illustrating imbalanced loading applied by the pair of dynamic force modules.

As previously discussed in the context of the exercises machines 200 and 400 of FIGS. 2 and 4, respectively, some implementations of the present disclosure may include multiple dynamic force modules. In such implementations, one force profile may govern the operation of each of the dynamic force modules such that the dynamic force modules are substantially synchronized throughout an exercise. In other implementations, however, each dynamic force module may execute a different force profile, thereby causing imbalanced loading. FIG. 19 is a seventh force profile 1900 that illustrates such a case. Specifically, the force profile 1900 includes a first curve 1902 corresponding to a first dynamic force module and a second curve 1904 corresponding to a second dynamic force module. As illustrated in the force profile 1900, the force applied by the first dynamic force module starts at a high level and gradually decreases towards the end of the exercise while the force applied by the second dynamic force module starts at a low level and gradually increases a maximum at the end of the exercise. So, for example, in an implementation in which the first dynamic force module provides reactive force to a user's right arm while the second dynamic force module provides reactive force to the user's left arm, a dynamic imbalance may be created that shifts loading between the user's arms over the course of an exercise.

Although the concept of force profiles and the specific force profiles herein are described in the context of dynamic force modules, such force profiles may be applied in other systems including actuators for providing dynamic resistance. Moreover, while dynamic force modules described herein are primarily described as including motors and certain arrangements of sensors, force profiles may be used in any variation of a dynamic force module in accordance with this disclosure.

The force profiles illustrated in FIGS. 13-19 are intended merely as illustrations of force profiles that may be implemented in conjunction with dynamic force modules of the present disclosure. In general, a force profile generally dictates the force or speed at which the dynamic force module extends or retracts based on some parameter corresponding to an exercise being performed. Such parameters may include kinematics and dynamics associated with various elements including, without limitation, the user, a handle or similar accessory, a cable or link, or any other measurable aspect of the dynamic force module itself, the exercise machine to which the dynamic force module is coupled, the user, or the environment within which the dynamic force module/exercise machine is operated.

In certain implementations, the force profiles may substantially stimulate other exercise machines. For example, a dynamic force module may execute a force profile intended to mimic the dynamics of a traditional cable machine including a weight stack under normal gravity. Other force profiles may simulate any of static, sliding, rolling, or rolling friction associated with real-world objects or resistance mechanisms (e.g., pulleys, belts, cables, or similar moving parts of conventional exercise machines). The force profiles may also be based on other real-world models intended to simulate fluid dynamics (such as the dynamics of water when rowing), fans or magnetic resistance elements (such as implemented in stationary bikes and ergometers), pneumatic or hydraulic resistance elements, spring/damper systems, or any other similar systems.

Although force profiles simulating conventional exercise machines and conventional environments are possible, the force profiles implemented by the dynamic force module are not necessary limited to real world analogs. Rather, the underlying models and physics on which a force profile is based may be modified based on the particular needs and goals of a user.

In certain implementations, force profiles may reflect slightly modified versions of terrestrial physics in order to smooth the user's experience. For example, physical weight stacks have inertia such that if an explosive/ballistic movement is conducted using a physical weight stack, the weight stack will continue in an upward motion even if the person performing the exercise has stopped moving a handle, grip, etc. coupled to the weight stack. In cable-based systems, such inertia causes slack in the cable and a subsequent high-tension shock loading event when the weight stack falls under the force of gravity. In contrast, dynamic force modules according to the present disclosure may modify the simulated properties of the cable and/or weight stack to avoid such events. For example, in one implementation, the dynamic force module may simulate an elastic cable during the period when the shock loading event would occur. In another implementation, the dynamic force module may simulate a zero-inertia weight stack such that the slack and subsequent shock experienced when using actual weight stacks are eliminated. In yet another implementation, the dynamic force module may include control algorithms that limit or otherwise control movement of the cable/drum such that the cable does not go slack. In another example, a user may be tasked with catching a simulated object, such as a simulated egg or medicine ball. In the real world, catching an object generally requires the person catching the object to receive the full mass of the object at once. In contrast, the dynamic force module may create a simulated scenario in which the weight of the caught object ramps up from a small nominal value to a full simulated value over a predetermined period of time.

In another example implementation, a force profile may be executed such that the dynamics of the dynamic force module correspond to non-terrestrial gravity. So, for example, the dynamic force module may be used to simulate the gravity of the moon by reducing the resistance to upward acceleration of a simulated load, as experienced by a "floating" dynamic at the end of a vertical movement. Similarly, such resistance may be increased to simulate the gravity of another planet, such as Jupiter.

In yet another example, the physics governing a force profile may reflect movement through a particular substance.

Referring to the ergometer/rowing machine example provided in FIG. 16, for example, the rate of which the force output of the dynamic force module decays during the extension phase 1602 may be modified to simulate rowing through different media. For example, one force profile may decrease the rate of decay, thereby simulating a fluid having high viscosity, such as honey or oil. Still other force profiles may increase the rate of decay, thereby simulating fluids having low viscosity, such as various types of alcohols. In still other implementations, the force profile may reflect a non-Newtonian fluid such that the force output by the dynamic force module is inversely proportional to the force output or acceleration applied by the user. Such force profiles may be used, for example, as a method of speed control, similar to the force profiled discussed in the context of FIG. 18.

Force profiles may also be progressive in that they vary over the course of a single repetition, an exercise set, and/or a workout. For example, a force profile may be dynamically adjusted over the course of a workout to correspond to each of a warm-up period (that begins with relatively low reactive force that is gradually increased), a primary exercise period (at a relatively high reactive force), and a cool down period (that begins at a relatively high reactive force that is gradually decreased). Within each of these periods, the dynamic force module could dynamically adjust reactive forces based on feedback corresponding to the user's performance. For example, if the user exhibits consistently high speed and force, the workout may be too easy and the reactive force may be increased. In contrast, if the user exhibits inadequate force output, the workout may be too difficult and the reactive force or other difficulty-related parameter may be decreased. Accordingly, the user's level of effort and/or muscular breakdown may be made to follow a separately defined trajectory. In this way, the dynamic force module could ensure that a user reaches particular thresholds for warming and/or muscular breakdown within a predetermined time or number of sets. In certain implementations, a user may be asked by the system to perform one or more warmup exercises or otherwise perform a particular exercise at a relatively low weight. During the course of the warmup, the system may analyze the user's performance and select an appropriate force profile to use during the main set or sets of the exercise based on the user's performance.

In one implementation, the concept of progressive force profiles may be used to execute "drop sets", which are commonly practiced among advanced weightlifters. In a conventional drop set workout, weight/resistance is reduced every few reps to keep a weightlifter near the point of muscular breakdown. Accordingly, to implement drop sets in the context of dynamic force modules, the reactive force for a given force profile may be dynamically adjusted downward every few reps as deemed appropriate by the system. Notably, conventional drop sets require the weightlifter to have access to a wide range of weights (which are generally only available in discrete increments) and to quickly switch between such weights. In contrast, the dynamic force module includes a near-continuous force range and can make reactive force changes on the fly. Moreover, the dynamic force module is able to provide a wider range of force profiles, including those having varying reactive forces between the eccentric and concentric phases of an exercise.

FIGS. 20-29B illustrate various human feedback mechanisms and user interfaces that may be implemented in conjunction with dynamic force modules according to the present disclosure. In general, the human feedback mechanisms are intended to provide feedback to a user regarding the user's performance of a given exercise. Feedback may take various forms including, without limitation, one or more of audio, visual, and haptic feedback, each of which may vary in intensity based on the degree to which the user deviates from a benchmark or similar value.

Although other types of audio feedback are possible, examples of audio feedback include, without limitation, a buzzer, a beeping sound, one or more tones played in succession, and voice feedback. In certain implementations, the audio feedback may be varied in tone, intensity, or quality based on the degree of feedback provided to the user. With respect to voice-based feedback, the dynamic force module 500 may be adapted to play various phrases regarding the degree of deviation by the user and/or that provide specific instructions to the user. For example, if a user is executing a particular movement too quickly, the voice-based feedback may instruct a user to slow down.

Visual feedback may also take various forms. In some example implementations, visual feedback may be provided in the form of one or more lights/LEDs adapted to illuminate based on the user's performance. For example, a system may include each of a green LED, a yellow LED, and a red LED for indicating whether a user is performing a particular exercise according to target parameters, slightly outside target parameters, or well outside target parameters, respectively. Visual feedback may also make use of a screen or other display for presenting information to the user. A screen may be used, for example, to provide one or more of graphical and textual feedback to the user. In either case, such feedback may include particular instructions to encourage the user to perform an exercise within target parameters. Visual feedback may also be provided in the form of a numerical score or similar metric for measuring the user's performance with proper performance of an exercise earning greater points than improper performance of the exercise.

Haptic feedback may also be provided to the user. For example, the handles, grips, or other elements of the dynamic force module or exercise machine may include mechanisms to cause vibration or pulsation. Haptic feedback may also be provided by a separate device, such as a smartphone, smartwatch, fitness tracker, or similar item kept on the user with haptic feedback functionality.

In general, the feedback mechanisms discussed herein are communicatively coupled to one or more dynamic force modules such that the feedback mechanisms may be used within a control loop for controlling the dynamic force modules and providing feedback to the user. For example, the user interfaces discussed herein may be presented on a display of a computing device that is wirelessly coupled to a dynamic force module of an exercise machine. Similarly, audio and haptic feedback components may also be coupled to one or more dynamic force modules such that the dynamic force module may provide feedback to the user.

Figure 20:
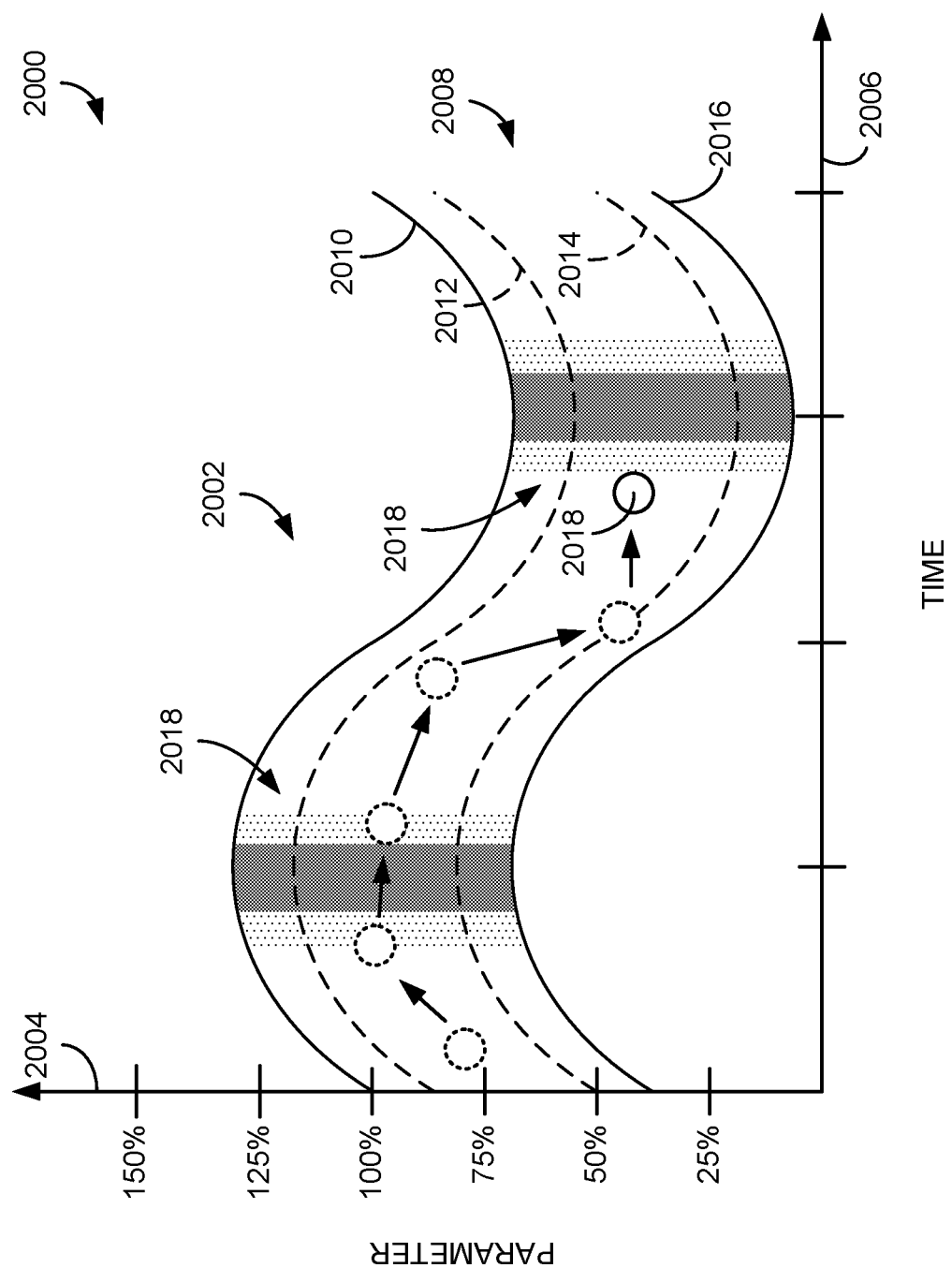
FIG. 20 is a first example of an interactive animation for providing feedback to a user using a dynamic force module in accordance with the present disclosure, the first interactive animation including variable boundaries.

FIG. 20 is a first example of a display 2000 for providing feedback to a user using a dynamic force module in accordance with the present disclosure. The display 2000 may corresponding to a display integrated into an exercise machine including a dynamic force module or may correspond to a computing device communicatively coupled to the dynamic force module, such as a smartphone, laptop, tablet, or similar device.

The display 2000 illustrates a relatively general implementation of a human feedback mechanism including an animated graph 2002. As shown, the animated graph 2002 includes a y-axis 2004 for indicating a measured parameter and an x-axis 2006 representing time. The measured parameter can be any of a number of parameters including, without limitation, one or more of user force, dynamic force module force, user position, user speed, or any other measurable parameter of the user, dynamic force module, or exercise machine including the dynamic force module. Although indicated as time, the x-axis 2006 may alternatively correspond to other parameters including, without limitation, the user's position over a range of motion, the user's relative progress through an exercise repetition or set of repetitions, or the user's progress through a longer workout.

In the example display 2000, a boundary collection 2008 is superimposed on the animated graph 2002 to provide a visual indication of acceptable ranges of the parameter. The example boundary collection 2008 of FIG. 20 includes each of a maximum boundary 2010, a high boundary 2012, a low boundary 2014, and a minimum boundary 2016. During operation, an animated marker 2018 tracks the parameter corresponding to the y-axis 2004 and moves across the display. In certain implementations, the screen may refresh when the animated marker 2018 reaches the end of the display in order to present the subsequent segment of the boundary collection 2008. Alternatively, instead of the animated marker 2018 traversing across the display 2000, the boundary collection 2008 may instead scroll across the display 2000.

The boundary collection 2008 may be used to define various ranges for the measured parameter. For example, values of the measured parameter between the high boundary 2012 and the low boundary 2014 may be considered acceptable. Accordingly, when the marker 2018 is within such a range, no additional feedback or even positive feedback may be provided. Such positive feedback may include, without limitation, encouraging text, encouraging voice messages, positive points (or a similar scoring metric), bell dings, illumination of green lights/LEDs, and the like.

The ranges between the high boundary 2012 and the maximum boundary 2010 and between the low boundary 2014 and the minimum boundary 2016 may correspond to a first level of corrective feedback. If the marker 2014 enters these ranges, various forms of feedback may be provided. For example, in certain implementations, a tone or haptic feedback may be provided at a first intensity and/or frequency, a yellow/amber light or LED may be illuminated, or audio or textual warning messages may be provided to the user. Messages provided to the user may also include specific instructions (e.g., "Slow down", "Try harder", etc.) directing the user back into the preferred range of the measured parameter. A subsequent level of feedback may be provided if the user exceeds the maximum boundary 2010 or falls below the minimum boundary 2016. Moreover, in certain implementations, the dynamic force module may be configured to stop or modify a given exercise or workout if the user falls outside of the maximum or minimum boundaries for a predetermined amount of time.

As indicated in FIG. 20, the display 2000 may include a third dimension in addition to the parameters associated with each of the x- and y-axes. For example, visual indicators may be applied in the animated graph 2002 to convey information corresponding to another parameter associated with an exercise. So, for example, in one implementation, the y-axis 2004 may correspond to a user's speed, the x-axis 2006 may correspond to time, and color may be used to indicate reactive force, with darker, more intense colors corresponding to higher reactive force. Referring to FIG. 20, for example, the animated graph 2002 includes two phases 2018, 2020 in which reactive force is temporarily ramped up, as indicated by gradients applied in each of the two phases 2018, 2020. In other implementations other visual indicators may be used to illustrate the third parameter. For example, instead of a gradient, a color change may be implemented in sections of the animated graph 2002. In other implementations, the animated graph 2002 may include vertical lines or other symbols, the spacing between which serves as an indicator of the value of the third parameter.

FIG. 21 illustrates an example interactive animation 2100 that may be displayed to a user to provide feedback. Specifically, FIG. 21 illustrates a throwing simulation in which a parameter associated with an exercise performed by a user (e.g., speed or force) is used as an input for an animation in which an object 2102 is thrown by an arm 2104 at a target 2106. In such an implementation, the object 2102 may be made to hit the center or bullseye of the target 2106 in response to the user performing an exercise such that the measured parameter is within a target range. In response to the user falling below or exceeding the target range, the object 2102 may be under- or over-thrown by the arm 2104, respectively. In such cases, corrective feedback may be provided to the user.

In certain implementations, the dynamic force module may provide a reactive force that reflects the task/activity/animation presented to the user. For example, referring back to the example of FIG. 21, the dynamic force module may simulated actually throwing of the object 2102 and may adopt a force profile that provides reactive force reflecting the real-world physics of doing so. In certain implementations, the object 2102 may be varied and corresponding changes may be made to the force profile implemented by the dynamic force module. For example, in a subsequent repetition, the object 2102 may be increased in size, implying that the weight of the object being thrown has increased. In conjunction with this visual change, the dynamic force module may similarly modify its existing force profile or adopt a new force profile corresponding to the increased size of the object.

Whereas the throwing example of FIG. 21 corresponds primarily to a concentric motion, similar animations may be used for eccentric motions as well. For example, FIG. 22 illustrates a second interactive animation 2200 in which an object 2202 is instead caught by an arm 2204 which is displayed in response to user movement and reactive force. In contrast to the throwing motion of FIG. 21, which emphasizes concentric motion required to accelerate an object at rest, the catching motion of FIG. 22 is intended to simulate decelerating an object, which emphasizes eccentric motion. In certain implementations, for example, the object 2202 may be a virtual egg or a similar breakable object such that if the user provides insufficient or excessive counterforce when catching the object, the object may be shown to crack or break in the animation 2200. However, if the user decelerates the object appropriately, the object will remain intact, indicating a proper repetition. Similar to the throwing example, the size of the object 2202 may be varied between repetitions or sets to indicate change in the reactive force provided by the dynamic force module.

FIG. 23 illustrates an indicator 2300 that may be implemented on its own or in conjunction with the various other interactive animations and feedback mechanisms discussed herein. In particular, the indicator 2300 includes a set of bars that may be used to provide feedback to the user regarding a particular exercise or task. So, if the user performs an exercise properly, a central bar 2302 may be illuminated. To the extent the user under- or over-performs the exercise, corresponding bars below 2304 or above 2306 the central bar 2302 may be illuminated accordingly. For example, in certain implementations the indicator 2300 may be displayed adjacent the throwing interactive animation 2100 of FIG. 21 to provide the user with additional feedback regarding whether and to what extent the user's actions led to the object 2102 being under- or over-thrown.

Figure 24A:
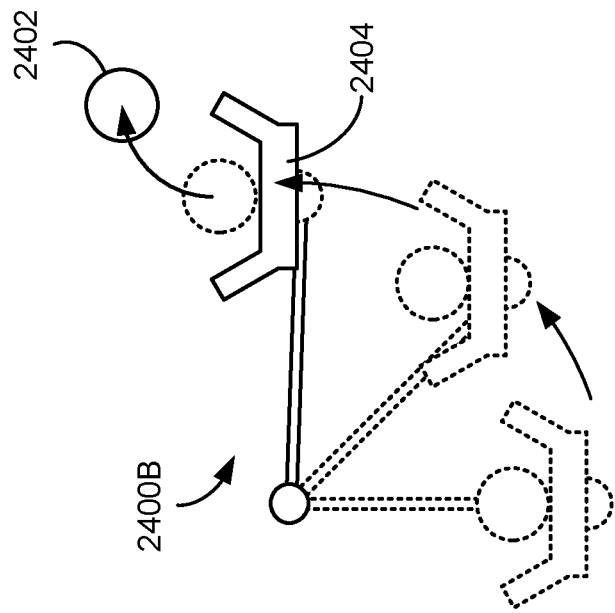
FIGS. 24A and 24B are, in combination, a fifth example of an interactive animation for providing feedback to a user using a dynamic force module, the fifth interactive animation including a simulated receiving and passing of an object.
Figure 24B:
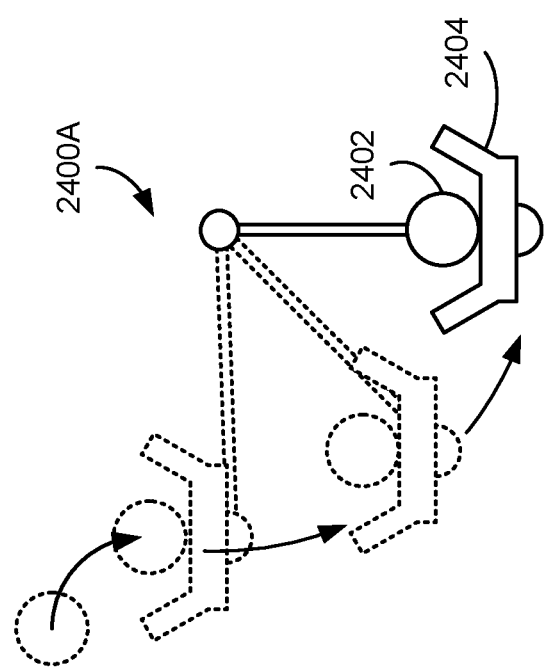

FIGS. 24A-24B, in combination, illustrate another interactive animation. Specifically, FIG. 24A illustrates an eccentric motion 2400A in which an object 2402 is received by an arm 2404 which must be slowed by the application of an appropriate counterforce by the user. FIG. 24B illustrates a subsequent concentric motion 2400B in which the object 2402 is thrown or otherwise released from the arm 2404 in response to the user applying a corresponding force. Again, successful performance of the exercise may be indicated by the object 2402 remaining intact during the eccentric phase and by being launched a certain distance during the concentric phase.

Interactive animations may correspond to the execution of multiple force profiles over the course of the animation. For example, with reference to the animation of FIGS. 24A-24B, a distinct force profile may be executed by the dynamic force profile for each of the catching/receiving phase illustrated by FIG. 24A, the passing phase illustrated by FIG. 24B, and the transitionary period between the catching/receiving phase and the passing phase. Moreover, an interactive animation may correspond to a multi-user or multi-player experience in which multiple users perform an exercise or activity represented by the animation. For example, two or more users operating exercise equipment equipped with respective dynamic force modules may play a simulated game of catch with each other or otherwise pass a simulated object between themselves. In such implementations, the dynamic force modules may communicate with each other or otherwise coordinate execution of their respective force profiles in accordance with the multi-user interactive animation. Such multi-user exercises may also be conducted using the same exercise machine/dynamic force module.

Figure 25A:
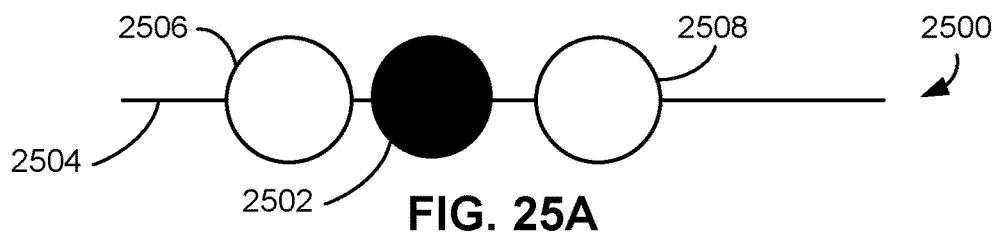
FIGS. 25A and 25B illustrate a sixth example of an interactive animation for providing feedback to a user using a dynamic force module, the sixth interactive animation including a one-dimensional indicator for providing feedback to the user.
Figure 25B:
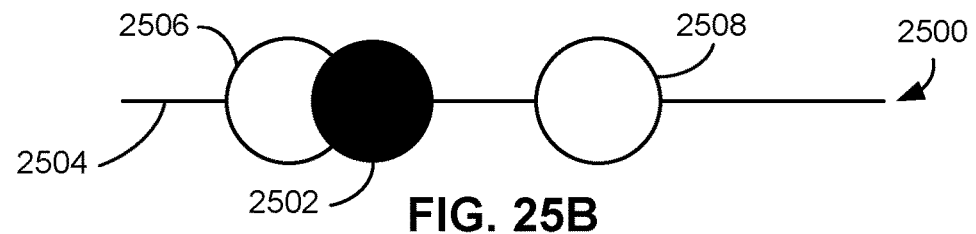

FIGS. 25A-25B illustrate yet another interactive animation 2500 intended to guide and provide feedback to a user. The interactive animation 2500 is a simple one-dimensional visualization in which a primary marker 2502 corresponding to a measured parameter moves along an axis 2504 between two extend markers 2506, 2508. FIG. 25A illustrates the case in which the measured parameter is within an acceptable range, indicating that the user is properly performing a given exercise. In contrast, FIG. 25B illustrates the case in which the measured parameter falls outside of an acceptable range as indicated by interference between the primary marker 2502 and the marker 2504. In the case illustrated in FIG. 25B additional feedback may be provided to the user in the form of, among other things, haptic pulses, audio indicators, or a point/scoring penalty.

Figure 26A:
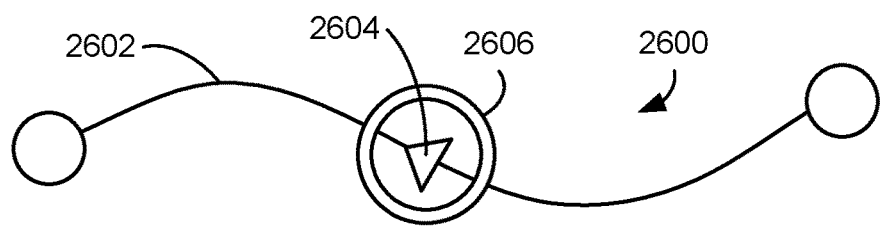
FIGS. 26A and 26B illustrate a seventh example of an interactive animation for providing feedback to a user using a dynamic force module, the seventh interactive animation including a two-dimensional axis and a circle indicating a target for the user.
Figure 26B:
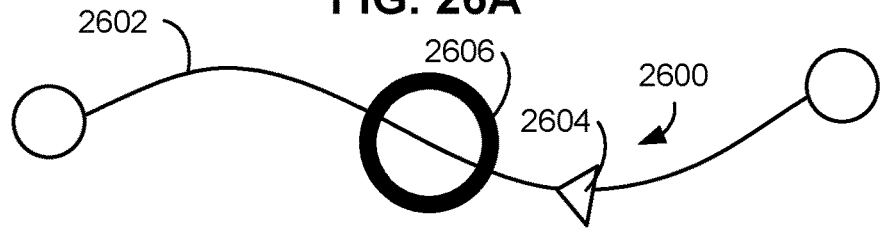

FIGS. 26A-26B illustrate another interactive animation 2600 intended to guide and provide feedback to a user. The interactive animation 2600 includes a path 2602 along which an indicator 2604 travels. As previously noted, the interactive animation 2500 of FIGS. 25A-25B was a one-dimensional visualization in which the primary marker 2502 moved linearly along a single axis. In contrast, the interactive animation 2600 adds a second dimension as indicated by the curved path 2602. More specifically, displacement along the path 2602 may be affected by each of two measured parameters with one measured parameter resulting in horizontal movement of the indicator 2602 and a second measured parameter resulting in vertical movement of the indicator 2604. The path 2602 may represent a range of absolute or relative values of the measured parameter. The interactive animation 2600 further includes a circle 2606 or similar shape representing optimal or target values for the measured parameters. Accordingly, as the user performs an exercise, the indicator 2604 moves with the goal of the user being to position the indicator 2604 within the circle 2606, as shown in FIG. 26A. If the indicator 2604 falls outside the circle 2606, various forms of feedback may be provided to the user. For example, as shown in FIG. 26B, the color of the circle 2606 may change. In other implementations, haptic, audio, or other feedback may also be provided to the user.

Figures 27, 28:
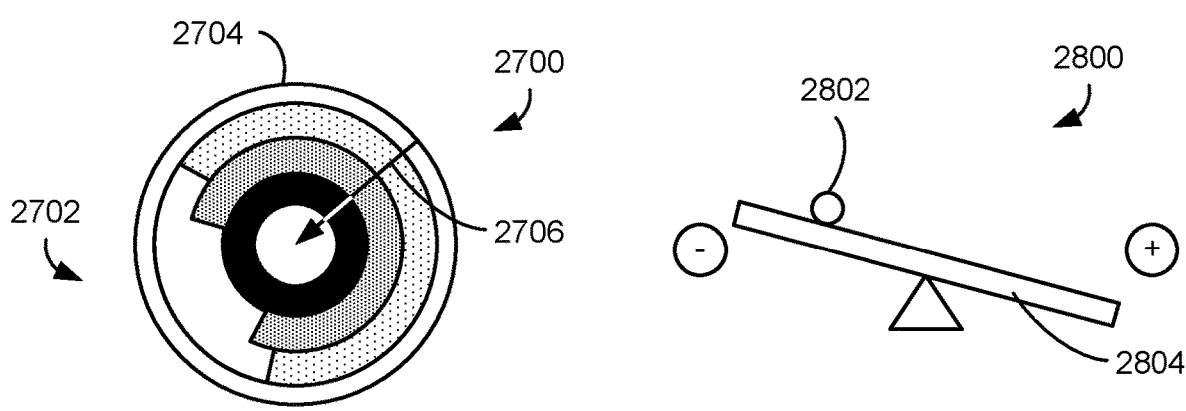
FIG. 27 is an eighth example of an interactive animation in the form of animated concentric circles.
FIG. 28 is a ninth example of an interactive animation in the form of a simulated ball and beam.

FIG. 27 illustrates an interactive animation 2700 that includes a series of concentric rings 2702 to guide and provide feedback to a user. In certain implementations, a display may include multiple similar circles, each of which may correspond to a separate phase (e.g., concentric, eccentric, isometric) of an exercise. In certain implementations, the animation 2700 may include an outer ring 2704 that constricts or shrinks towards the center of the concentric rings 2702, as indicated by arrow 2706. The time taken for the ring 2704 to fully shrink may, for example, correspond to the time required or recommended to perform an exercise or portion of an exercise. The other stationary rings may be used to indicate other aspects of an exercise. For example, variations in color, pattern, texture, or density of the rings may be used to indicate, among other things, desired force to be applied by the user at a given point in time. In certain implementations, yet another dimension may be indicated by the completeness/thickness of each concentric ring. So, in the example of FIG. 27, movement/shrinkage of the outer ring 2704 may provide an indication of speed, the color of the remaining concentric rings may indicate relative progress through an exercise, and the relative completeness of each concentric ring may indicate the relative reactive force applied during different stages of the exercise.

FIG. 28 illustrates another example interactive animation 2800 in which a ball 2802 is balanced on a beam 2804 that moves in response to a measured parameter. Accordingly, the slope of the beam 2804 generally represents a deviation of the measured parameter from a nominal value or range. For example, in certain implementations the slope/orientation of the beam 2804 may correspond to the position of an actual beam or actual bar held by the user such that the user is encouraged to maintain the actual beam/bar in a level orientation. In another example, the orientation of the beam 2804 may be based on a force applied by the user such that the user is required to apply and maintain force within a particular range to keep the ball 2804 on the beam 2802.

Figure 29A:
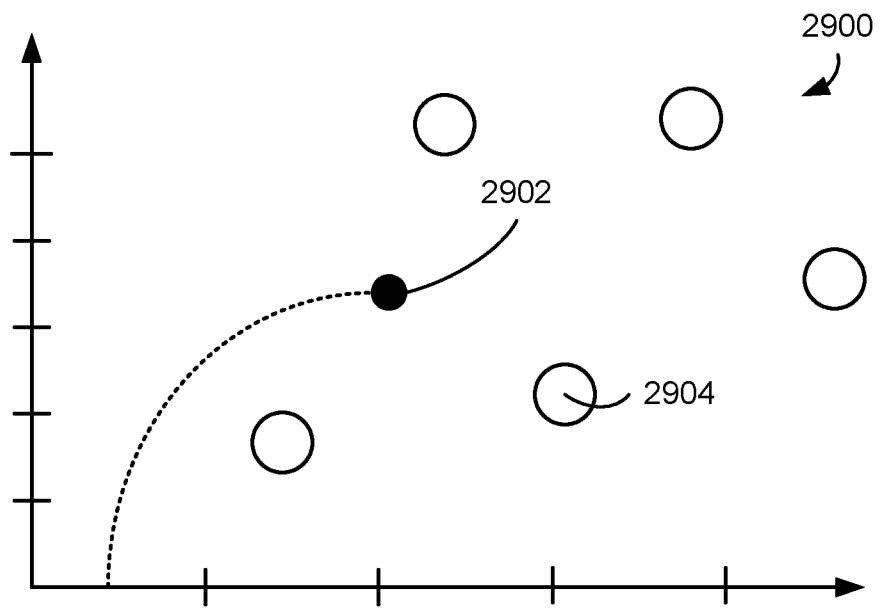
FIGS. 29A and 29B illustrate a tenth example of an interactive animation for providing feedback to a user using a dynamic force module, the tenth interactive animation including a two-dimensional space through which a user guides a marker.
Figure 29B:
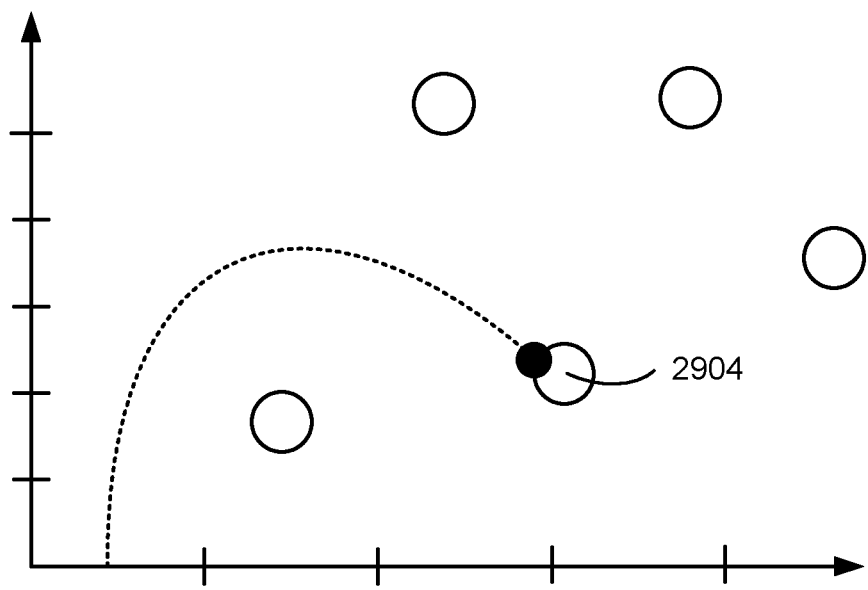

FIGS. 29A and 29B illustrate a last example interactive animation 2900. The interactive animation 2900 illustrates another two-dimensional/two-axis implementation in which each axis corresponds to a different measureable parameter associated with an exercise, set of exercises, or workout. As shown, the interactive animation 2900 includes a user marker 2902 that moves through a two-dimensional space populated by non-user markers, such as non-user marker 2904. During use, actions of the user cause the user marker 2902 to move through the space 2904. For example, movement of the user marker 2902 in a horizontal direction may be based on the position of the user while movement of the user marker 2902 in the vertical direction may be based on force applied by the user. In certain implementations, the goal of the user may be to navigate the user marker 2902 to avoid the non-user markers 2904, the user gaining points or receiving other positive feedback based on, among other things, the number of non-user markers 2904 avoided or the amount of time the user avoids contacting the non-user markers 2904. In other implementations, the goal of the user may be to contact each of the non-user markers 2904, collecting points or receiving similar positive feedback for contacted non-user marker 2904.

The foregoing examples of interactive animations are merely intended to provide examples of possible animations that may be used to provide feedback to and guide a user through an exercise, set of exercises, or workout. The foregoing examples are also merely intended to illustrate how certain force dynamics may be represented and are not intended to be limiting with respect to the visual elements used in interactive animations. Rather, visual elements of the interactive animations may be presented in various ways and may permit the application of skins or similar visual templates. Such skins may be used, for example, to make the interactive animations more engaging and/or to incorporate branded or advertising content into the interactive animations. Moreover, although described above as primarily including a visual element presented to the user via a display, the feedback principles described may also be applied to "blind" applications in which visual feedback is not provided. For example, the boundaries discussed in the context of the example of FIG. 21 may be implemented entirely within internal logic of the dynamic force module and may not be visually presented to the user. In such cases, other forms of feedback, such as haptic or audio feedback, may be the primary feedback mechanism for guiding the user. In the haptic case, for example, the intensity, frequency, or pattern of haptic pulses may be varied based on the user's deviation from an optimal value or range. Volume, pitch, frequency, or other variable aspects of an audio signal may similarly be used to indicate deviation when audio feedback is implemented.

Figure 30:
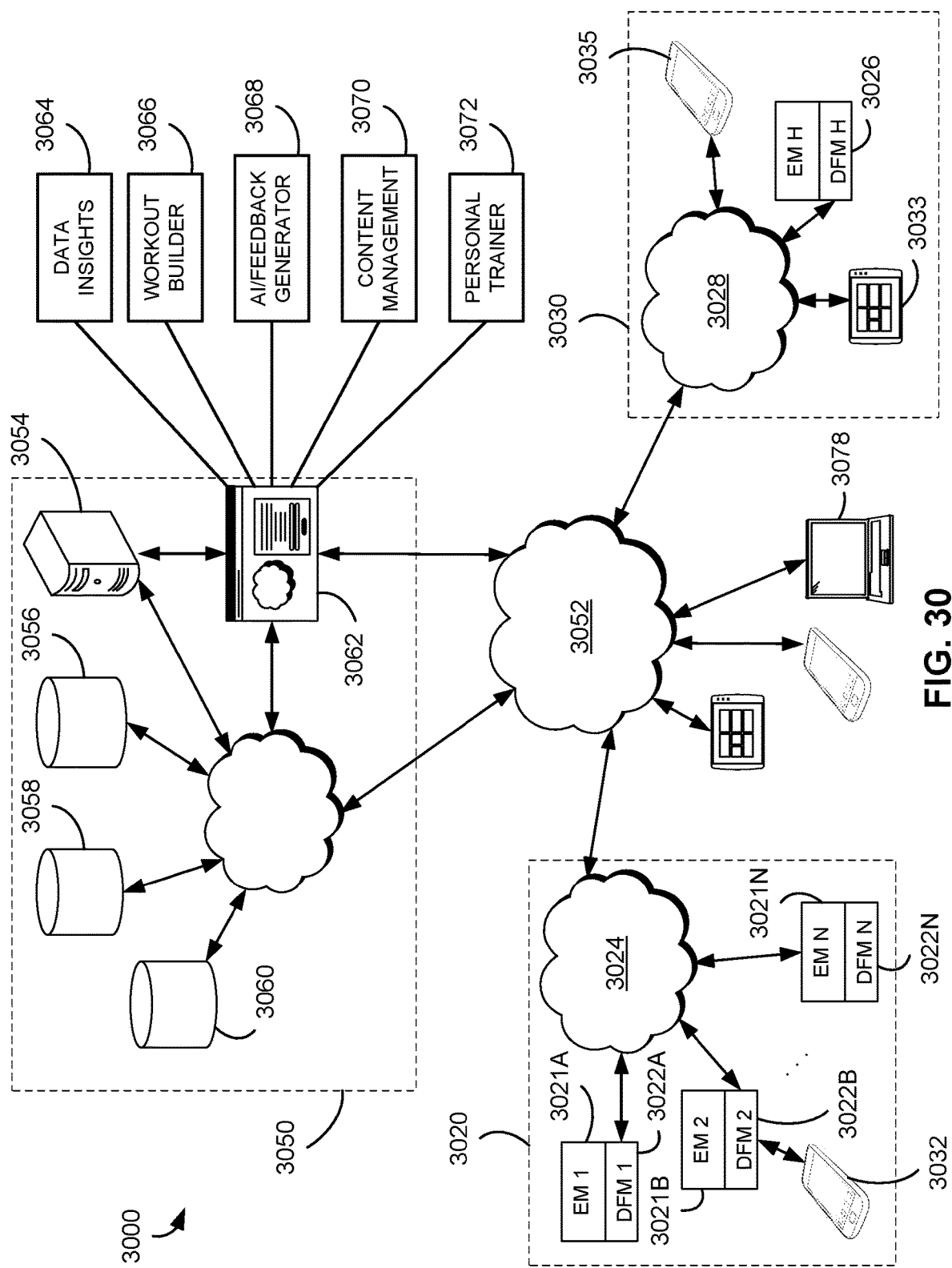
FIG. 30 is an example network environment for operating and managing dynamic force modules.

FIG. 30 is a schematic illustration of an example network environment 3000 intended to illustrate various features of dynamic force modules according to the present disclosure. In general, dynamic force modules are capable of communicatively coupling to other computing devices either directly or over a network, including over the Internet. Such coupling may be used to facilitate, among other things, configuration of the dynamic force modules, control of the dynamic force modules, tracking and analysis of user performance, and other interaction between the user and dynamic force modules.

The example network environment 3000 includes each of a gym facility 3020 and a home 3030 communicatively coupled to a cloud-based computing platform 3050 over a network 3052, such as the Internet. Each of the gym facility 3020 may include one or more exercise machines (EM 1-EM N) 3021A-3021N, each of which may in turn include one or more dynamic force modules. For example, the gym facility 3020 is illustrated in FIG. 30 as including dynamic force modules 3022A-3022N (DFM 1-DFM N), each of which are connected to a gym network 3024. Similarly, the home 3030 includes an exercise machine (EM H) 3026 including a dynamic force module (DFM H) 3027 coupled to a home network 3028. Example network topologies that may correspond to the gym network 3024 and the home network 3028 are described in more detail in FIGS. 31-34.

Each dynamic force module within the network environment 3000 may also be communicatively coupled to a computing device, such as a laptop, smartphone, smartwatch, exercise tracker, tablet, or similar device. For example the exercise machine 3022B is illustrated as being in direct communication with a smartphone 3032. Similarly, the home exercise machine 3026 is shown as being communicatively coupled to each of a tablet 3033 and a smartphone 3035 over the home network 3028. During use of the exercise machines, the respective computing devices may be used to display settings, progress, statistics, and other information to the user while also receiving commands from the user in order to control the exercise machine and/or any corresponding dynamic force modules.

Functionality of dynamic force modules and user features may be supported through a cloud-based computing platform 3050 accessible via a network 3052, such as the Internet. As illustrated in FIG. 30, the cloud-based computing platform 3050 may include a server 3054 or one or more similar computing devices communicatively coupled with various data sources, the server 3054 adapted to write data to the data sources and to retrieve data from the data sources in response to requests received by the server 3054.

The cloud-based computing platform 3050 may further include functionality for logging in and authenticating users. In certain implementations, such authentication may occur as users move between exercise stations in a particular facility such with minimal overhead to the user. For example, as a user moves between the exercise machines 3021A-3021N of the gym facility, a smartphone or similar computing device of the user may connect with the respective dynamic force modules 3022A-3022N and be authenticated by the cloud-based computing platform 3050. Such dynamic authentication may leverage a biometric sensing modality (such as, without limitation, finger print sensing, facial recognition, force signature, or voice recognition), near field radio beacon, user-linked avatar selected on a display of the computing device or the respective exercise machine, automatic connection and authentication using a short range communication protocol, or an imaging sensor or similar vision system.

In one implementation, the cloud-based computing platform 3050 may include a user information data source 3056 that stores user data. Such user data may include, among other things, personal information about the user, personal preferences of the user, historical exercise data regarding the user, and similar information. Personal information may include, for example, the user's height, weight, and full or partial medical history including various health-related metrics such as, without limitation, the user's historical heart rate, VO2 max, body fat percentage, hormone levels, blood pressure, and similar biometric data. Historical exercise data may include, among other things, previous exercises performed by the user, reactive force or similar parameters used when previously performing exercises, and the quality or effectiveness with which the user performed previous exercises (as measured, for example, by a score, points, or similar system).

In certain implementations, connection and authentication of a user with a particular dynamic force module may also initiate an auto-configuration of the exercise equipment and dynamic force module based on data stored in the user information data source 3056. Such auto configuration may include, without limitation, downloading of any force profiles or settings information to be implemented by the dynamic force profile and automatic reconfiguration of the exercise machine to account for the user's particular physical characteristics or the exercise to be performed by the user. For example, as discussed in the context of FIG. 1, an exercise machine in which a dynamic force module is incorporated may include one or more secondary actuators for adjusting the position and orientation of components of the exercise machine to account for variations in stature and exercises. Accordingly, in certain implementations, the process of connecting and authenticating a user may further include activating such secondary actuators to automatically adjust the exercise machine to accommodate the particular user. The exercise machine may also include passive components that may be manipulated by the user to mechanically reconfigure the exercise machine. In such cases, connecting and authenticating a user may further include presenting the user with a list of adjustments or settings to be applied to the exercise machine to account for the user's physical characteristics and/or the exercise to be performed.

The cloud-based computing platform 3050 may also include an exercise data source 3058 that includes a library of exercises and associated data for executing such exercises using an exercise machine including a dynamic force module. More specifically, each exercise included in the exercise data source 3058 may include, among other things, a force profile for controlling one or more dynamic force modules during performance of the exercise, ranges or values for parameters that may be measured during the exercise (speed, position, force, etc.), a mapping describing how such parameters are to be modified for various user types, and similar data related to controlling the dynamic force module and providing user feedback during the exercise. During or after completion of an exercise routine or workout, updated exercise data for a user may be uploaded to the cloud-based computing platform 3050 for storage in the exercise data source 3058.

The cloud-based computing platform 3050 may further include a content data source 3060 that includes multimedia content such as, without limitation, videos, images, audio, text, interactive animations/games, and similar content. Such content may be used to, among other things, provide instruction to a user, to provide feedback to a user, to provide motivation to a user, or to otherwise supplement the user's experience.

In certain implementations, the cloud-based computing platform 3050 may be accessible through a web portal 3062 or through a corresponding application. In the example cloud-based computing platform 3050, the web portal 3062 includes various modules such as a data insights module 3064, a workout builder module 3066, an AI/feedback generator module 3068, a content management module 3070, and a personal trainer module 3072. Notably, the web portal 3062 or similar application may be accessible through the Internet 3002 or similar network 3002 using a computing device that is not communicatively coupled to a dynamic force module, such as the computing devices 3074-3078 shown in FIG. 30.

The data insights module 3064 generally allows a user to access and analyze their personal and historical exercise data. Such analysis may include, for example, comparing personal and performance data to one or more benchmarks, comparing including but not limited to, past performances by the users, predefined fitness goals established for the user, and data and records of other users. The user data insight tool 3064 may provide the user's data in a variety of tabular and graphical formats to facilitate analysis by the user.

The workout builder module 3066 enables generation of workout routines. For example, in certain implementations, a user may access the workout builder 3066 and be presented with a list of exercises selectable to generate a workout routine. As part of the workout builder 3066, the user may specify various parameters and factors including, without limitation, a resistance/weight/reactive force, a number of repetitions, an exercise duration, a sequence of exercise, a number of sets, a speed profile for repetitions, a force profile for repetitions, rest durations, and other factors and parameters, as applicable. By selecting one or more exercises and their corresponding parameters and order, the user may generate a custom workout routine that may subsequently be used in conjunction with a dynamic force module. In certain implementations, routines generated by the workout builder tool 3066 may be stored in the cloud-based computing platform 3050 or a data source communicatively coupled thereto and made accessible to users of the system 3000. The workout routines may be made publicly available or otherwise shared with other users of the system 3000. For example, individuals, trainers, actors, fitness celebrities, or other users may generate pre-defined workout routines for themselves or others to follow.

In certain implementations, workout routines may be accompanied by instructional information for equipment required for the workout routine. This content may also be created by, or with the assistance of an artificial intelligence or other automated generation algorithm. Moreover, the workout routine may further include details regarding specific gym facilities. For example, while at a gym facility, a workout routine may guide a user along a path or otherwise to each machine included in the workout routine. Such guidance may be provided by one or more of visual or other cues. For example, a map may be displayed on a computing device of the user including a map of the gym facility in which the user is located and corresponding directions between exercise machines. In another example, the dynamic force modules may include lights, LEDs, or similar display elements that may display particular colors or color sequences based on the workout routine such that the user can readily identify which exercise machines he or she is to use.

The AI/feedback generator module 3068 may include a machine-learning or similar system adapted to provide feedback and recommendations to a user based on, among other things, the user's personal information and exercise history. For example, the AI/feedback generator module 3068 may analyze the user's personal information and exercise history to identify particular areas of weakness or areas of concern in order to recommend particular exercises or workout routines to the user. The AI/feedback generator may also provide recommendations and/or recommended workout schedules to the user based on goals or desired results identified by the user or a doctor, trainer, or similar professional working with the user. In certain implementations, the AI/feedback generator module 3068 may also be used to recommend exercises and workouts to improve client retention for a particular gym facility. For example, the AI/feedback generator module 3068 may identify exercises based on historical user data that are highly correlated with regular and consistent gym attendance and user motivation. The AI/feedback generator module 3068 may then provide recommendations to a user aimed to encourage high participation by the user and high retention for the gym facility.

A content management module 3070 may also be included for managing and distributing content to users of the system. Such content may include, but is not limited to, audio, video, images, text, instructional information, and interactive modules. The content management module 3070 may enable a user of the system or a facility manager to upload, delete, edit, or otherwise manage content. The content management module 3070 may also facilitate distribution of content. In certain implementations, the content management system may also interact with dynamic force modules of the system 3000 to manage content locally stored on the dynamic force modules. For example, in some implementations at least some of the content maintained by cloud-based computing platform 3050 may be cached or otherwise stored locally to facilitate ease and speed of access. In such implementations, the content management module 3070 may manage, among other things, distribution of new content, updates and modifications to previously distributed content, and removal of expired content.

The personal trainer module 3070 generally corresponds to a tool that may be available to a personal trainer for monitoring, tracking, and managing information and workouts for clients of the personal trainer. For example, through the personal trainer module 3070, a personal trainer may be able to select exercises and generate workouts for clients, to track progress and participation of clients, and to communicate with clients. The personal trainer module 3070 may also enable a personal trainer to generate or otherwise upload content, such as instructional or motivational content, for distribution to clients.

In certain implementations, the cloud-based computing platform 3050 may be integrated or otherwise in communication with a booking and reservation system associated with one or more gym facilities. In such implementations, the cloud-based computing platform 3050 may also facilitate a user booking or reserving an exercise machine. The cloud-based computing platform 3050 may also be accessible to gym operators to review such booking and reservation information and to track utilization of equipment.

As previously discussed, dynamic force modules in accordance with the present disclosure may be connected to a network such as, without limitation, the Internet, and may be configured to exchange data with one or more remote computing systems over the network. FIGS. 31-35 illustrate various network topologies to facilitate such communication. The various topologies illustrated in FIGS. 31-35 are intended only as examples for illustrating concepts regarding network topologies. Other network topologies including one or more elements of the following examples as well as other network topologies not specifically discussed herein may also be used in conjunction with the dynamic force modules discussed.

In each of the following example network topologies, one of a dynamic force module or an exercise machine corresponding to a dynamic force module is referred to as being communicatively coupled to other devices, which may include other exercise machines/dynamic force modules and/or computing devices. Such communicative coupling may be facilitated by a communication module of the dynamic force module or a communication module of the exercise machine separate from but in communication with that of the dynamic force module. Accordingly, to the extent the following examples refer to communications including dynamic force modules, such communication may be the result of the dynamic module being communicatively coupled through the exercise machine. Moreover, the term communicative coupling, as used herein, is intended to cover both wired and wireless connections between devices.

Figure 31:
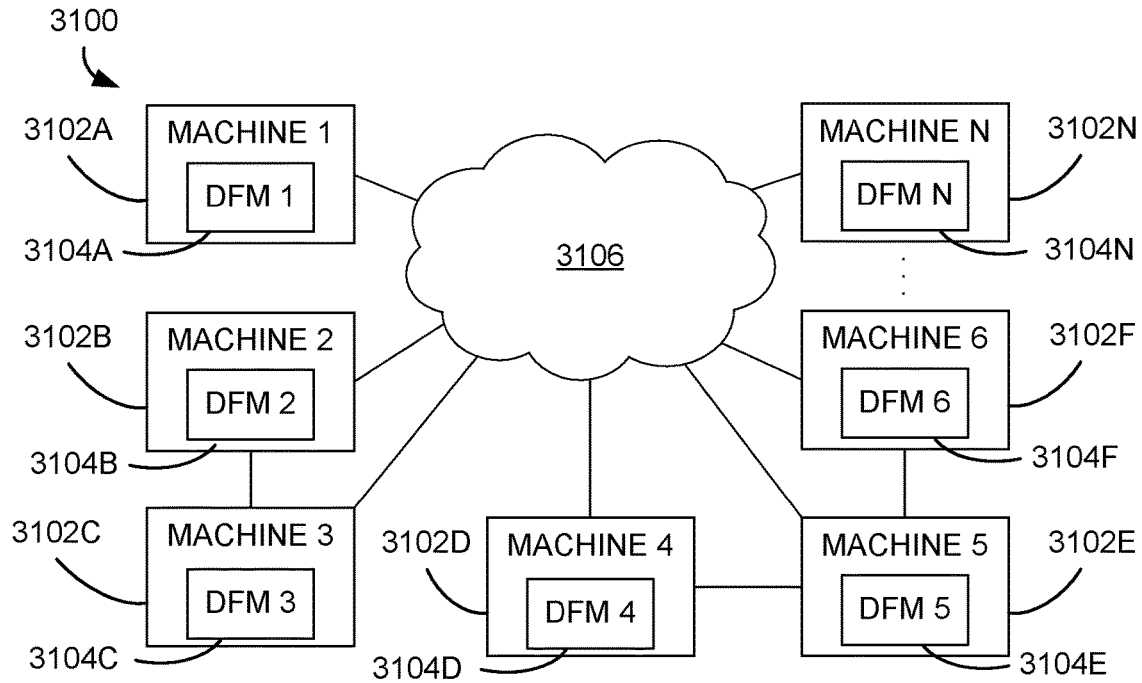
FIG. 31 is a first network topology for communication among multiple dynamic force modules.

Referring now to FIG. 31, a first network topology 3100 is illustrated. The network topology 3100 includes multiple exercise machines 3102A-3102N, each of which includes a respective dynamic force module 3104A-3104N. As illustrated in FIG. 31, each of the exercise machines 3102A-3102N and their respective dynamic force modules 3104A-3104N are communicatively coupled on a one-to-one basis with a cloud-based computing system 3106.

As shown in FIG. 31, the exercise machines 3102A-3102N may also be independent (as is the case with exercise machine 3102A) or may be coupled one or more other exercise machines. For example the exercise machine 3102B is communicatively coupled with the exercise machine 3102C and each of the exercise machines 3102B, 3102C are communicatively coupled to the cloud-based computing system 3106. Similarly, the exercise machine 3102E is communicatively coupled to each of the exercise machines 3102D and 3102F and each of the exercise machines 3102D-3102F are each communicatively coupled to the cloud-based computing system 3106. Accordingly, in certain implementations, exercise machines may be configured to not only share data and information with the cloud-based computing system 3106, but also among each other.

Figure 32:
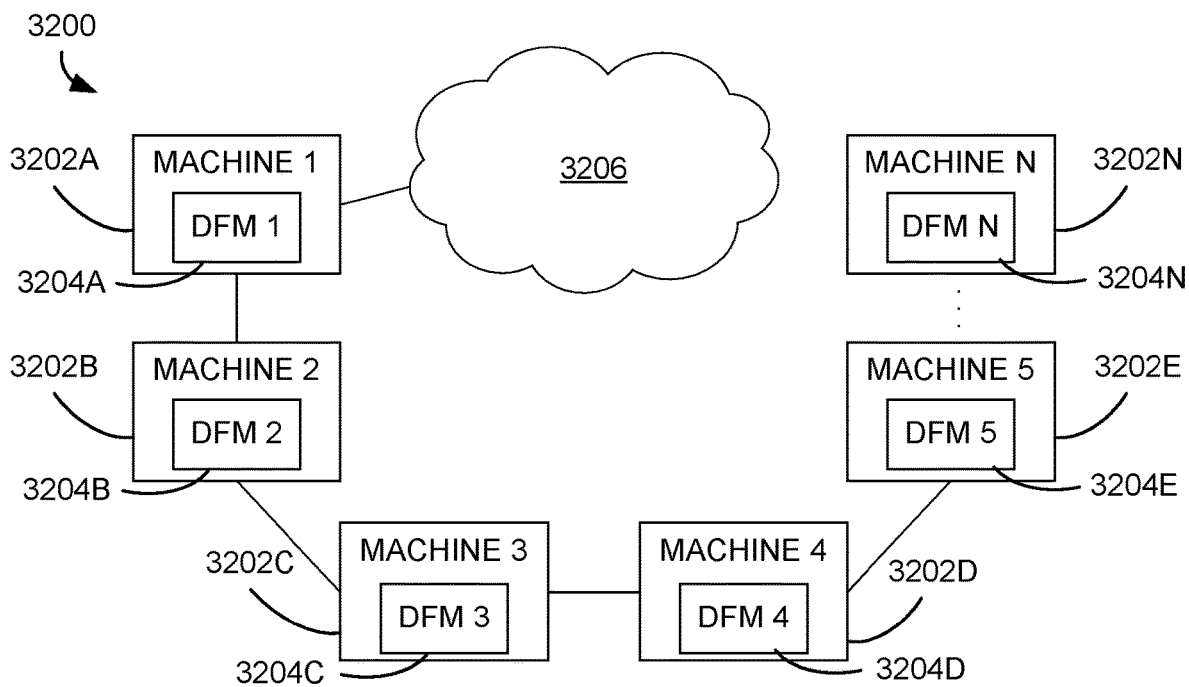
FIG. 32 is a second network topology for communication among multiple dynamic force modules.

Referring next to FIG. 32, a second network topology 3200 is illustrated. The network topology 3200 includes multiple exercise machines 3202A-3202N, each of which includes a respective dynamic force module 3204A-3204N. In contrast to the network topology 3100 of FIG. 31, the network topology 3200 illustrates a daisy chain arrangement. In such an arrangement, one exercise machine 3204A is communicatively coupled to a cloud-based computing system 3206 while each of the remaining exercise machines 3204A-3204N are arranged in a chain arrangement with each of the exercise machines 3204B-3204N communicatively coupled to two neighboring machines.

Figure 33:
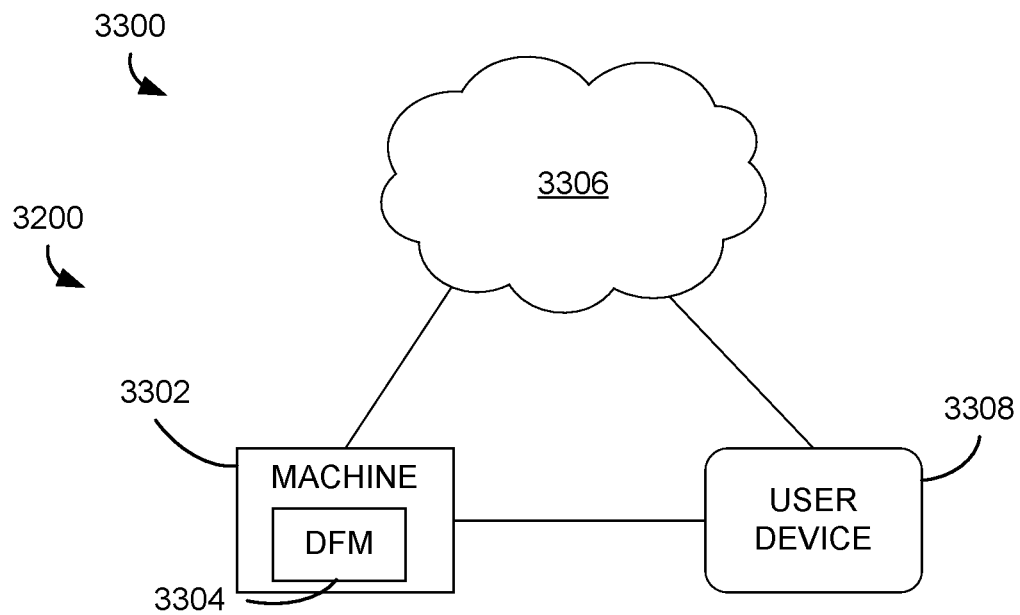
FIG. 33 is a third network topology for communication among multiple dynamic force modules.

FIG. 33 illustrates a third network topology 3300. The third network topology 3300 includes an exercise machine 3302 with a corresponding dynamic force module 3304, which are communicatively coupled to a cloud-based computing system 3306. The network topology 3300 further includes a user device 3308, such as a smart phone, laptop, tablet, or similar computing device. As illustrated, the user device 3308 may be communicatively coupled with each of the exercise machine 3302 and the cloud-based computing system 3306. In such an implementation, the user device 3308 may be used to interact with either the exercise machine 3302 or the cloud-based computing system 3306. For example, during an exercise session, the user device 1206 may dynamically display and allow a user to modify settings of the exercise machine 3302. The user device 3306 may also allow a user to interact with the cloud-based computing system 3306 in order to, among other things, upload user information, review progress and workout history, download exercise routines, and perform other similar functions.

Figure 34:
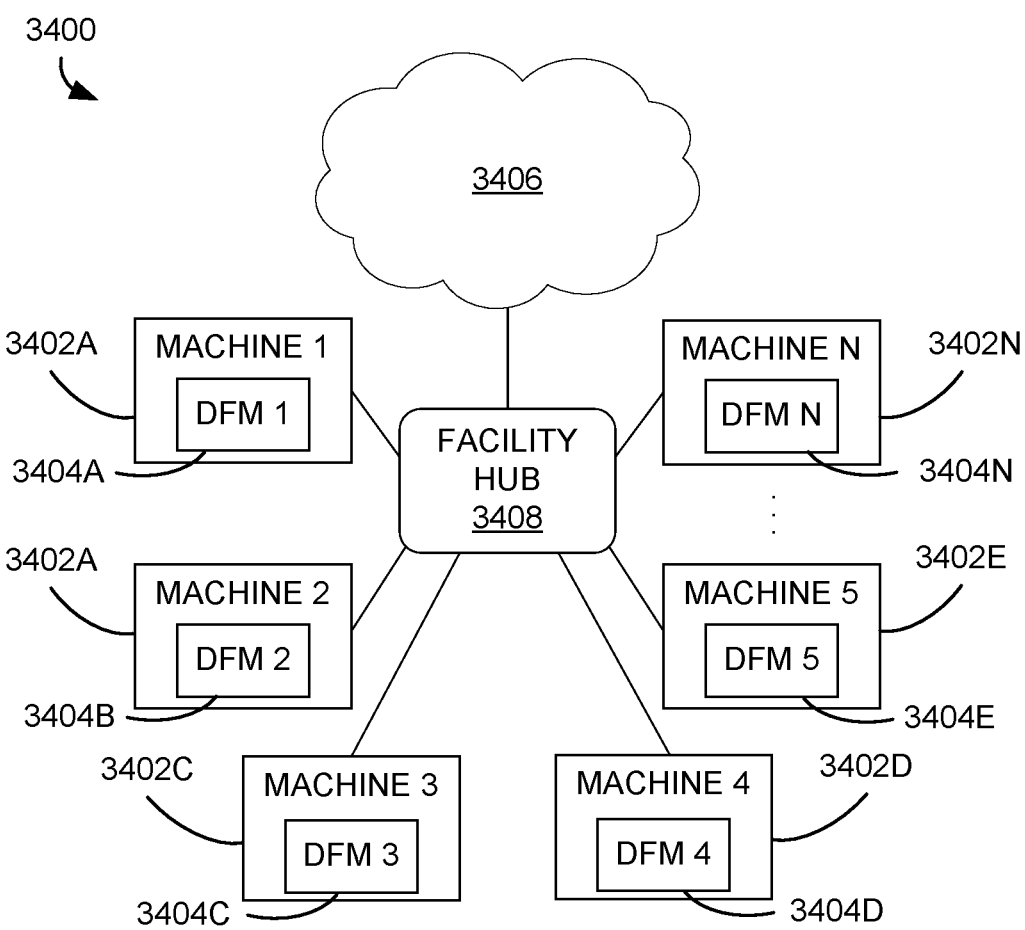
FIG. 34 is a fourth network topology for communication among multiple dynamic force modules.

FIG. 34 illustrates a fourth network topology 3400. The network topology 3400 includes multiple exercise machines 3402A-3402N, each of which includes a respective dynamic force module 3404A-3404N. Each of the exercise machines 3402A-3402N and their respective dynamic force modules 3404A-3404N are communicatively coupled to a facility hub 3408 which is in turn communicatively coupled to a cloud-based computing system 3406. In such an arrangement, the facility hub 3408 may facilitate communication between the exercise machines 3402A-3402N and may perform various functions associated with a particular facility.

Figure 35:
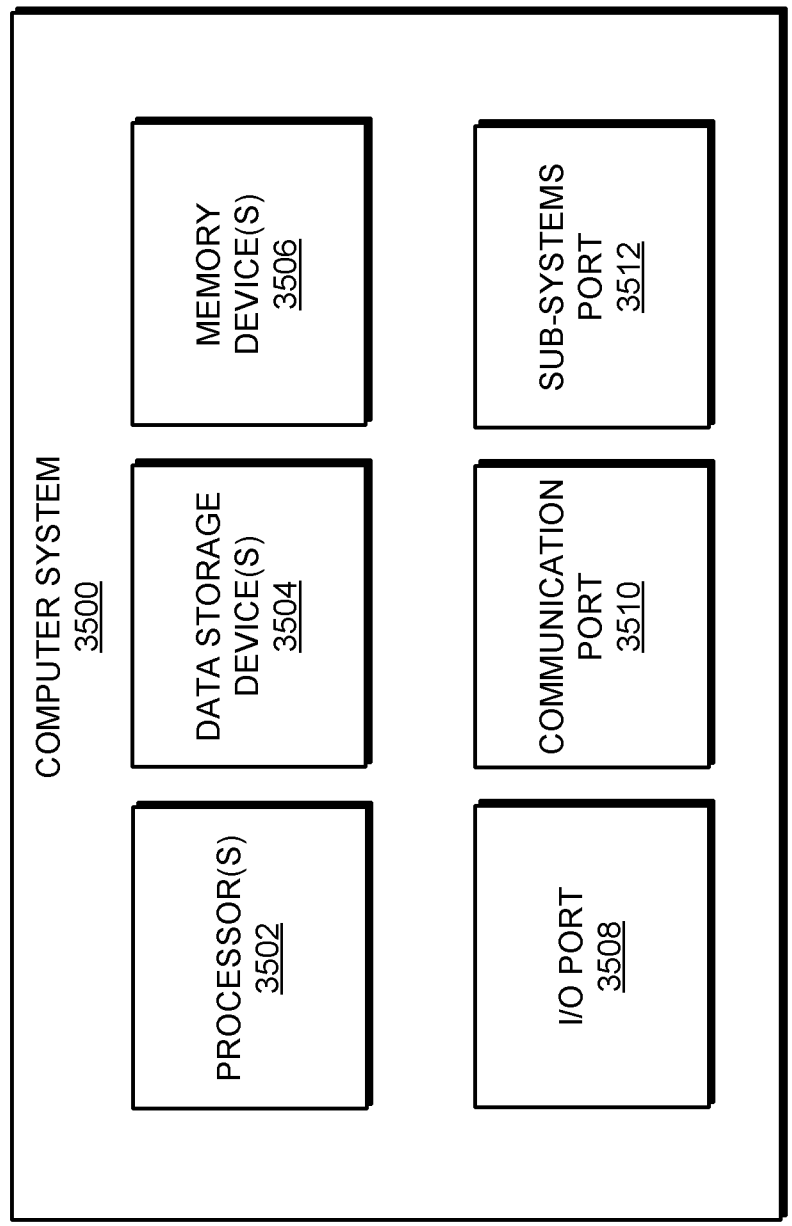
FIG. 35 illustrates a computing system that may be implemented in conjunction with dynamic force modules according to the present disclosure.

FIG. 35 illustrates a system 3500 that may be implemented in conjunction with dynamic force modules according to the present disclosure. As illustrated, the network environment includes multiple gym or similar facilities 3502A-3502N communicatively coupled by respective facility hubs 3504A-3504N to a cloud-based computing system 3506. Each of the gym facilities may include one or more exercise machines, each of which includes a dynamic force module in accordance with the present disclosure.

As illustrated, the cloud-based computing system 3506 may provide networked access to a wealth of tools and features to enhance a user's fitness experience. Such features may be implemented as modules or similar software components executed by one or more computing systems in communication with the cloud-based computing system 3506 and in communication with each of the facilities 3502A-3502N. In certain implementations, the cloud-based computing system 3506 and its corresponding features and tools may also be accessed by a user computing device such as, without limitation, a smartphone, a laptop, a tablet, or other computer.

Dynamic force modules of systems disclosed herein may also be used in conjunction with or be communicatively coupleable to other "smart" network-connected fitness equipment beyond other dynamic force module equipped machines. Examples of such equipment may include sensor equipped sit-up mats, pullup bars, hang boards, free weights, resistance bands, abdominal rollers, bosu balls, treadmills, elliptical machines, computer vision based exercise monitoring systems, or other similar systems.

Referring to FIG. 35, a schematic illustration of an example computing system 3500 having one or more computing units that may implement various systems, processes, and methods discussed herein is provided. For example, the example computing system 3500 may correspond to, among other things, one or more of a dynamic force module, a user computing, or any similar computing device included in a system incorporating dynamic force modules, such as the system 3000 of FIG. 30. It will be appreciated that specific implementations of these devices may be of differing possible specific computing architectures not all of which are specifically discussed herein but will be understood by those of ordinary skill in the art.

The computer system 3500 may be a computing system capable of executing a computer program product to execute a computer process. Data and program files may be input to computer system 3500, which reads the files and executes the programs therein. Some of the elements of the computer system 3500 are shown in FIG. 35, including one or more hardware processors 3502, one or more data storage devices 3504, one or more memory devices 3508, and/or one or more ports 3508-3512. Additionally, other elements that will be recognized by those skilled in the art may be included in the computing system 3500 but are not explicitly depicted in FIG. 35 or discussed further herein. Various elements of the computer system 3500 may communicate with one another by way of one or more communication buses, point-to-point communication paths, or other communication means not explicitly depicted in FIG. 35.

The processor 3502 may include, for example, a central processing unit (CPU), a microprocessor, a microcontroller, a digital signal processor (DSP), and/or one or more internal levels of cache. There may be one or more processors 3502, such that the processor 3502 comprises a single central-processing unit, or a plurality of processing units capable of executing instructions and performing operations in parallel with each other, commonly referred to as a parallel processing environment.

The computer system 3500 may be a conventional computer, a distributed computer, or any other type of computer, such as one or more external computers made available via a cloud computing architecture. The presently described technology is optionally implemented in software stored on data storage device(s) 3504, stored on memory device(s) 3506, and/or communicated via one or more of the ports 3508-3512, thereby transforming the computer system 3500 in FIG. 35 to a special purpose machine for implementing the operations described herein. Examples of the computer system 3500 include personal computers, terminals, workstations, mobile phones, tablets, laptops, personal computers, multimedia consoles, gaming consoles, set top boxes, and the like.

One or more data storage devices 3504 may include any non-volatile data storage device capable of storing data generated or employed within the computing system 3500, such as computer executable instructions for performing a computer process, which may include instructions of both application programs and an operating system (OS) that manages the various components of the computing system 3500. Data storage devices 3504 may include, without limitation, magnetic disk drives, optical disk drives, solid state drives (SSDs), flash drives, and the like. Data storage devices 3504 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. One or more memory devices 3506 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 3504 and/or the memory devices 3506, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 3500 includes one or more ports, such as an input/output (I/O) port 3508, a communication port 3510, and a sub-systems port 3512, for communicating with other computing, network, or similar devices. It will be appreciated that the ports 3508-3512 may be combined or separate and that more or fewer ports may be included in the computer system 3500.

The I/O port 3508 may be connected to an I/O device, or other device, by which information is input to or output from the computing system 3500. Such I/O devices may include, without limitation, one or more input devices, output devices, and/or environment transducer devices.

In one implementation, the input devices convert a human-generated signal, such as, human voice, physical movement, physical touch or pressure, and/or the like, into electrical signals as input data into the computing system 3500 via the I/O port 3508. Similarly, the output devices may convert electrical signals received from the computing system 3500 via the I/O port 3508 into signals that may be sensed as output by a human, such as sound, light, and/or touch. The input device may be an alphanumeric input device, including alphanumeric and other keys for communicating information and/or command selections to the processor 3502 via the I/O port 3508. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

The environment transducer devices convert one form of energy or signal into another for input into or output from the computing system 3500 via the I/O port 3508. For example, an electrical signal generated within the computing system 3500 may be converted to another type of signal, and/or vice-versa. In one implementation, the environment transducer devices sense characteristics or aspects of an environment local to or remote from the computing device 3500, such as, light, sound, temperature, pressure, magnetic field, electric field, chemical properties, physical movement, orientation, acceleration, gravity, and/or the like. Further, the environment transducer devices may generate signals to impose some effect on the environment either local to or remote from the example the computing device 3500, such as, physical movement of some object (e.g., a mechanical actuator), heating or cooling of a substance, adding a chemical substance, and/or the like.

In one implementation, a communication port 3510 is connected to a network by way of which the computer system 3500 may receive network data useful in executing the methods and systems set out herein as well as transmitting information and network configuration changes determined thereby. Stated differently, the communication port 3510 connects the computer system 3500 to one or more communication interface devices configured to transmit and/or receive information between the computing system 3500 and other devices by way of one or more wired or wireless communication networks or connections. Examples of such networks or connections include, without limitation, Universal Serial Bus (USB), Ethernet, WiFi, Bluetooth®, Near Field Communication (NFC), Long-Term Evolution (LTE), and so on. One or more such communication interface devices may be utilized via communication port 3510 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 3510 may communicate with an antenna for electromagnetic signal transmission and/or reception.

The computer system 3500 may include a sub-systems port 3512 for communicating with one or more sub-systems, to control an operation of the one or more sub-systems, and to exchange information between the computer system 3500 and the one or more sub-systems. Examples of such sub-systems include, without limitation, imaging systems, radar, lidar, motor controllers and systems, battery controllers, fuel cell or other energy storage systems or controls, light systems, navigation systems, environment controls, entertainment systems, and the like.

The system set forth in FIG. 35 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

Numerous examples are provided herein to enhance understanding of the present disclosure. A specific set of statements are provided as follows.

Statement A1: A dynamic force module for use in an exercise machine is provided. The dynamic force module includes a motor assembly including a motor and a cable selectively extendable and retractable by actuation of the motor. The dynamic force module further includes a frame coupled to the motor assembly and a load measurement device coupled to the frame and adapted to measure loading of the frame in response to tension applied to the cable.

Statement A2: A dynamic force module is disclosed according to Statement A1, wherein the motor assembly further includes a motor shaft extending from the motor, the actuation of the motor including rotation of the motor shaft, and a drum coupled to each of the motor shaft and the cable such that the cable unspools from the drum when the cable is extended and spools onto the drum when the cable is retracted.

Statement A3: A dynamic force module is disclosed according to Statement A2, wherein the drum comprises an outer helical groove shaped to receive the cable such that the cable does not overlap itself when spooled on the drum.

Statement A4: A dynamic force module is disclosed according to Statement A2, the dynamic force module further including at least one proximity sensor coupled to the frame and disposed adjacent the drum, the proximity sensor configured to identify a presence of the cable at a location along the drum.

Statement A5: A dynamic force module is disclosed according to Statement A2, the dynamic force module further including at least one guard disposed adjacent the drum, the guard configured to at least partially retain the cable.

Statement A6: A dynamic force module is disclosed according to Statement A5, wherein the at least one guard further includes at least one of a ridge, a gusset, and a lip adapted to impart structural strength to the at least one guard.

Statement A7: A dynamic force module is disclosed according to any of preceding Statements A1-A6, wherein the frame includes a motor bracket coupled to the motor assembly and a base plate offset from the motor bracket.

Statement A8: A dynamic force module is disclosed according to any of preceding Statements A7-A8, wherein the motor bracket is coupled to the base plate such that the motor bracket is cantilevered.

Statement A9: A dynamic force module is disclosed according to any of preceding Statements A7-A10, wherein the motor bracket is coupled to the base plate by a sidewall.

Statement A10: A dynamic force module is disclosed according to Statement A9, wherein the sidewall includes one or more cutouts.

Statement A11: A dynamic force module is disclosed according to any of preceding Statements A7-A10, wherein the frame further includes a spring element disposed between the motor bracket and the base plate.

Statement A12: A dynamic force module is disclosed according to Statement A11, wherein the spring element is formed into a second sidewall disposed opposite the sidewall.

Statement A13: A dynamic force module is disclosed according to any of preceding statements A7-A12, wherein the strain measurement device includes one or more load cells disposed between the motor bracket and the base plate.

Statement A14: A dynamic force module is disclosed according any of preceding statements A9-A12, wherein the strain measurement device includes one or more strain gauges coupled to the sidewall.

Statement A15: A dynamic force module is disclosed according to Statement A7, wherein the motor bracket includes a pair of parallel rails supported offset from the base plate.

Statement A16: A dynamic force module is disclosed according to Statement A15, wherein the parallel rails are supported offset from the base plate by respective adjustment screws coupled to the base plate.

Statement A17: A dynamic force module is disclosed according to any of preceding Statements A15 and A16, wherein the load measurement device includes at least one load cell supported adjacent to one of the parallel rails and opposite the base plate by a bracket such that tension applied to the cable causes the one of the parallel rails to compress the load cell.

Statement B1: A dynamic force module for use in an exercise machine is provided. The dynamic force module includes a motor for extending and retracting a cable in response to a control signal, the motor supported by a frame. The dynamic force module further includes a load sensing device configured to measure a load on the frame resulting from tension applied to the cable and a controller communicatively coupled to each of the motor and the load sensing device. The controller is adapted to actuate the motor in response to the load on the frame in accordance with a force profile that provides a relationship between a first parameter associated with operation of the motor and a second parameter corresponding to execution of an exercise by a user of the exercise machine.

Statement B2: A dynamic force module is disclosed according to Statement B1, wherein the frame includes a motor bracket coupled to the motor and a base plate offset from the motor bracket.

Statement B3: A dynamic force module is disclosed according to Statement B4, wherein the load sensing device includes at least one load cell disposed between the motor bracket and the base plate.

Statement B4: A dynamic force module is disclosed according to Statement B4, wherein the frame further includes a sidewall extending between the motor bracket and the base plate and the load sensing device includes at least one strain gauge coupled to the sidewall.

Statement B5: A dynamic force module is disclosed according to any of preceding Statements B1-B4, wherein the force profile includes a range of values of the second parameter over which the first parameter is maintained at a predetermined value.

Statement B6: A dynamic force module is disclosed according to any of preceding Statements B1-B4, wherein the force profile includes a first portion corresponding to a concentric phase of the exercise and a second portion corresponding to an eccentric phase of the exercise, and a value of the first parameter corresponding to a value of the second parameter is varied depending on whether the user is in the first phase or the second phase.

Statement B7: A dynamic force module is disclosed according to any of preceding Statements B1-B4, wherein the force profile includes a range of values of the second parameter over which corresponding values of the first parameter are based on random noise applied to a nominal value.

Statement B8: A dynamic force module is disclosed according to any of preceding Statements B1-B4, wherein the force profile includes a first portion corresponding to a first phase of the exercise over which the second parameter is increased and a second portion corresponding to a second phase of the exercise over which the second parameter is decreased, a value of the first parameter reducing exponentially over the first portion and the value of the first parameter being held constant during the second portion.

Statement B9: A dynamic force module is disclosed according to any of preceding Statements B1-B8, wherein the first parameter is at least one of a force output by the motor and a rotational speed of the motor.

Statement B10: A dynamic force module is disclosed according to any of preceding Statements B1-B9, wherein the second parameter is at least one of a position of the user, a speed of the user, and a force output of the user.

Statement B11: A dynamic force module is disclosed according to any of preceding Statements B1-B8, wherein the controller is configured to automatically reduce the first parameter in response to the second parameter being below a predetermined threshold.

Statement B12: A dynamic force module is disclosed according to any of preceding Statements B11, wherein the first parameter is a force output of the motor and the second output is a force output by the user.

Statement B13: A dynamic force module is disclosed according to any of preceding Statements B1-B12, wherein the force profile is based, at least in part, on functionality of a second dynamic force module of the exercise machine.

Statement B14: A dynamic force module is disclosed according to any of preceding Statements B1-B12, wherein the controller is communicatively coupled to a user feedback device.

Statement B15: A dynamic force module is disclosed according to any of preceding Statements 14, wherein the user feedback device includes at least one of an audio feedback device, a haptic feedback device, and a visual feedback device.

Statement B16: A dynamic force module is disclosed according to any of preceding Statements 14 and 15, wherein the controller is configured to vary at least one of an a frequency and an intensity of feedback provided by the user feedback device based on deviation between a measured parameter of the user during execution of the exercise and one or more target values for the measured parameter.

Statement B17: A dynamic force module is disclosed according to Statement B14, wherein the user feedback device is a display and user feedback is provided by an interactive animation shown on the display.

Statement B18: A dynamic force module is disclosed according to Statement B17, wherein the interactive animation includes a two-dimensional space and a marker movable within the two-dimensional space according to values of each of a first parameter and a second parameter, the first parameter corresponding to a measured parameter of the user during execution of the exercise.

Statement B19: A dynamic force module is disclosed according to Statement B18, wherein the interactive animation further includes one or more boundaries corresponding to one or more ranges of the measured parameter.

Statement B20: A dynamic force module is disclosed according to Statement B19, wherein feedback is provided to the user based on whether the user maintains the marker at least one of inside of or outside of the one or more boundaries.

Statement B21: A dynamic force module is disclosed according to Statement B18, wherein the interactive animation includes one or more objects disposed in the two-dimensional space.

Statement B22: A dynamic force module is disclosed according to Statement B21, wherein feedback is provided to the user in response to the marker at least one of contacting or avoiding the one or more objects.

Statement B21: A dynamic force module is disclosed according to Statement B17, wherein the interactive animation includes one dimensional object and a marker that moves along the one dimensional object in response to the measured parameter.

Statement B21: A dynamic force module is disclosed according to Statement B17, wherein the interactive animation includes a simulated object and the force profile executed during the interactive animation simulates reactive forces associated with interactions with the object.

Statement B22: A dynamic force module is disclosed according to Statement B21, wherein the interactive animation includes an animation of the simulated object being at least one of caught, received, passed, or thrown.

Statement B23: A dynamic force module is disclosed according to Statement B17, wherein the interactive animation includes a first segment during which the controller executes the force profile and a second segment during which a second controller executes a second force profile.

Statement B24: A dynamic force module is disclosed according to Statement B23, wherein the second controller is the same as the controller and each of the first force profile and the second force profile are executed by the controller.

Statement B25: A dynamic force module is disclosed according to Statement B23, wherein the second controller is a controller of a second dynamic force module such that the second force profile is executed by the second dynamic force module.

Statement C1: A system for managing dynamic resistance exercise equipment is provided. The system includes a computing device communicatively coupled to a force profile data source for storing force profiles. The computing device is configured to receive a request from a dynamic force module for a force profile stored on the data source and to transmit the force profile to the dynamic force module. The force profile is executable by the dynamic force module and provides a relationship between a first parameter associated with operation of an actuator of the dynamic force module and a second parameter corresponding to execution of an exercise by a user of an exercise machine within which the dynamic force module is incorporated.

Statement C2: A system for managing dynamic resistance exercise equipment is disclosed according to Statement C1, the system further including a user information data source for storing user information and that is communicatively coupled to the computing device. The computing device is further configured to receive, from the dynamic force module, exercise data corresponding to an exercise performed by the user using the exercise machine and at least one of update and generate an entry of the user information source corresponding to the user including the exercise data.

Statement C3: A system for managing dynamic resistance exercise equipment is disclosed according to any of preceding Statements C1 and C2, wherein the computing device is further configured to receive authentication data from the dynamic force module associated with the user and to provide the force profile in response to authenticating the user.

Statement C4: A system for managing dynamic resistance exercise equipment is disclosed according to Statement C3, wherein the computing device is further configured to transmit auto-configuration data to the dynamic force module, the auto-configuration data causing the dynamic force module to actuate one or more actuators of the exercise machine.

Statement C5: A system for managing dynamic resistance exercise equipment is disclosed according to Statement C4, wherein the auto-configuration data is based on user information stored in the user information data source.

Statement C6: A system for managing dynamic resistance exercise equipment is disclosed according to any of preceding Statements C3-C4, wherein the authentication data corresponds to biometric data including at least one of finger print data, facial recognition data, force signature data, and voice data.

Although various representative embodiments have been described above with a certain degree of particularity, those skilled in the art could make numerous alterations to the disclosed embodiments without departing from the spirit or scope of the inventive subject matter set forth in the specification. All directional references (e.g., upper, lower, upward, downward, left, right, leftward, rightward, top, bottom, above, below, vertical, horizontal, clockwise, and counterclockwise) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

In some instances, components are described with reference to "ends" having a particular characteristic and/or being connected to another part. However, those skilled in the art will recognize that the present invention is not limited to components which terminate immediately beyond their points of connection with other parts. Thus, the term "end" should be interpreted broadly, in a manner that includes areas adjacent, rearward, forward of, or otherwise near the terminus of a particular element, link, component, member or the like. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

The invention claimed is:

1. A dynamic force module for use in an exercise machine, the dynamic force module comprising:
    a housing defining an aperture;
    a motor assembly disposed within the housing, the motor assembly comprising:
        a motor;
        a motor shaft extending from the motor; and a cable spooled about the motor shaft and selectively extendable and retractable by actuating the motor to rotate the motor shaft;

a frame coupled to and supporting the motor within the housing; and a load measurement device adapted to measure a load responsive to tension on the cable, wherein the cable is routed directly from the motor shaft through the aperture of the housing to an exterior of the housing.

2. The dynamic force module of claim 1, wherein the motor assembly further comprises:

a drum extending about the motor shaft such that the cable is spooled about the drum and at least a portion of the drum is aligned with the aperture, wherein the cable unspools from the drum when the cable is extended and spools onto the drum when the cable is retracted.

3. The dynamic force module of claim 2, wherein the drum comprises an outer helical groove shaped to receive the cable such that the cable does not overlap itself when spooled on the drum.

4. The dynamic force module of claim 2 further comprising at least one proximity sensor coupled to the frame and disposed adjacent the drum, the proximity sensor configured to identify a presence of the cable at a location along the drum.

5. The dynamic force module of claim 1, wherein:

the frame comprises a motor bracket directly coupled to the motor and a base plate offset from the motor bracket, each of the motor bracket and base plate extend parallel to an axis of the motor, and the load measurement device comprises a load cell coupled to each of the motor bracket and the base plate and disposed between the motor bracket and the base plate.

6. The dynamic force module of claim 5, wherein the motor bracket is coupled to the base plate such that the motor bracket is cantilevered.

7. The dynamic force module of claim 5, wherein the frame further comprises a spring element disposed between the motor bracket and the base plate.

8. The dynamic force module of claim 1, wherein:

the frame comprises a motor bracket directly coupled to the motor and a base plate offset from the motor bracket, each of the motor bracket and base plate extend parallel to an axis of the motor, the motor bracket is coupled to the base plate by a sidewall extending between the motor bracket and the base plate, and the load measurement device comprises a strain gauge coupled to the sidewall.

9. The dynamic force module of claim 1, wherein:

the frame comprises a floating member, the floating member is in contact with the load measurement device, and the load applied to the frame is a load applied to the floating member.

10. The dynamic force module of claim 1, wherein the load is applied to the frame.

* * * * *